(12) United States Patent
Vidlund et al.

(10) Patent No.: US 11,154,399 B2
(45) Date of Patent: Oct. 26, 2021

(54) PROSTHETIC HEART VALVES AND APPARATUS AND METHODS FOR DELIVERY OF SAME

(71) Applicant: Tendyne Holdings, Inc., St. Paul, MN (US)

(72) Inventors: Zachary Vidlund, Robbinsdale, MN (US); Zachary Robert Kowalski, Maple Grove, MN (US); Son Mai, Centerville, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 0 days.

(21) Appl. No.: 16/615,185

(22) PCT Filed: Jul. 12, 2018

(86) PCT No.: PCT/US2018/041867
§ 371 (c)(1),
(2) Date: Nov. 20, 2019

(87) PCT Pub. No.: WO2019/014473
PCT Pub. Date: Jan. 17, 2019

(65) Prior Publication Data
US 2020/0155311 A1 May 21, 2020

Related U.S. Application Data

(60) Provisional application No. 62/532,659, filed on Jul. 14, 2017, provisional application No. 62/532,152, filed on Jul. 13, 2017.

(51) Int. Cl.
*A61F 2/24* (2006.01)
(52) U.S. Cl.
CPC .......... *A61F 2/2436* (2013.01); *A61F 2/2418* (2013.01); *A61F 2210/0014* (2013.01)

(58) Field of Classification Search
CPC ............ A61F 2/2466; A61F 2220/0016; A61F 2/2409; A61F 2/90; A61F 2220/0033;
(Continued)

(56) References Cited

U.S. PATENT DOCUMENTS 2,697,008 A 12/1954 Ross
3,409,013 A 11/1968 Berry
(Continued)

FOREIGN PATENT DOCUMENTS

CN 1486161 A 3/2004
CN 1961845 A 5/2007
(Continued)

OTHER PUBLICATIONS

US 9,155,620 B2, 10/2015, Gross et al. (withdrawn)
(Continued)

*Primary Examiner* — Ann Schillinger
(74) *Attorney, Agent, or Firm* — Lerner, David, Littenberg, Krumholz & Mentlik, LLP

(57) ABSTRACT

Apparatus and methods are described herein for use in the transvascular delivery and deployment of a prosthetic heart valve. In some embodiments, an apparatus includes an outer sheath, a tube member movably disposed within the outer sheath, a retention device coupled to the tube member, and a valve holder. A prosthetic heart valve is disposed within the outer sheath and includes an outer frame and an inner frame that is removably coupled to the valve holder. The outer frame is disposed in an inverted configuration relative to the inner frame. A first actuation wire is releasably coupled to a first portion of the outer frame and releasably coupled to the retention device at a first location on the retention device. A second actuation wire is releasably
(Continued)

coupled to a second portion of the outer frame and releasably coupled to the retention device at a second location on the retention device.

5 Claims, 77 Drawing Sheets

(58) Field of Classification Search
CPC ............ A61F 2/2427; A61F 2220/0091; A61F 2/243; A61F 2/2439; A61F 2002/016; A61F 2002/91558; A61F 2002/91566; A61F 2002/91575; A61F 2002/9511; A61F 2002/9665; A61F 2220/0008; A61F 2/2436; A61F 2/2418; A61F 2210/0014; A61F 2002/9965
See application file for complete search history.

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |

(56) References Cited

U.S. PATENT DOCUMENTS

| | | |
|---|---|---|
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,361,137 B2 | 4/2008 | Taylor et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |

(56) References Cited

U.S. PATENT DOCUMENTS

| | | |
|---|---|---|
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,961,597 B2 | 2/2015 | Subramanian et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,468,526 B2 | 10/2016 | Subramanian et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,848,880 B2 | 12/2017 | Coleman et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 10,226,334 B2 | 3/2019 | Rowe et al. |
| 10,646,342 B1 * | 5/2020 | Marr ............ A61B 17/1285 |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0069593 A1 | 4/2003 | Tremulis et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049211 A1 | 3/2004 | Tremulis et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0210304 A1 | 10/2004 | Seguin et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |

(56) References Cited

U.S. PATENT DOCUMENTS

| | | |
|---|---|---|
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0074484 A1 | 4/2006 | Huber |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1* | 8/2007 | Forster .................. A61F 2/243 623/2.11 |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0109069 A1 | 5/2008 | Coleman et al. |
| 2008/0114442 A1 | 5/2008 | Mitchell et al. |
| 2008/0125861 A1 | 5/2008 | Webler et al. |
| 2008/0140189 A1 | 6/2008 | Nguyen et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |

(56) References Cited

U.S. PATENT DOCUMENTS

| | | |
|---|---|---|
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0004740 A1 | 1/2010 | Seguin et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0121435 A1 | 5/2010 | Subramanian et al. |
| 2010/0121437 A1 | 5/2010 | Subramanian et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280589 A1 | 11/2010 | Styrc |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0213459 A1 | 9/2011 | Garrison et al. |
| 2011/0218619 A1 | 9/2011 | Benichou et al. |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0010700 A1 | 1/2012 | Spenser |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0109079 A1 | 5/2012 | Asleson et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0245678 A1 | 9/2012 | Solem |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0103140 A1 | 4/2013 | Subramanian et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0226290 A1 | 8/2013 | Yellin et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0304200 A1 | 11/2013 | McLean et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2013/0338764 A1 | 12/2013 | Thornton et al. |
| 2014/0005778 A1 | 1/2014 | Buchbinder et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0257466 A1 | 9/2014 | Board et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358222 A1 | 12/2014 | Gorman, III et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson |
| 2015/0223934 A1 | 8/2015 | Vidlund et al. |

(56) References Cited

U.S. PATENT DOCUMENTS

| | | |
|---|---|---|
| 2015/0223935 A1 | 8/2015 | Subramanian et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean |
| 2015/0335424 A1 | 11/2015 | McLean |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0012305 A1 | 1/2016 | Cocquelin et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan |
| 2016/0143736 A1 | 5/2016 | Vidlund |
| 2016/0151155 A1 | 6/2016 | Lutter et al. |
| 2016/0206280 A1 | 7/2016 | Vidlund et al. |
| 2016/0242902 A1 | 8/2016 | Morriss |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1* | 3/2017 | Vidlund ............... A61F 2/2418 |
| 2017/0100245 A1 | 4/2017 | Subramanian et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |
| 2018/0193138 A1 | 7/2018 | Vidlund |
| 2019/0183642 A1* | 6/2019 | Tegels .................... A61F 2/243 |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101984938 A | 3/2011 |
| CN | 102791223 A | 11/2012 |
| CN | 102869317 A | 1/2013 |
| CN | 102869318 A | 1/2013 |
| CN | 102869321 A | 1/2013 |
| CN | 103220993 A | 7/2013 |
| CN | 103974674 A | 8/2014 |
| CN | 102639179 B | 10/2014 |
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 B1 | 11/2005 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| JP | 2003505146 A | 2/2003 |
| JP | 2005515836 A | 6/2005 |
| JP | 2009514628 A | 4/2009 |
| JP | 2009519783 A | 5/2009 |
| JP | 2013512765 A | 4/2013 |
| NL | 1017275 C2 | 8/2002 |
| SU | 1271508 A1 | 11/1986 |
| WO | 9217118 A1 | 10/1992 |
| WO | 9301768 A1 | 2/1993 |
| WO | 9829057 | 7/1998 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 2000041652 | 7/2000 |
| WO | 2000047139 A1 | 8/2000 |
| WO | 2001035878 A2 | 5/2001 |
| WO | 2001049213 A2 | 7/2001 |
| WO | 2001054624 A1 | 8/2001 |
| WO | 2001054625 A1 | 8/2001 |
| WO | 2001056512 A1 | 8/2001 |
| WO | 2001061289 A1 | 8/2001 |
| WO | 2001076510 A2 | 10/2001 |
| WO | 2001082840 A1 | 11/2001 |
| WO | 2002004757 A1 | 1/2002 |
| WO | 2002022054 A1 | 3/2002 |
| WO | 2002028321 A2 | 4/2002 |
| WO | 2002036048 A1 | 5/2002 |
| WO | 2002041789 A2 | 5/2002 |
| WO | 2002043620 A1 | 6/2002 |
| WO | 2002049540 A2 | 6/2002 |
| WO | 2002076348 A1 | 10/2002 |
| WO | 2003003943 A2 | 1/2003 |
| WO | 2003030776 A2 | 4/2003 |
| WO | 2003047468 A1 | 6/2003 |
| WO | 2003049619 A2 | 6/2003 |
| WO | 2004019825 A1 | 3/2004 |
| WO | 2005102181 A1 | 11/2005 |
| WO | 2006014233 A2 | 2/2006 |
| WO | 2006034008 A2 | 3/2006 |
| WO | 2006064490 A1 | 6/2006 |
| WO | 2006070372 A2 | 7/2006 |
| WO | 2006105009 A1 | 10/2006 |
| WO | 2006113906 A1 | 10/2006 |
| WO | 2006127756 A2 | 11/2006 |
| WO | 2007081412 A1 | 7/2007 |
| WO | 2007100408 A2 | 9/2007 |
| WO | 2008005405 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009132187 A1 | 10/2009 |
| WO | 2010090878 A2 | 8/2010 |
| WO | 2010098857 A1 | 9/2010 |
| WO | 2010121076 A2 | 10/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | 2011106735 A1 | 9/2011 |

(56) References Cited

FOREIGN PATENT DOCUMENTS

| | | | |
|---|---|---|---|
| WO | 2011109813 A2 | 9/2011 | |
| WO | 2011159342 A1 | 12/2011 | |
| WO | 2011163275 A2 | 12/2011 | |
| WO | 2012027487 A2 | 3/2012 | |
| WO | 2012036742 A2 | 3/2012 | |
| WO | 2012095116 A1 | 7/2012 | |
| WO | 2012177942 A2 | 12/2012 | |
| WO | 2013/028387 A2 | 2/2013 | |
| WO | 2013045262 A1 | 4/2013 | |
| WO | 2013059747 A1 | 4/2013 | |
| WO | 2013096411 A1 | 6/2013 | |
| WO | 2013096757 A1 | 6/2013 | |
| WO | 2013116785 A1 | 8/2013 | |
| WO | 2013175468 A2 | 11/2013 | |
| WO | 2014121280 A2 | 8/2014 | |
| WO | 2014138284 A1 | 9/2014 | |
| WO | 2014144020 A1 | 9/2014 | |
| WO | 2014144937 A2 | 9/2014 | |
| WO | 2014162306 A2 | 10/2014 | |
| WO | 2014189974 A1 | 11/2014 | |
| WO | 2014194178 A1 | 12/2014 | |
| WO | 2014210124 A1 | 12/2014 | |
| WO | 2015051430 A1 | 4/2015 | |
| WO | 2015058039 A1 | 4/2015 | |
| WO | 2015063580 A2 | 5/2015 | |
| WO | 2015065646 A1 | 5/2015 | |
| WO | 2015120122 A2 | 8/2015 | |
| WO | 2015138306 A2 | 9/2015 | |
| WO | 2015173609 A1 | 11/2015 | |
| WO | 2016112085 A2 | 7/2016 | |
| WO | WO-2016112085 A2 * | 7/2016 | ........... A61F 2/2418 |
| WO | 2016126942 A2 | 8/2016 | |
| WO | 2016168609 A1 | 10/2016 | |
| WO | 2016196933 A1 | 12/2016 | |
| WO | 2017096157 A1 | 6/2017 | |
| WO | 2017132008 A1 | 8/2017 | |
| WO | 2017218375 A1 | 12/2017 | |
| WO | 2018005779 A1 | 1/2018 | |
| WO | 2018013515 A1 | 1/2018 | |

OTHER PUBLICATIONS

"Shape Memory Alloys," Retrieved from the Internet: <http://webdocs.cs.ualberta.ca/~database/MEMS/sma.html>, Feb. 5, 2016, 3 pages.

Al Zaibag, Muayed, et al., "Percutaneous Balloon Valvotomy in Tricuspid Stenos's," British Heart Journal, Jan. 1987, vol. 57, No. 1, pp. 51-53.

Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.

Almagor, Y. et al., "Balloon Expandable Stent Implantation in Stenotic Right Heart Valved Conduits," Journal of the American College of Cardiology, Nov. 1, 1990, 16(6):1310-1314.

Andersen, H. R., "History of Percutaneous Aortic Valve Prosthesis," Herz, Aug. 2009, 34(5):343-346.

Andersen, H. R., "Transluminal catheter implanted prosthetic heart valves," International Journal of Angiology, 1998, 7(2):102-106.

Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.

Boudjemline, Y. et al., "Steps Toward the Percutaneous Replacement of Atrioventricular Valves: An Experimental Study," Journal of the American College of Cardiology, Jul. 2005, 46(2):360-365.

Buckberg, G. et al., "Restoring Papillary Muscle Dimensions During Restoration in Dilated Hearts," Interactive Cardiovascular and Thoracic Surgery, 2005, 4:475-477.

Chamberlain, G., "Ceramics Replace Body Parts," Design News, Jun. 9, 1997, Issue 11, vol. 52, 5 pages.

Choo, S. J. et al., "Aortic Root Geometry: Pattern of Differences Between Leaflets and Sinuses of Valsava," The Journal of Heart Valve Disease, Jul. 1999, 8:407-415.

Cullen, et al., "Transvenous, Antegrade Melody Valve-in-Valve Implantation for Bioprosthetic Mitral and Tricuspid Valve Dysfunction", JACC: Cardiovascular Interventions, vol. 6, No. 6, Jun. 2013, pp. 598-605.

Declaration of Malcolm J. R. Dalrymple-Hay, Nov. 9, 2012, pp. 1-11; with Curriculum Vitae, Oct. 4, 2012.

Dotter, C. T. et al., "Transluminal Treatment of Arteriosclerotic Obstruction. Description of a New Technic and a Preliminary Report of its Application," Circulation, Nov. 1964, 30:654-670.

Drawbaugh, K., "Feature—Heart Surgeons Explore Minimally Invasive Methods," Reuters Limited, Jul. 16, 1996, 3 pages.

G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.

Gray, H., The Aorta, Anatomy of the Human Body, 1918, Retrieved from the Internet <http://www.bartleby.com/107/142.html>, Dec. 10, 2012, 5 pages.

Gray, H., The Heart, Anatomy of the Human Body, 1918, Retrieved from the Internet <http://education.yahoo.com/reference/gray/subjects/subject/138>, Aug. 10, 2012, 9 pages.

Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.

H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.

Inoue, K. et al., "Clinical Application of Transvenous Mitral Commissurotomy by a New Balloon Catheter," The Journal of Thoracic and Cardiovascular Surgery, 1984, 87:394-402.

International Search Report and Written Opinion for International Application No. PCT/US2016/012305, dated Aug. 3, 2016, 18 pages.

International Search Report and Written Opinion from PCT/US2018/041867, dated Nov. 13, 2018, pp. 1-36.

Jin, X. Y. et al., "Aortic Root Geometry and Stentless Porcine Valve Competence," Seminars in Thoracic and Cardiovascular Surgery, Oct. 1999, 11(4):145-150.

Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.

Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili . . . ,>, published Jan. 3, 1991,retrieved from the Internet on Feb. 5, 2016, 3 pages.

Lawrence, D. D., "Percutaneous Endovascular Graft: Experimental Evaluation," Radiology, 1987, 163:357-360.

Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.

Lutter, G. et al., "Mitral Valved Stent Implantation," European Journal of Cardia-Thoracic Surgery, 2010, 38:350-355, 2 pages.

Ma, L. et al., "Double-crowned valved stents for off-pump mitral valve replacement," European Journal of Cardio-Thoracic Surgery, Aug. 2005, 28(2): 194-198.

Moazami, N. et al., "Transluminal aortic valve placement: A feasibility study with a newly designed collapsible aortic valve," ASAIO Journal, Sep./Oct. 1996, 42(5):M381-M385.

Orton, C., "Mitralseal: Hybrid Transcatheter Mitral Valve Replacement," Symposium: Small Animal Proceedings, 2011, pp. 311-312.

Pavcnik, D. et al. "Development and Initial Experimental Evaluation of a Prosthetic Aortic Valve for Transcatheter Placement," Radiology, 1992; 183:151-154.

(56) References Cited

OTHER PUBLICATIONS

Porstmann, W. et al., "Der Verschlul?. des Ductus Arteriosus Persistens ohne Thorakotomie," Thoraxchirurgie Vaskulare Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196( 11 ): 173-174.
Rashkind, W. J., "Historical Aspects of Interventional Cardiology: Past, Present, Future," Texas Heart Institute Journal, Dec. 1986, 13(4):363-367.
Reul, H. et al., "The Geomety of the Aortic Root in Health, at Valve Disease and After Valve Replacement," J. Biomechanics, 1990, 23(2):181-191.
Robert C. Ashton Jr., "Development of an Intraluminal Device for the Treatment of Aortic Regurgitation: Prototype and in Vitro Testing System," Journal of Thoracic and Cardiovascular Surgery, 1996, Issue/vol. 112, pp. 979-983.
Rosch, J. et al., "The Birth, Early Years and Future of Interventional Radiology," J Vase Interv Radiol., Jul. 2003, 4:841-853.
Ross, D. N., "Aortic Valve Surgery," Guy's Hospital, London, 1968, pp. 192-197.
Rousseau, E. P. M. et al., "A Mechanical Analysis of the Closed Hancock Heart Valve Prosthesis," Journal of Biomechanics, 1998, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, M.D., J. Bayne, "Experience with New Retrieval Forceps for Foreign Body Removal in the Vascular, Urinary, and Biliary Systems," Radiology 1990; 176:535-538.
Serruys, P.W., et al., "Stenting of Coronary Arteries. Are we the Sorcerer's Apprentice?," European Heart Journal (1989) 10, 774-782, pp. 37-45, Jun. 13, 1989.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Tofeig, M. et al., "Transcatheter Closure of a Mid-Muscular Ventricular Septal Defect with an Amplatzer VSD Occluder Device," Heart, 1999, 81:438-440.
Uchida, Barry T., et al., "Modifications of Gianturco Expandable Wire Stents," AJR:150, May 1988, Dec. 3, 1987, pp. 1185-1187.
US 9,155,620, 10/2015, Gross et al. (withdrawn)
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.
Webb, J. G. et al., "Percutaneous Aortic Valve Implantation Retrograde from the Femoral Artery," Circulation, 2006, 113:842-850.
Wheatley, M.D., David J., "Valve Prostheses," Rob & Smith's Operative Surgery, Fourth Edition, pp. 415-424, ButtenNorths 1986.
Yoganathan, A. P. et al., "The Current Status of Prosthetic Heart Valves," In Polymetric Materials and Artificial Organs, Mar. 20, 1983, pp. 111-150, American Chemical Society.
Christianson et al., U.S. Appl. No. 15/626,607, filed Jun. 19, 2017, titled: Prosthetic Mitral Valves And Apparatus And Methods For Delivery Of Same.
Kovalsky et al., U.S. Appl. No. 62/137,384, filed Mar. 24, 2015, titled "Apparatus And Methods For Delivery Of A Prosthetic Mitral Valve".
Kovalsky et al., U.S. Appl. No. 62/187,896, filed Jul. 2, 2015, titled "Apparatus And Methods For Delivery Of A Prosthetic Mitral Valve".
Vidlund et al., U.S. Appl. No. 61/935,899, filed Feb. 5, 2014, titled "Transfemoral Delivery Of Prosthetic Mitral Valve".
Vidlund et al., U.S. Appl. No. 62/100,548, filed Jan. 7, 2015, titled "Apparatus And Methods For Transfemoral Delivery Of Prosthetic Mitral Valve".
Vidlund et al., U.S. Appl. No. 62/532,152, filed Jul. 13, 2017, titled "Prosthetic Heart Valves And Apparatus And Methods For Delivery Of Same".
Vidlund et al., U.S. Appl. No. 62/532,659, filed Jul. 14, 2017, titled "Prosthetic Heart Valves And Apparatus And Methods For Delivery Of Same".

\* cited by examiner

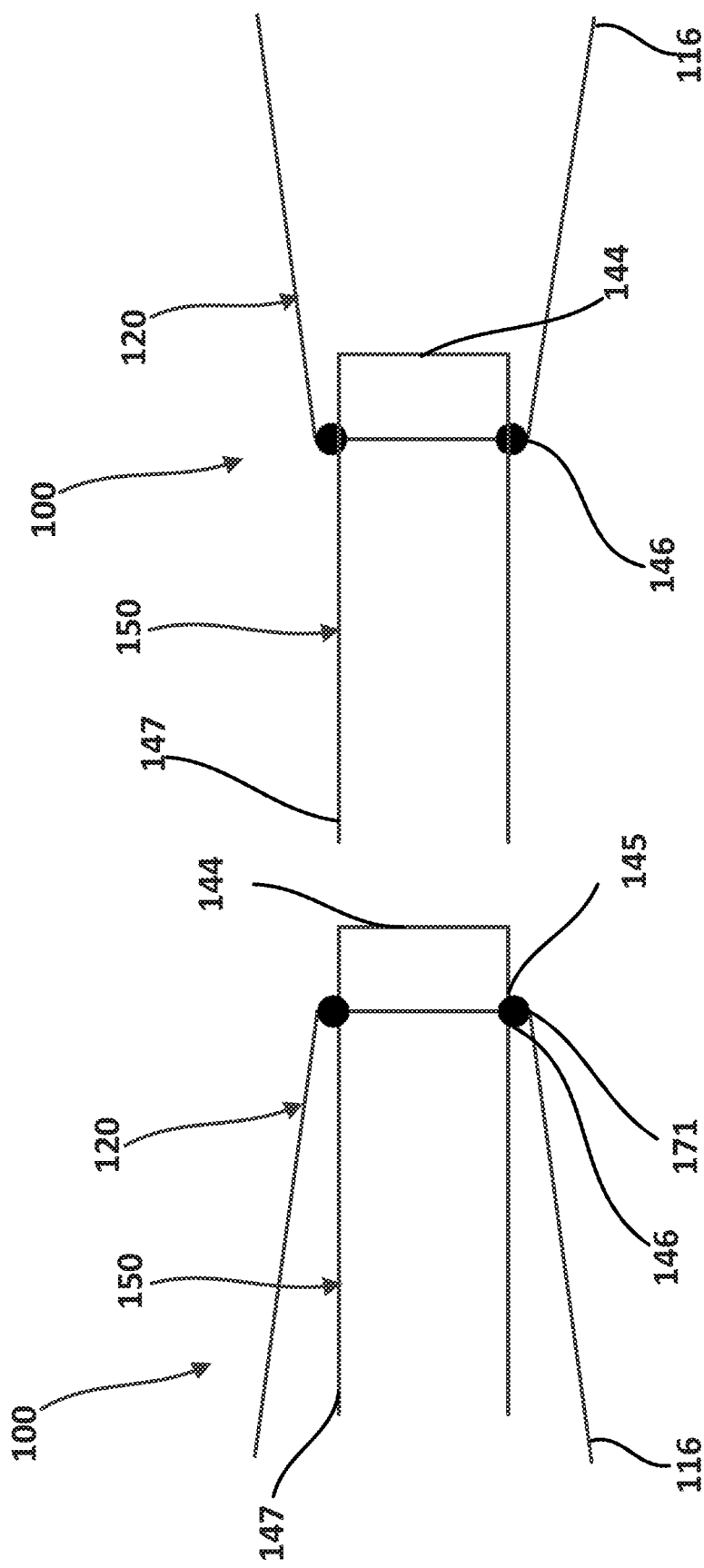

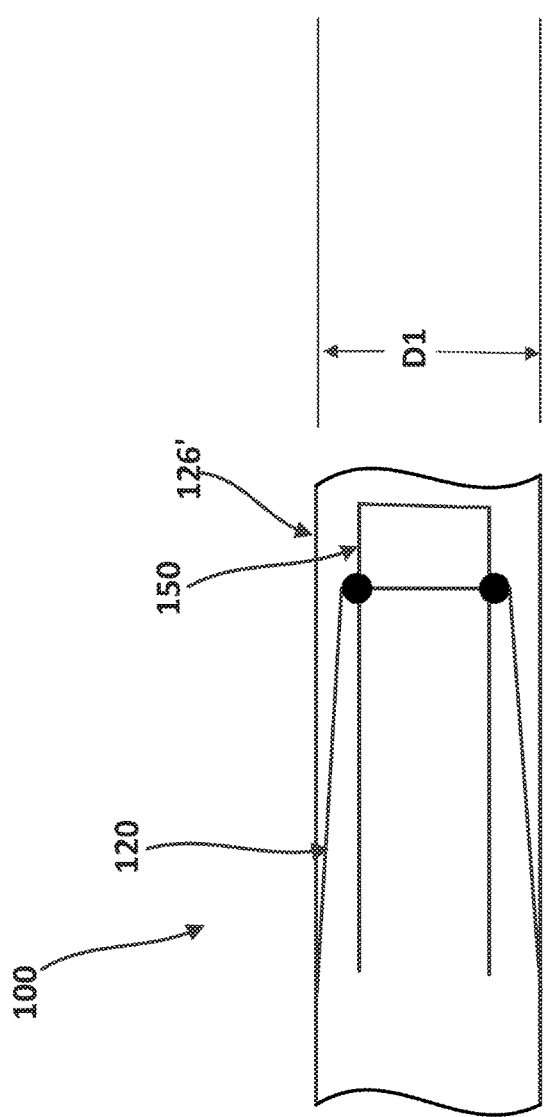
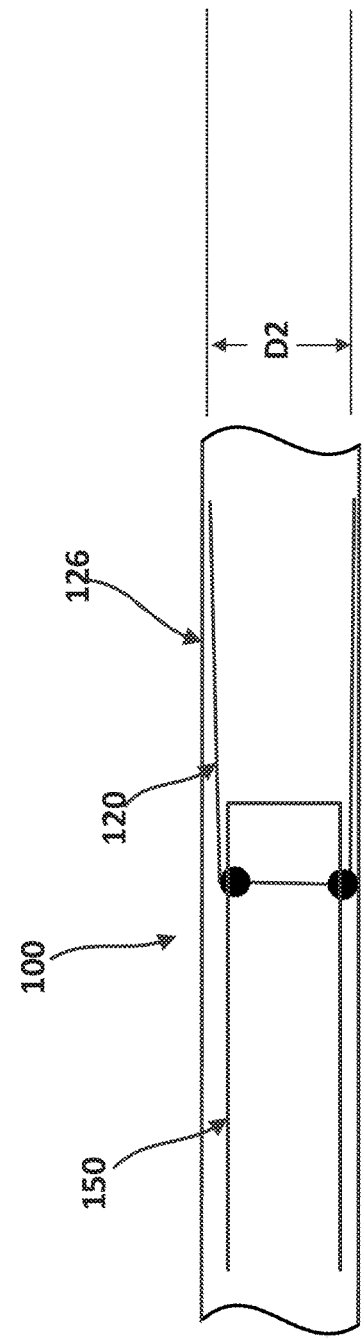

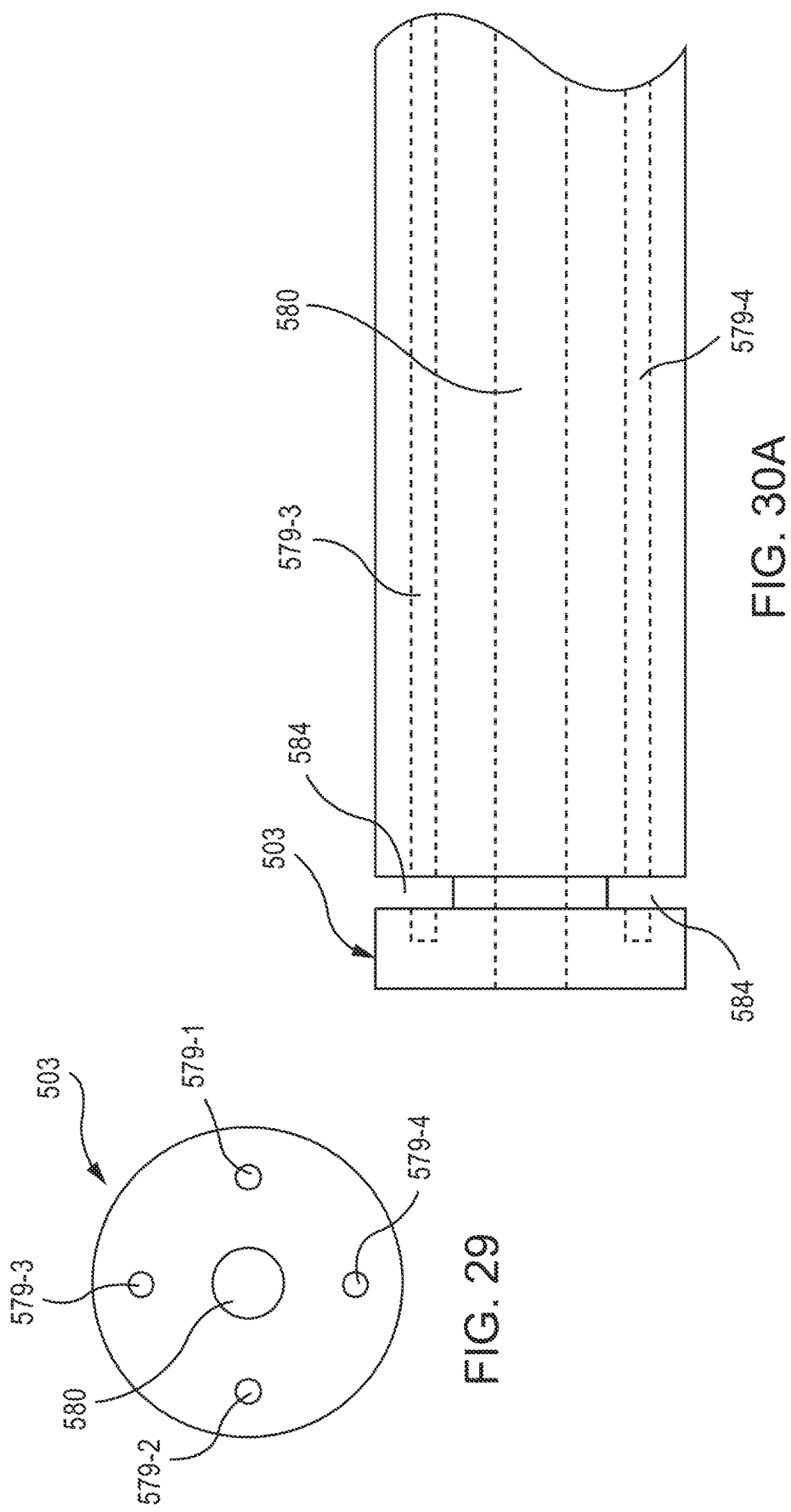

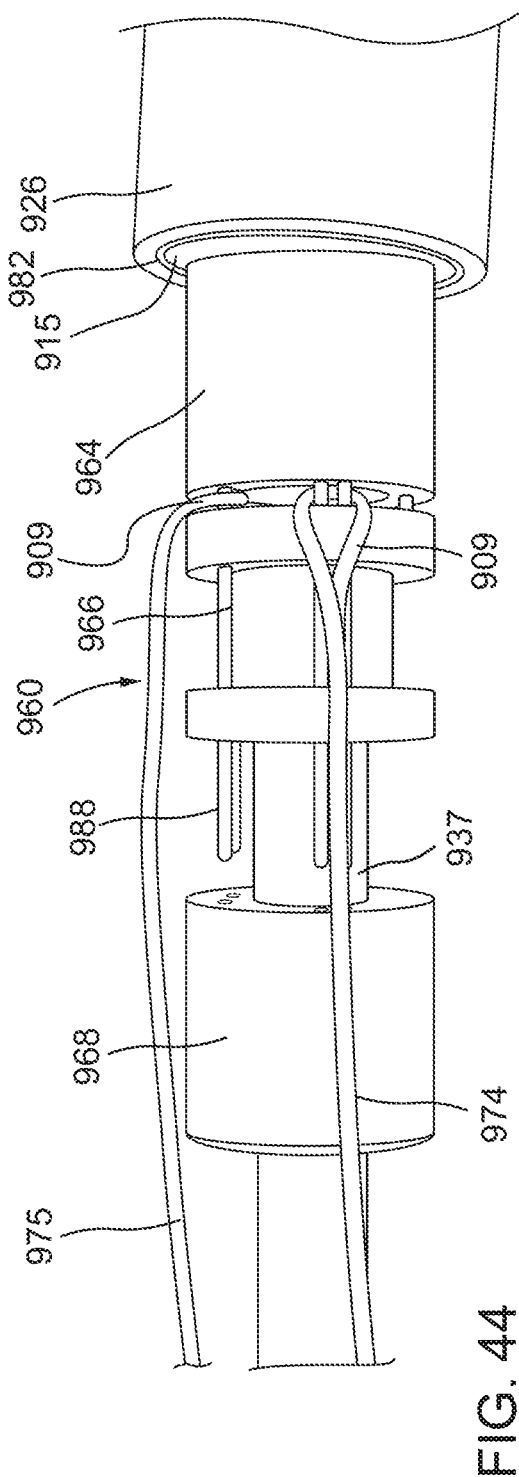
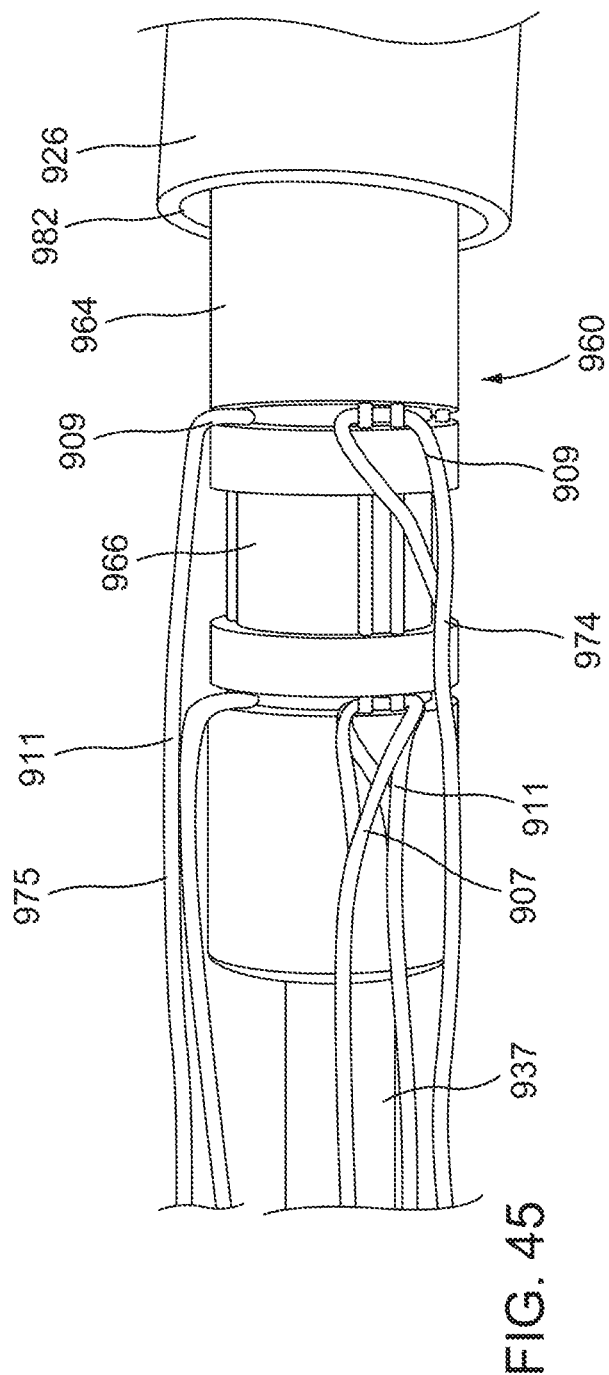

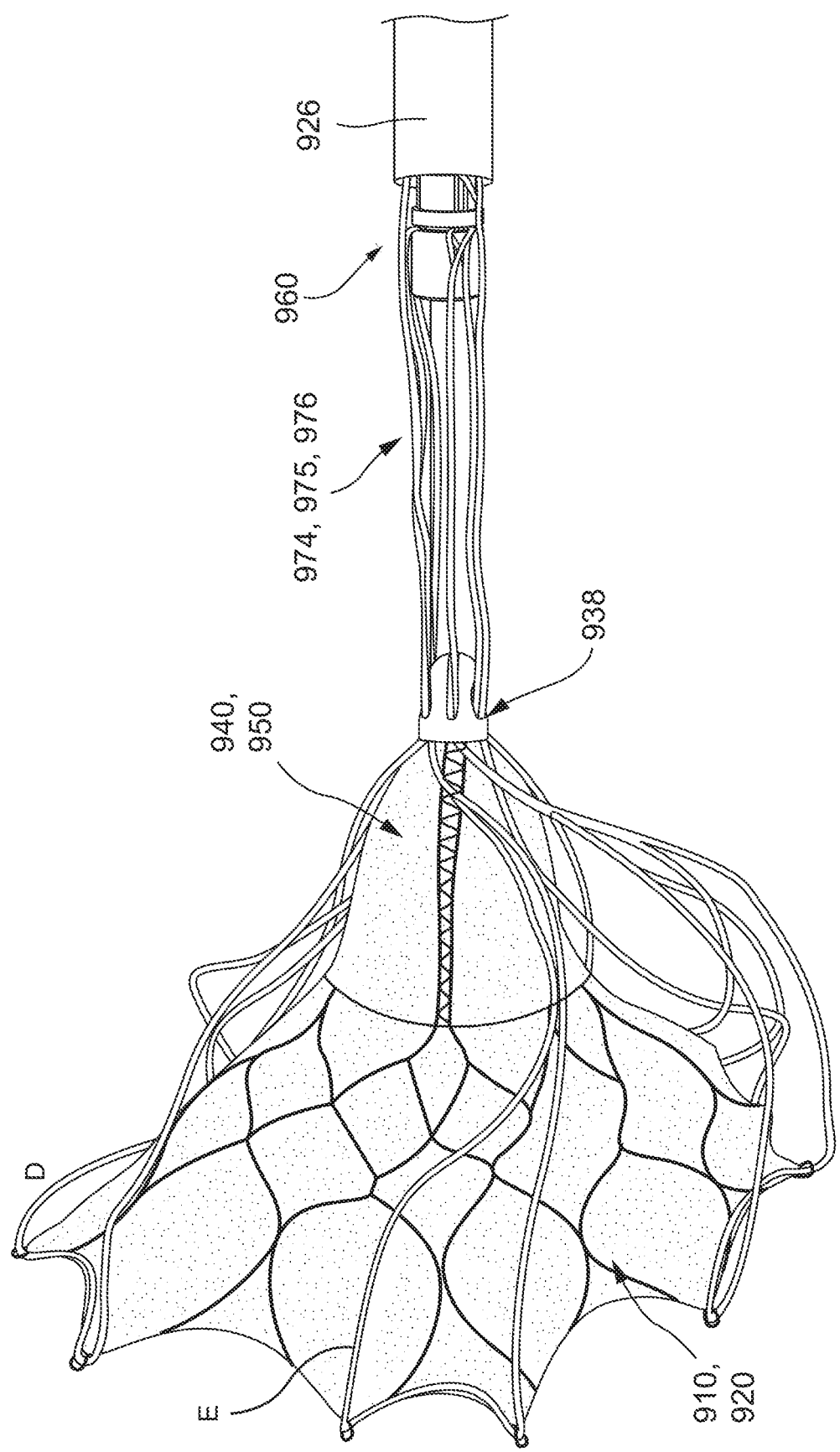

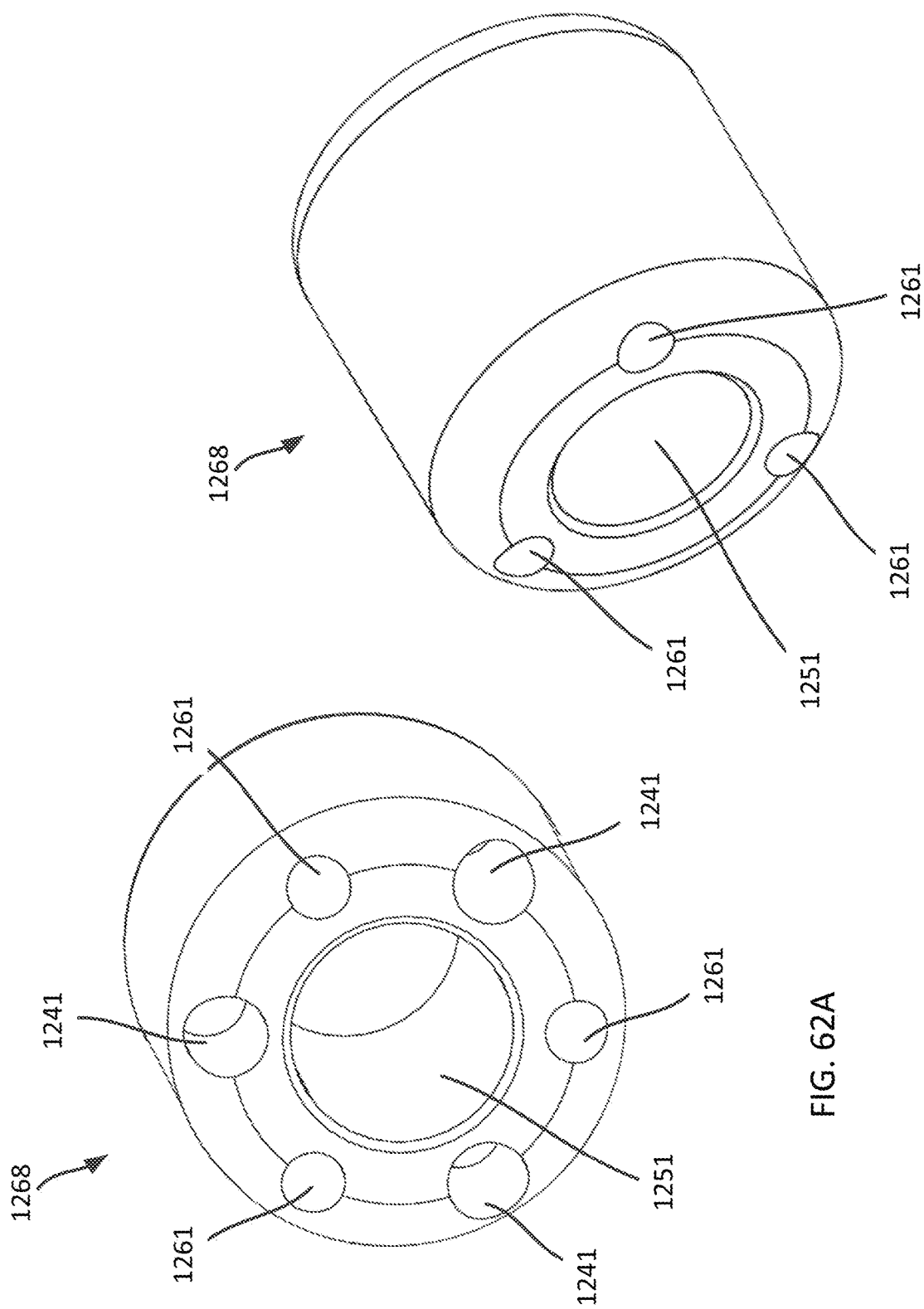

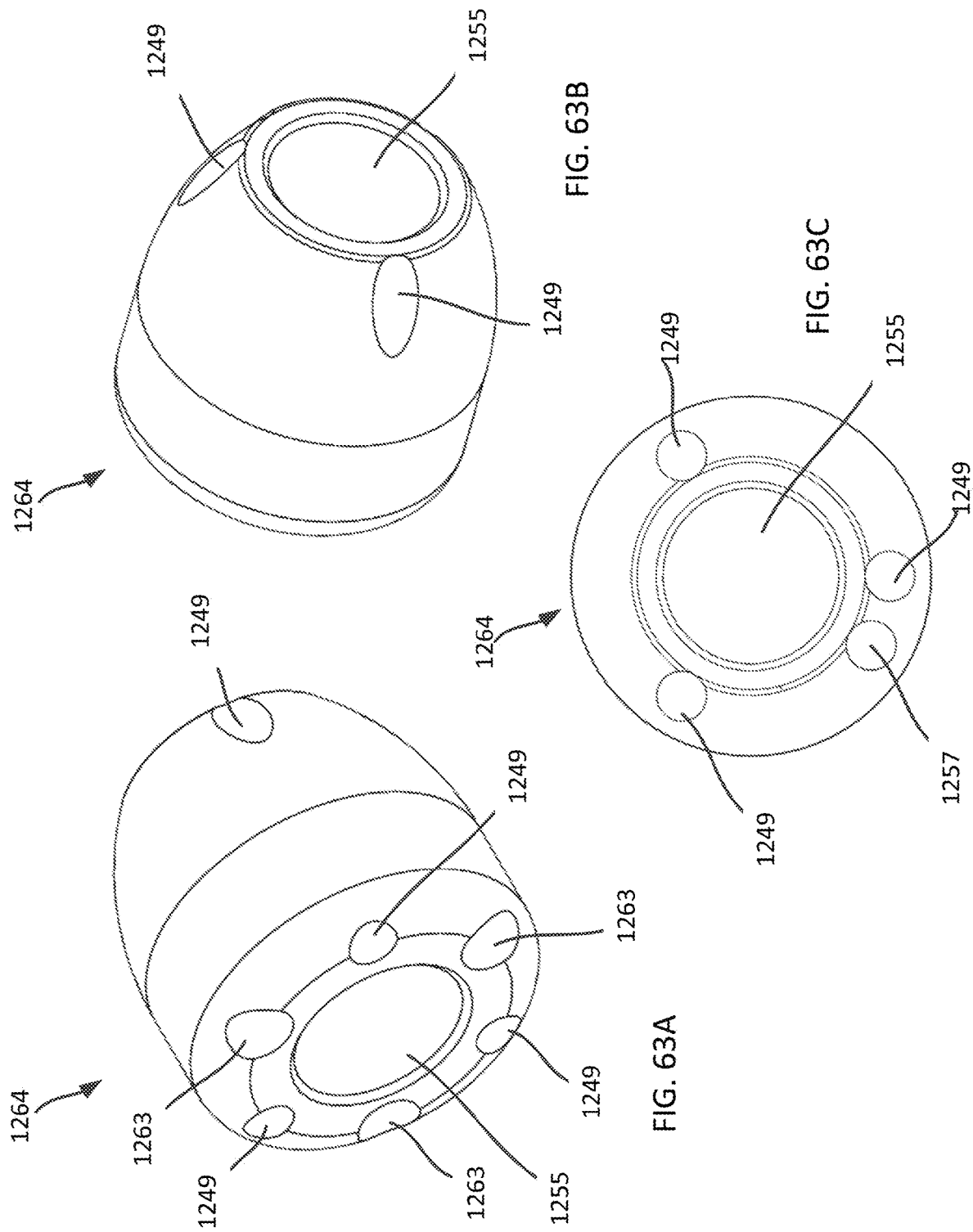

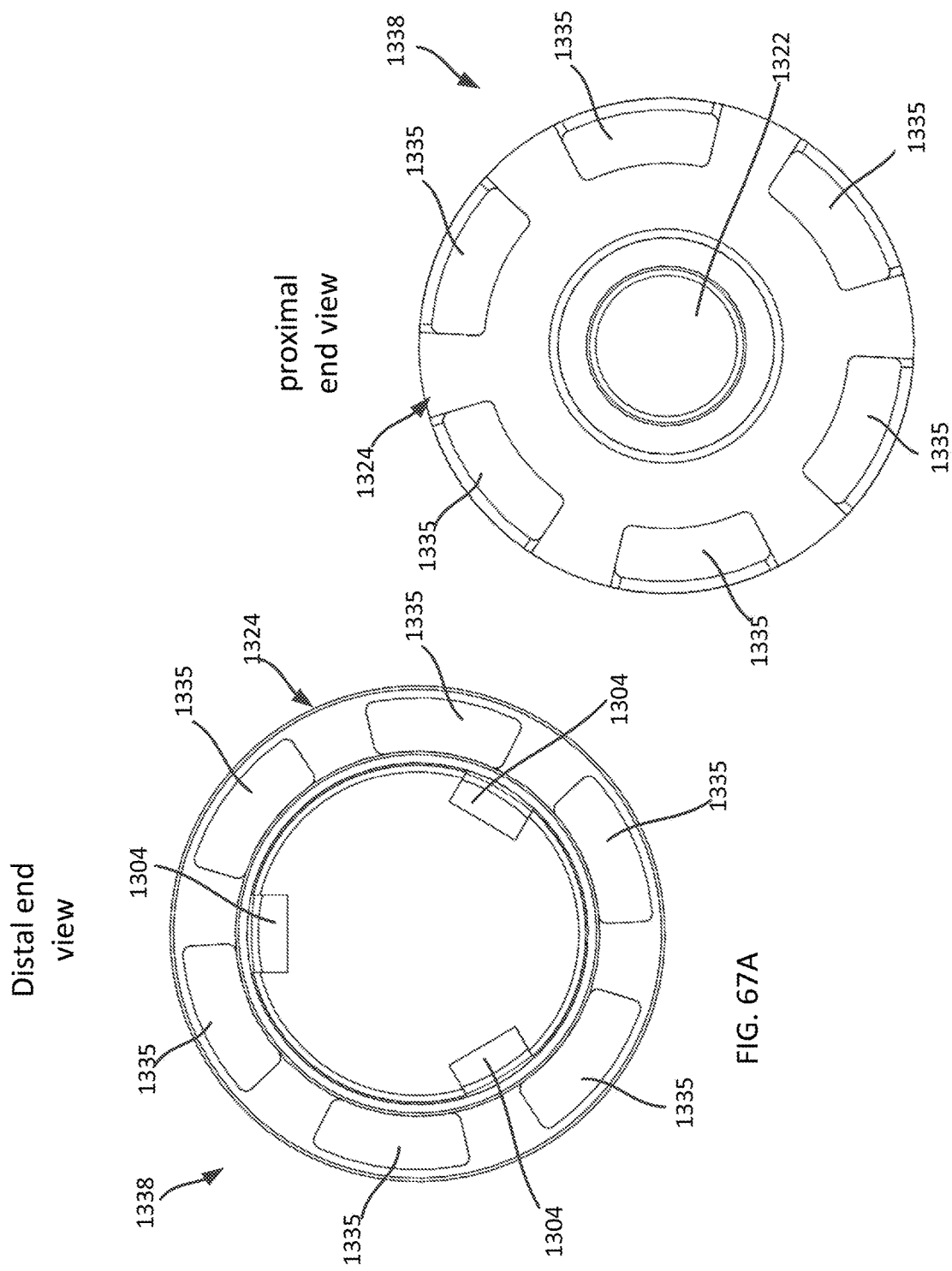

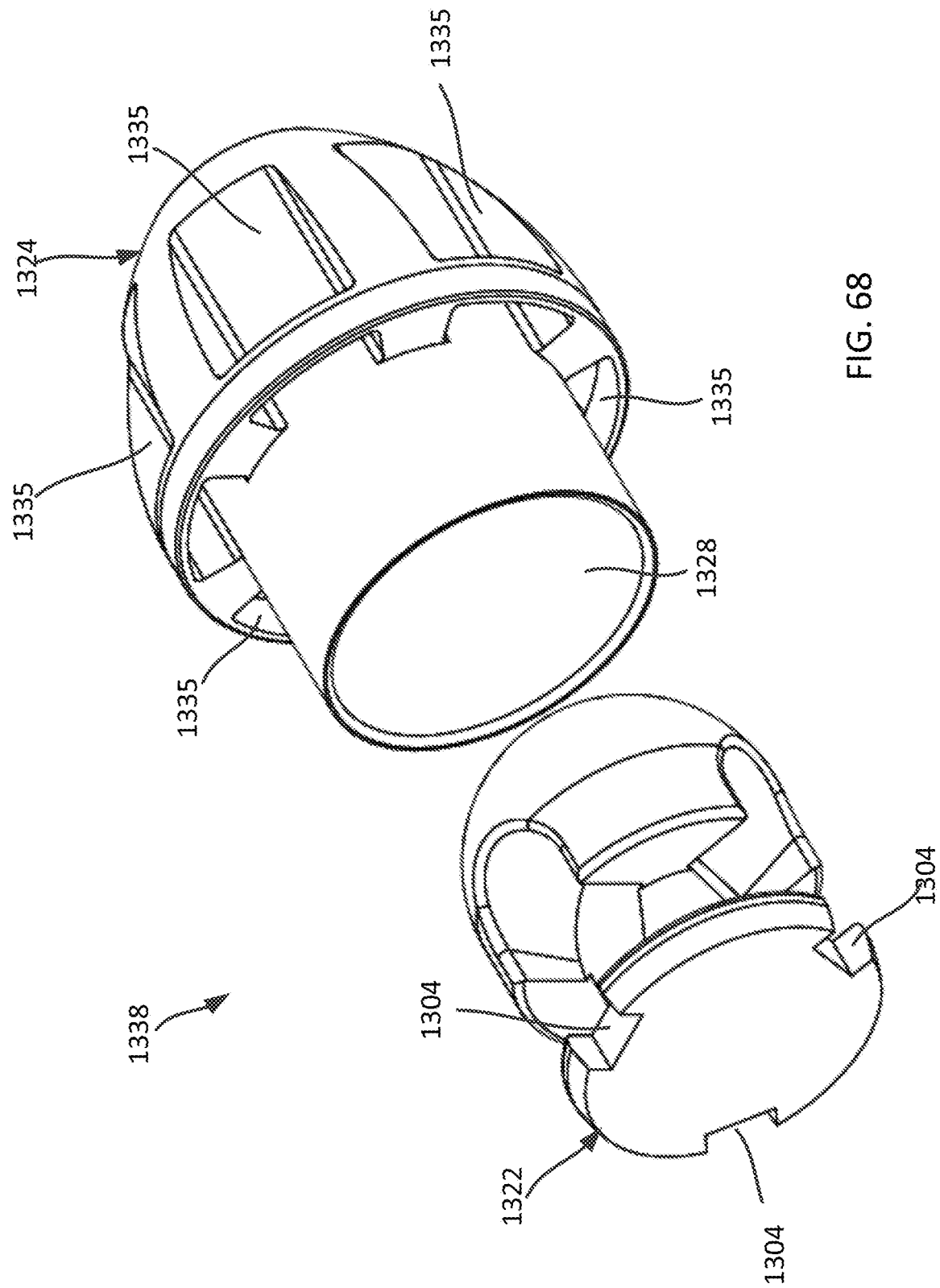

PROSTHETIC HEART VALVES AND APPARATUS AND METHODS FOR DELIVERY OF SAME

CROSS-REFERENCE TO RELATED APPLICATIONS

This application is a national phase entry under 35 U.S.C. § 371 of International Application No. PCT/US2018/041867 filed Jul. 12, 2018, published in English, which claims priority to and the benefit of U.S. Provisional Patent application No. 62/532,152, entitled "Prosthetic Heart Valves and Apparatus and Methods for Delivery of Same," filed Jul. 13, 2017 and U.S. Provisional Patent application No. 62/532,659, entitled "Prosthetic Heart Valves and Apparatus and Methods for Delivery of Same," filed Jul. 14, 2017, the entire disclosures of which are all incorporated herein by reference in their entireties.

This application is related to U.S. patent application Ser. No. 15/626,607, filed on Jun. 19, 2017, entitled "Prosthetic Mitral Valves and Apparatus and Methods for Delivery of Same," which is a continuation of International Application No. PCT/US2016/012305, filed on Jan. 6, 2016, which claims priority to and is a continuation-in-part of International Application No. PCT/US15/14572, entitled "Apparatus and Methods for Transfemoral Delivery of Prosthetic Valve," filed Feb. 5, 2015, which claims priority to and the benefit of U.S. Provisional Patent Application Ser. No. 61/935,899, entitled "Transfemoral Delivery of Prosthetic Mitral Valve," filed Feb. 5, 2014, and U.S. Provisional Patent Application No. 62/100,548, entitled "Apparatus and Methods for Transfemoral Delivery of Prosthetic Mitral Valve," filed Jan. 7, 2015. The disclosure of each of the foregoing applications is incorporated herein by reference in its entirety.

International Application No. PCT/US2016/012305 also claims priority to and the benefit of U.S. Provisional Patent Application No. 62/100,548, entitled "Apparatus and Methods for Transfemoral Delivery of Prosthetic Mitral Valve," filed Jan. 7, 2015. The disclosure of each of the foregoing applications is incorporated herein by reference in its entirety.

International Application No. PCT/US2016/012305 also claims priority to and the benefit of U.S. Provisional Patent Application Ser. No. 62/187,896, entitled "Apparatus and Methods for Delivery of a Prosthetic Mitral Valve," filed Jul. 2, 2015, and U.S. Provisional Patent Application Ser. No. 62/137,384, entitled "Apparatus and Method for Delivery of a Prosthetic Mitral Valve," filed Mar. 24, 2015. The disclosure of each of the foregoing applications is incorporated herein by reference in its entirety.

BACKGROUND

Embodiments are described herein that relate to devices and methods for use in the delivery and deployment of prosthetic valves, and particularly to devices and methods for prosthetic heart valves that provide for delivery of the prosthetic heart valves to within a heart of a patient in an inverted configuration.

Prosthetic heart valves can pose particular challenges for delivery and deployment within a heart. Valvular heart disease, and specifically, aortic and mitral valve disease is a significant health issue in the United States (US); annually approximately 90,000 valve replacements are conducted in the US. Traditional valve replacement surgery involving the orthotopic replacement of a heart valve is considered an "open heart" surgical procedure. Briefly, the procedure necessitates surgical opening of the thorax, the initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated to the procedure largely due to the necessity for extra-corporeal circulation. Further, open heart surgery is often poorly tolerated in elderly patients. Thus, elimination of the extra-corporeal component of the procedure could result in reduction in morbidities and cost of valve replacement therapies could be significantly reduced.

While replacement of the aortic valve in a transcatheter manner is the subject of intense investigation, lesser attention has been focused on the mitral valve. This is in part reflective of the greater level of complexity associated to the native mitral valve apparatus, and thus, a greater level of difficulty with regards to inserting and anchoring the replacement prosthesis. A need exists for delivery devices and methods for transcatheter mitral valve replacements.

Some known delivery methods include delivering a prosthetic mitral valve through an apical puncture site. In such a procedure, the valve is placed in a compressed configuration within a lumen of a delivery catheter of, for example, 34-36 Fr (i.e. an outer diameter of about 11-12 mm). Delivery of a prosthetic valve to the atrium of the heart can be accomplished, for example, via a transfemoral approach, transatrially directly into the left atrium of the heart or via a jugular approach. In such cases, it is desirable for the prosthetic valve to have a small outer perimeter or profile to allow insertion through a smaller delivery catheter of, for example, 28Fr (i.e. an outer diameter of about 9 mm). Thus, a need exists for prosthetic heart valves that can have a small profile during delivery while still maintaining the size and characteristics needed to perform their desired function within the heart.

A need also exists for devices and methods for delivering and deploying a prosthetic heart valve within a heart, with the valve disposed within a small diameter delivery sheath and then moving the valve to an expanded configuration within the heart.

SUMMARY

Apparatus and methods are described herein for various embodiments of a prosthetic heart valve that can be moved to an inverted configuration for delivery of the prosthetic heart valve to within a patient's heart. In some embodiments, an apparatus includes a prosthetic heart valve that includes an inner frame and an outer frame coupled to the inner frame at multiple coupling joints. The prosthetic valve is movable between a first configuration and a second configuration. The multiple coupling joints are configured to allow the outer frame to be moved between a first position relative to the inner frame and a second position relative to inner frame in which the outer frame is inverted relative to the inner frame. The prosthetic valve is in the first configuration when the outer frame is in the first position, and in the second configuration when the outer frame is in the second position.

In some embodiments, an apparatus includes an outer sheath that defines a lumen, a tube member movably disposed within the lumen of the outer sheath and defining a lumen, a retention device coupled to the tube member, a valve holder movably disposed within a lumen defined by the tube member, and a prosthetic heart valve disposed at least partially within the lumen of the outer sheath. The prosthetic heart valve includes an outer frame coupled to an inner frame and the inner frame is removably coupled to a distal end portion of the valve holder. The outer frame is movable between a first configuration relative to the inner frame and a second configuration relative to the inner frame in which the outer frame is inverted relative to the inner frame. The prosthetic heart valve is disposed within the lumen of the outer sheath and the lumen of the tubular member with the outer frame in the second configuration. A first actuation wire is releasably coupled to a first portion of the outer frame and releasably coupled to the retention device at a first location on the retention device. A second actuation wire is releasably coupled to a second portion of the outer frame and releasably coupled to the retention device at a second location on the retention device.

BRIEF DESCRIPTION OF THE FIGURES

FIGS. 1A and 1B are schematic illustrations of a portion of a prosthetic heart valve, according to an embodiment, shown in a first configuration and a second configuration, respectively.

FIGS. 1C and 1D are schematic illustrations of the portion of the prosthetic heart valve of FIGS. 1A and 1B, respectively, shown disposed within a delivery sheath.

FIG. 29 is a proximal end view of a tube member of the delivery system of FIG. 27.

FIG. 30A is a side view of a portion of the tube member of FIG. 29.

FIG. 44 is a side view of a portion of the delivery system of FIG. 42 shown in a second configuration and with actuation wires coupled thereto.

FIG. 45 is a side view of a portion of the delivery system of FIG. 42 shown in a third configuration and with actuation wires coupled thereto.

FIG. 46 is a side view of a portion of the delivery system of FIG. 42 shown with a prosthetic valve coupled to the actuation wires in an inverted configuration and partially expanded configuration.

FIG. 62A is a perspective proximal end view and FIG. 62B is a perspective distal end view of a distal retention member of the retention device of FIG. 59.

FIG. 63A is a perspective distal end view, FIG. 63B is a perspective proximal end view, and FIG. 63C is a proximal end view of a proximal retention member of the retention device of FIG. 59.

FIG. 67A is a distal end view and FIG. 67B is a proximal end view of the valve holder of FIG. 65.

FIG. 68 is an exploded perspective view of the valve holder of FIG. 59.

DETAILED DESCRIPTION

Figure 2B:
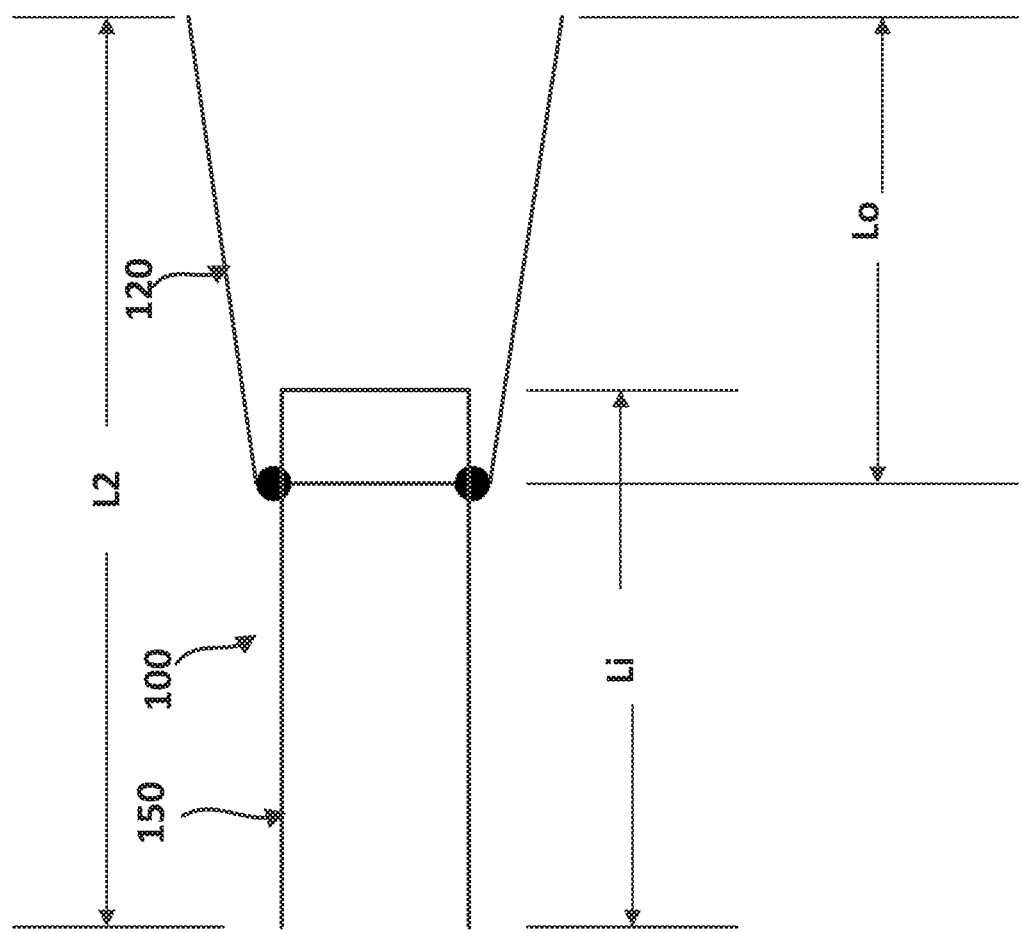
FIGS. 2A and 2B are schematic illustrations of the portion of a prosthetic heart valve of FIGS. 1A and 1B, shown in the first configuration and the second configuration, respectively.

Apparatus and methods are described herein for prosthetic heart valves, such as prosthetic mitral valves, that can be configured to be moved to an inverted configuration for delivery of the prosthetic valve to within a heart of a patient. As described herein, in some embodiments, a prosthetic valve includes an outer frame that can be inverted relative to an inner frame when the prosthetic valve is in a biased expanded configuration. The prosthetic mitral valve can be formed with, for example, a shape-memory material. After inverting the outer frame, the prosthetic valve can be inserted into a lumen of a delivery sheath such that the prosthetic valve is moved to a collapsed configuration.

The delivery sheath can be used to deliver the prosthetic valve to within a patient's heart using a variety of different delivery approaches for delivering a prosthetic heart valve (e.g., prosthetic mitral valve) where the inverted prosthetic valve would enter the heart through the atrium of the heart. For example, the prosthetic valves described herein can be delivered using a transfemoral delivery approach as described in PCT International Application No. PCT/US15/14572 (the "'572 PCT application") and/or in PCT International Application No. PCT/US16/12305 (the "'305 PCT application"), each disclosure of which is incorporated by reference in its entirety herein, or via a transatrial approach, such as described in U.S. Provisional Patent Application Ser. No. 62/220,704, entitled "Apparatus and Methods for Transatrial Delivery of Prosthetic Mitral Valve," filed Sep. 18, 2015 (the "'704 provisional application"), which is incorporated herein by reference in its entirety. In another example, the prosthetic valves described herein (e.g., an inverted valve as described herein) could be delivered via a transjugular approach, e.g., via the right atrium and through the atrial septum and into the left atrium, as described in U.S. Provisional Patent Application Ser. No. 62/305,678, entitled "Apparatus and Methods for Delivery of Prosthetic Mitral Valve," (the "'678 provisional application") and in U.S. Patent Application Pub. No. 2017/0079790, entitled "Apparatus and Methods for Delivery of Prosthetic Mitral Valve," (the "'790 publication") each incorporated by reference in its entirety herein. The prosthetic valves described herein can also be delivered apically if desired. With a transapical approach, after the delivery sheath has been disposed within the left atrium of the heart, the prosthetic mitral valve is moved distally out of the delivery sheath such that the inverted outer frame reverts and the prosthetic valve assumes its biased expanded configuration. The prosthetic mitral valve can then be positioned within a mitral annulus of the heart.

In some embodiments, an apparatus includes a prosthetic valve that includes an inner frame and an outer frame coupled to the inner frame at multiple coupling joints. The multiple coupling joints are configured to allow the outer frame to be moved relative to inner frame such that the prosthetic valve can be moved between a first configuration and a second configuration. The outer frame and the inner frame collectively define a first length of the prosthetic valve when the prosthetic valve is in the first configuration and a second length of the prosthetic valve when the prosthetic valve is in the second configuration and the second length is greater than the first length. The inner frame has a length that is the same when the prosthetic valve is in both the first configuration and the second configuration.

In some embodiments, an apparatus includes a prosthetic heart valve that includes an inner frame and an outer frame coupled to the inner frame at multiple coupling joints. The prosthetic valve is movable between a first configuration and a second configuration. The multiple coupling joints are configured to allow the outer frame to be moved between a first position relative to the inner frame and a second position relative to inner frame in which the outer frame is inverted relative to the inner frame. The prosthetic valve is in the first configuration when the outer frame is in the first position, and in the second configuration when the outer frame is in the second position.

In some embodiments, an apparatus includes a prosthetic heart valve that includes an inner frame, and an outer frame coupled to the inner frame at multiple coupling joints. The multiple coupling joints are configured to allow the outer frame to be moved relative to inner frame such that the prosthetic valve can be moved between a first configuration and a second configuration. The outer frame has an outer frame coupling portion coupled to the inner frame at multiple coupling joints and an outer frame free end portion. The inner frame has an inner frame coupling portion coupled to the outer frame at the multiple coupling joints. A first end portion and an inner frame free end portion are on an opposite end of the inner frame from the first end portion. The multiple coupling joints are disposed between the outer frame free end portion and the first end portion of the inner frame when the prosthetic valve is in the first configuration. The multiple coupling joints are disposed between the inner frame free end portion and the outer frame free end portion when the prosthetic valve is in the second configuration.

In some embodiments, an apparatus includes a prosthetic heart valve that includes an inner frame coupled to an outer frame at multiple coupling joints. The multiple coupling joints are configured to allow the outer frame to be moved relative to the inner frame such that the prosthetic valve can be moved between a first configuration and a second configuration. The outer frame has an outer frame coupling portion coupled to the inner frame at the multiple coupling joints and an outer frame free end portion. The inner frame has an inner frame coupling portion coupled to the outer frame at the multiple coupling joints and an inner frame free end portion. The outer frame free end portion and the inner frame free end portion each open in the same direction when the prosthetic valve is in the first configuration. The outer frame free end portion and the inner frame free end portion open in opposite directions when the prosthetic valve is in the second configuration.

In some embodiments, an apparatus includes a delivery sheath that defines a lumen, a valve holder movably disposable within the lumen of the delivery sheath and a prosthetic heart valve disposed at least partially within the lumen of the delivery sheath in a collapsed configuration. The prosthetic heart valve includes an outer frame coupled to an inner frame and the inner frame is removably coupled to a distal end portion of the valve holder. The outer frame is movable between a first configuration relative to the inner frame and a second configuration relative to the inner frame in which the outer frame is inverted relative to the inner frame. The prosthetic heart valve is disposed within the lumen of the delivery sheath with the outer frame in the second configuration. A first actuation wire is releasably coupled to a first portion of the outer frame and a second actuation wire is releasably coupled to a second portion of the outer frame. Each of the first actuation wire and the second actuation wire have a first portion extending proximally from the outer frame and a second portion extending proximally from the outer frame. The first portion and the second portion of each of the first actuation wire and the second actuation wire are configured to be pulled proximally to urge the outer frame from the second configuration towards the first configuration relative to the inner frame.

In some embodiments, an apparatus includes an outer sheath that defines a lumen, a tube member movably disposed within the lumen of the outer sheath and defining a lumen, a retention device coupled to the tube member, a valve holder movably disposed within the lumen of the outer sheath and within a lumen defined by the tube member, and a prosthetic heart valve disposed at least partially within the lumen of the outer sheath. The prosthetic heart valve includes an outer frame coupled to an inner frame and the inner frame is removably coupled to a distal end portion of the valve holder. The outer frame is movable between a first configuration relative to the inner frame and a second configuration relative to the inner frame in which the outer frame is inverted relative to the inner frame. The prosthetic heart valve is disposed within the lumen of the outer sheath and the lumen of the inner sheath with the outer frame in the second configuration. A first actuation wire is releasably coupled to a first portion of the outer frame and releasably coupled to the retention device at a first location on the retention device. A second actuation wire is releasably coupled to a second portion of the outer frame and releasably coupled to the retention device at a second location on the retention device.

In some embodiments, a method includes inserting a distal end portion of a delivery sheath into a left atrium of a heart. The delivery sheath having a prosthetic mitral valve disposed within a lumen of the delivery sheath and the prosthetic mitral valve has an outer frame coupled to an inner frame such that the outer frame can be moved between a first position relative to the inner frame and a second position relative to the inner frame in which the outer frame is inverted relative to the inner frame. The prosthetic valve is disposed within the lumen of the delivery sheath with the outer frame in the second position relative to the inner frame. The prosthetic mitral valve is moved distally out of the delivery sheath causing the outer frame of the prosthetic mitral valve to revert back to the first position relative to the inner frame such that the prosthetic mitral valve at least partially assumes a biased expanded configuration. The prosthetic mitral valve is positioned within a mitral annulus of the heart.

In some embodiments, an apparatus includes an outer sheath that defines a first lumen and is configured to receive a prosthetic heart valve in a compressed configuration and a tube member movably disposed within the first lumen of the outer sheath and defining a second lumen. A valve holder having at least a portion of which movably disposed within the second lumen of the tube member. The valve holder is configured to be releasably coupled to a prosthetic heart valve during delivery of the prosthetic heart valve to a heart. A retention device is coupled to a distal end portion of the tube member and includes a proximal retention member defining a first opening, a center retention member including a first pin and defining a second opening, and a distal retention member including a second pin. The proximal retention member is fixedly coupled to the tube member and the center retention member is axially movable relative to the proximal retention member between a first position in which the first pin is spaced from the proximal retention member and a second position in which the first pin is disposed within the first opening of the proximal retention member. The distal retention member is axially movable relative to the center retention member between a first position in which the second pin is disposed at a spaced distance from the center retention member and a second position in which the second pin is disposed within the second opening. The retention device can be actuated to secure an actuation wire releasably coupled to a prosthetic heart valve to the retention device when at least one of the center retention member is moved to its second positon and the first pin secures a first loop of the actuation wire to the retention member or the distal retention member is moved to its second position and the second pin secures a second loop of the actuation wire to the retention device.

In some embodiments, a method includes placing a first loop of an actuation wire over a first pin of a retention device of a prosthetic heart valve delivery device. The retention device includes a proximal retention member that defines a first opening, a center retention member that includes the first pin and defines a second opening, and a distal retention member that includes a second pin. A first portion of the actuation wire is passed through a first loop on an outer frame of a prosthetic heart valve and a second portion of the actuation wire is passed through a second loop on the outer frame of the prosthetic heart valve. The first portion of the actuation wire has a second loop disposed on a first end of the actuation wire and the second portion of the actuation wire has a third loop on a second end of the actuation wire. The second loop and the third loop of the actuation wire are placed over the second pin of the retention device. The retention device is actuated to move one of the center retention member and the proximal retention member axially such that the first pin is disposed in the first opening and the first loop of the actuation wire is secured to the retention device. The retention member is actuated again to move the distal retention member axially such that the second pin is disposed in the second opening and the second loop and the third loop of the actuation wire are secured to the retention device. The prosthetic valve is placed within a lumen of a sheath of the delivery device.

In some embodiments, a method includes inserting a distal end portion of a delivery sheath of a valve delivery device into a left atrium of a heart, when the delivery sheath has a prosthetic mitral valve disposed within a lumen of the delivery sheath. The prosthetic mitral valve has an outer frame coupled to an inner frame and the outer frame is inverted relative to the inner frame. The prosthetic heart valve is releasably coupled to a retention device that includes a proximal retention member defining a first opening, a center retention member including a first pin and defining a second opening, and a distal retention member including a second pin. An actuation wire is coupled to the prosthetic heart valve and includes a first loop secured to the retention device with the first pin and a second loop secured to the retention device with the second pin. The prosthetic mitral valve is moved distally out the distal end portion of the delivery sheath. The retention device is moved proximally such that the actuation wire pulls the outer frame of the prosthetic heart valve proximally and the outer frame is reverted relative to the inner frame. The retention device is actuated such that the distal retention member moves axially relative to the center retention member and the second pin releases the second loop of the actuation wire. After actuating the retention device, the retention device is moved proximally such that the actuation wire is pulled proximally and is uncoupled from the prosthetic heart valve, allowing the outer frame of the prosthetic heart valve to move to a biased expanded configuration. The prosthetic heart valve is then positioned within a mitral valve annulus of the heart.

In some embodiments, an apparatus includes a prosthetic heart valve that includes an inner frame and an outer frame coupled to the inner frame. The outer frame includes a body portion and a cuff portion and is configured to be moved relative to the inner frame such that the prosthetic valve can be moved between a first biased expanded configuration in which the outer frame is disposed substantially surrounding the inner frame and a second configuration in which the outer frame is inverted relative to the inner frame such that a free end portion of the outer frame opens in an opposite direction than a free end portion of the inner frame. The cuff portion includes a first portion disposed at a transverse angle relative to the body portion and a second portion extending at a transverse angle relative to the first portion of the cuff portion when the prosthetic heart valve is in the biased expanded configuration.

In some embodiments, an actuation wire for use in delivery of a prosthetic heart valve to a heart of a subject includes a first elongate strand having a first end and a second end, a second elongate strand having a first end and a second end. A first loop is disposed at the first end of the first elongate strand, a second loop is disposed at a first end of the second elongate strand, and a third loop is disposed between the second end of the first elongate strand and the second end of the second elongate strand. The first loop, the second loop and the third loop are each configured to be releasably pinned to a delivery device and the first elongate strand and the second elongate strand are each configured to be releasably coupled to the prosthetic heart valve.

Figure 2A:
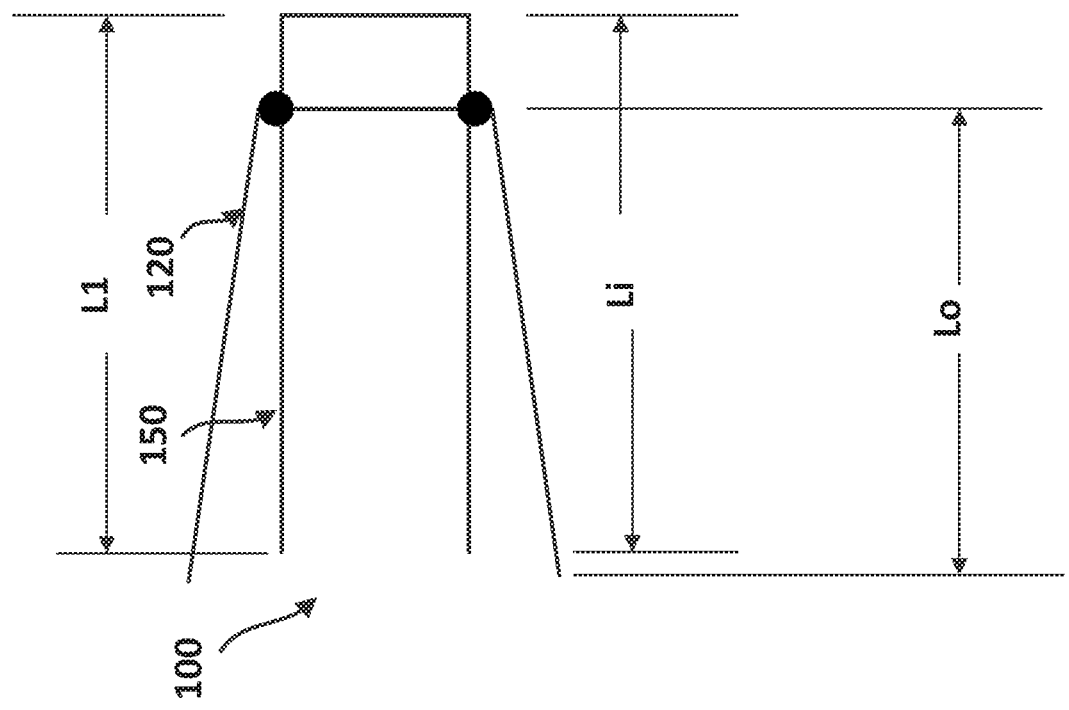

FIGS. 1A and 1B are schematic illustrations of a portion of a prosthetic heart valve 100, according to an embodiment, shown in a first configuration and a second configuration respectively, and FIGS. 1C and 1D illustrate the portions of the prosthetic heart valve 100 of FIGS. 1A and 1B, respectively, shown disposed within a lumen of a delivery sheath 126. FIGS. 2A and 2B illustrate a portion of the prosthetic heart valve 100 of FIGS. 1A and 1B, respectively, and show length dimensions for the prosthetic heart valve in each of the first configuration and the second configuration. The prosthetic heart valve 100 (also referred to herein as "prosthetic valve" or "valve") can be, for example, a prosthetic mitral valve. The valve 100 includes an outer frame 120 and an inner frame 150. The outer frame 120 and the inner frame 150 are each formed as a tubular structure as described in more detail below with reference to FIGS. 3-15. The outer frame 120 and the inner frame 150 can be coupled together at multiple coupling joints 146 disposed about a perimeter of the inner frame 150 and a perimeter of the outer frame 120 as described in more detail below. The valve 100 can also include other features, such as those described with respect to FIGS. 3-15 below. For illustration purposes, only the inner frame 150 and the outer frame 120 are discussed with respect to FIGS. 1A-2B. The various characteristics and features of valve 100 described with respect to FIGS. 1A-2B can apply to any of the prosthetic valves described here.

The outer frame 120 is configured to have a biased expanded or undeformed shape and can be manipulated and/or deformed (e.g., compressed or constrained) and, when released, return to its original (expanded or undeformed) shape. For example, the outer frame 120 can be formed of materials, such as metals or plastics, which have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used. The inner frame 150 can be formed from a laser-cut tube of Nitinol®. The inner frame 150 can also have a biased expanded or undeformed shape and can be manipulated and/or deformed (e.g., compressed and/or constrained) and, when released, return to its original (expanded or undeformed) shape. Further details regarding the inner frame 150 and the outer frame 120 are described below with respect to valve 200 and FIGS. 3-15.

The valve 100 can be delivered and deployed within a left atrium of a heart using a variety of different delivery approaches including, for example, a transfemoral delivery approach, as described in the '572 PCT application, or a transatrial approach, as described in the '704 provisional application. As described above, in some situations, such as when delivering a prosthetic valve to the heart via a transfemoral or transatrial approach, because of the smaller size of the lumen of the delivery sheath, the size of the prosthetic valve during delivery should be sized accordingly. Thus, it is desirable to have a prosthetic valve that can be reconfigured between a biased expanded configuration for implantation in the heart (e.g., within a native mitral annulus) and a delivery configuration that has a smaller outer perimeter or profile to allow for delivery within the lumen of the delivery sheath. The prosthetic valve 100 and the embodiments of a prosthetic valve described herein can be constructed and formed to achieve these desired functions and characteristics.

More specifically, the valve 100 can have a biased expanded configuration (as shown in FIGS. 1A and 2A), an inverted configuration (as shown in FIGS. 1B and 2B), and a compressed or collapsed configuration (as shown in FIGS. 1C and 1D). The expanded configuration allows the valve 100 to function when implanted within the heart. The valve 100 can be moved to the inverted configuration and the compressed or collapsed configuration for delivery of the valve 100 to the heart of a patient.

To enable the valve 100 to be moved to the inverted configuration, the outer frame 120 can be coupled to the inner frame 150 in such a manner to allow the outer frame 120 to move relative to the inner frame 150. More specifically, the coupling joints 146 can couple the outer frame 120 to the inner frame 150 in such a manner to allow the outer frame 120 to be moved relative to the inner frame 150. For example, in some embodiments, the coupling joints 146 can be configured to allow the outer frame 120 to rotate about the coupling joint 146 relative to the inner frame 150. In some embodiments, coupling joints can provide a pivotal coupling between the outer frame 120 and the inner frame 150. In some embodiments, the coupling joints can provide a flexible attachment between the outer frame 120 and the inner frame 150. The coupling joints 146 can be a variety of different types and configurations as described herein with reference to the various embodiments of a prosthetic valve. For example, the coupling joints 146 can include a living hinge, a flexible member, sutures, a suture wrapped through an opening, a pin or tab inserted through an opening or any combinations thereof.

To move the valve 100 from the expanded configuration (FIG. 1A) to the inverted configuration (FIG. 1B), the outer frame 120 is moved to a prolapsed or inverted configuration relative to the inner frame 150, as shown in FIGS. 1B, 1D and 2B, by moving (e.g., rotating, pivoting, flexing) the outer frame 120 about the coupling joints 146. The elastic or superelastic structure of outer frame 120 of valve 100 also allows the outer frame 120 to be moved to, and disposed in, the prolapsed or inverted configuration relative to the inner frame 150. To move the outer frame 120 to the inverted configuration relative to the inner frame 150, the outer frame 120 is folded or inverted distally (to the right in FIG. 1B) relative to the inner frame 150 via the coupling joints 146. As shown in FIGS. 1A and 2A, the outer frame 120 is in a first position relative to the inner frame 150 prior to being inverted in which an open or free end portion 116 (also referred to the atrium portion 116 of the outer frame 120) is disposed proximally or to the left of the coupling joints 146 and in the same direction as a free end portion 147 (also referred to as a second end portion of the inner frame) of the inner frame 150. When the outer frame 120 is moved to an inverted configuration (i.e., second position relative to the inner frame 150), the free end portion 116 is disposed distally of the coupling joints 146 (or to the right in FIGS. 1B and 2B) and in an opposite direction as the free end portion 147 of the inner frame 150. Said another way, when the valve 100 is in a biased expanded configuration (e.g., FIG. 1A), the coupling joints 146 are disposed between a first end portion 144 (also referred to as a tether coupling portion) of the inner frame 150 and the free end portion 116 of the outer frame 120. When the valve 100 is in the inverted configuration (e.g., FIG. 1B) (i.e., the outer frame 120 has been moved to an inverted configuration or position), the coupling joints 146 are disposed between the free end portion or second end portion 147 of the inner frame 150 and the free end portion 116 of the outer frame 120.

When in the inverted configuration, an overall length of the valve 100 is increased, but a length of the inner frame 150 and a length of the outer frame 120 remains the same (or substantially the same). For example, as shown in FIGS. 2A and 2B an overall length L1 of the valve 100 in the biased expanded configuration (prior to being inverted as shown in FIG. 2A) is less than the overall length L2 of the valve 100 when in the inverted configuration (FIG. 2B). A length Li of the inner frame 150 and a length Lo of the outer frame 120 is substantially the same (or the same) when the valve 100 is in both the biased expanded configuration and the inverted configuration. In addition, in some instances, depending on the specific configuration of the outer frame, an overall outer perimeter or outer diameter of the valve 100 can be smaller when the valve 100 is in the inverted configuration.

With the valve 100 in the inverted configuration, the valve 100 can be placed within a lumen of the delivery sheath 126 for delivery of the valve 100 to the left atrium of the heart, as shown in FIG. 1D. When placed within the lumen of the delivery sheath 126, the valve 100 is moved to the collapsed or compressed configuration in which the outer diameter or outer perimeter of the valve 100 is reduced. Because the valve 100 is in the inverted configuration, the valve 100 is able to be placed within a smaller delivery sheath 126 than would otherwise be possible. For example, for comparison purposes, FIG. 1C illustrates the valve 100 placed within a lumen of a delivery sheath 126' where the valve 100 has not been moved to an inverted configuration prior to being disposed within the delivery sheath 126'. As shown in FIG. 1C, an outer diameter of the valve 100 is reduced, but not to as small of a diameter as for the valve 100 when placed in a delivery sheath 126 when in the inverted configuration. Thus, in FIG. 1C, the valve 100 has an overall outer perimeter or outer diameter D1 and in FIG. 1D, the valve 100 has an overall outer perimeter or outer diameter D2, which is less than D1.

Thus, by disposing the outer frame 120 in the inverted configuration, the valve 100 can be collapsed into a smaller overall diameter, i.e. placed in a smaller diameter delivery sheath 126, than would be possible if the valve 100 were merely collapsed radially. This is because when the valve is in the biased expanded configuration, the inner frame 150 is nested within an interior of the outer frame 120, and thus the outer frame 120 must be collapsed around the inner frame 150. In some embodiments, the inner frame 150 and the outer frame are disposed concentrically. Whereas in the inverted configuration, the inner frame 150 and the outer frame 120 are arranged axially with respect to each other (i.e., the inner frame is not nested within the outer frame 150), such that the outer frame 120 can be collapsed without needing to accommodate all of the structure of the inner frame 150 inside it. In other words, with the inner frame 150 disposed mostly inside or nested within the outer frame 120, the layers or bulk of the frame structures cannot be compressed to as small a diameter. In addition, if the frames are nested, the structure is less flexible, and therefore, more force is needed to bend the valve, e.g., to pass through tortuous vasculature or to make tight turns in the left atrium after passing through the atrial septum to be properly oriented for insertion into the mitral valve annulus.

Figure 3:
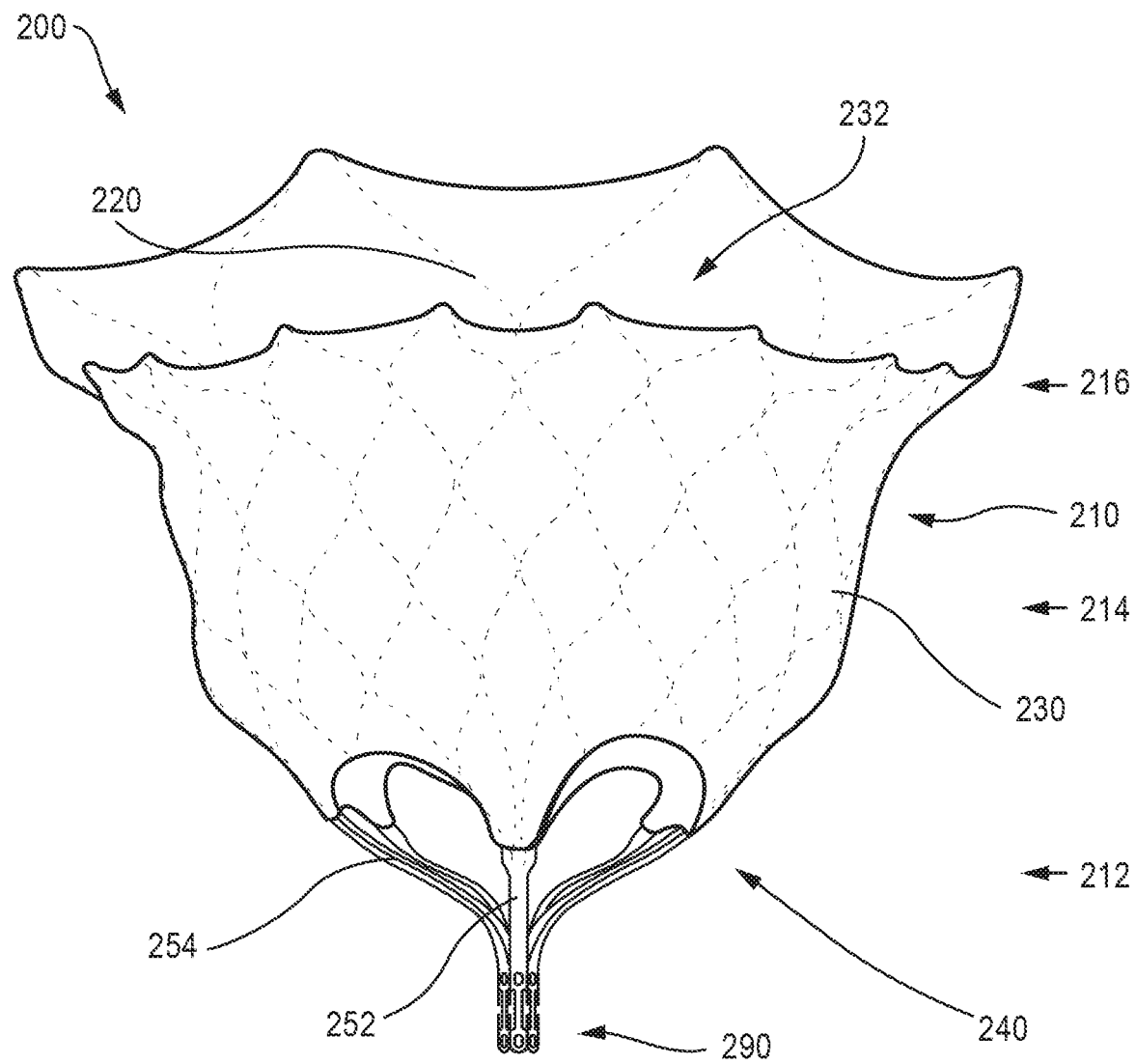
FIGS. 3-5 are front, bottom, and top views of a prosthetic heart valve according to an embodiment.
Figure 4:
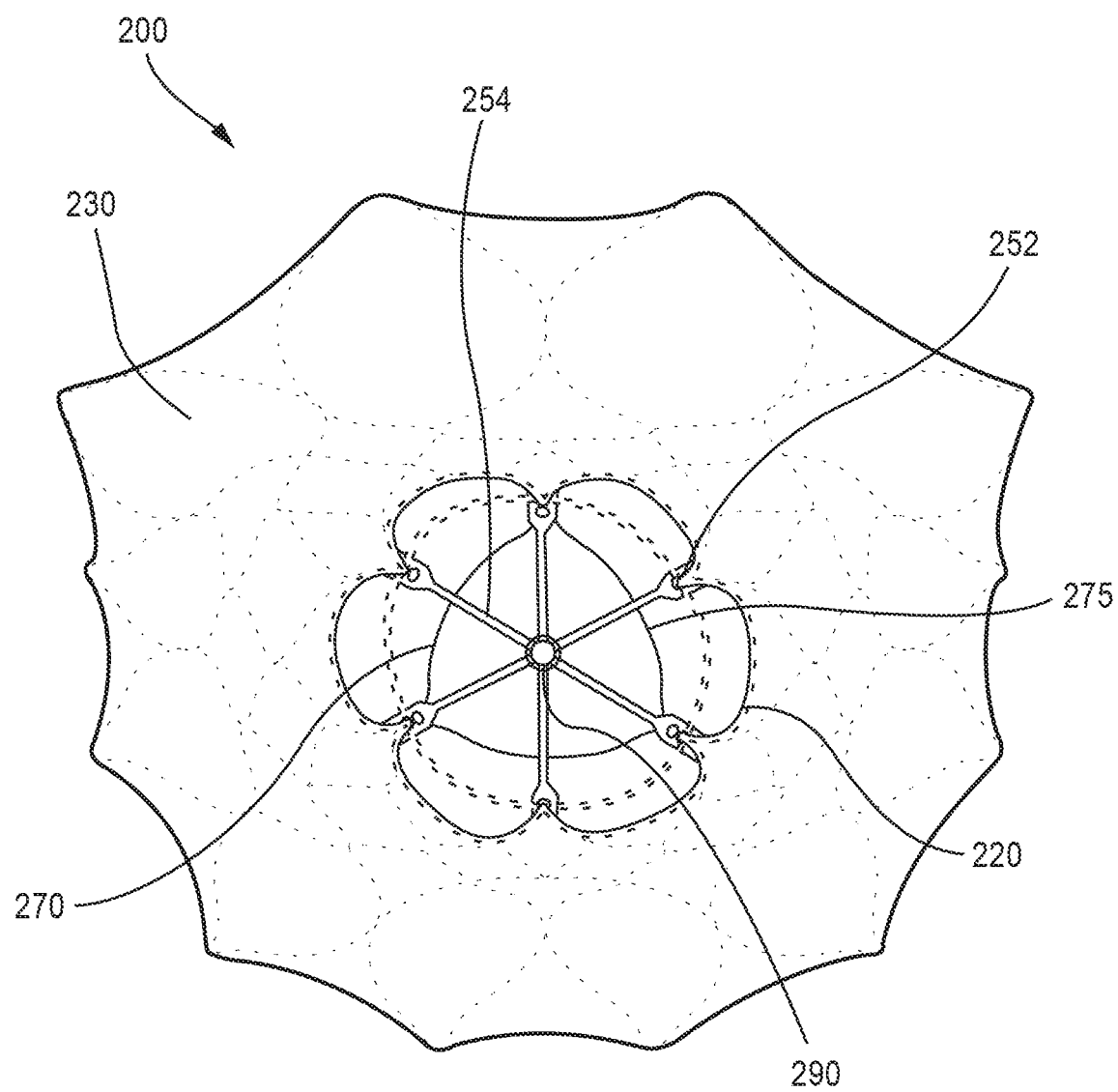
Figure 5:
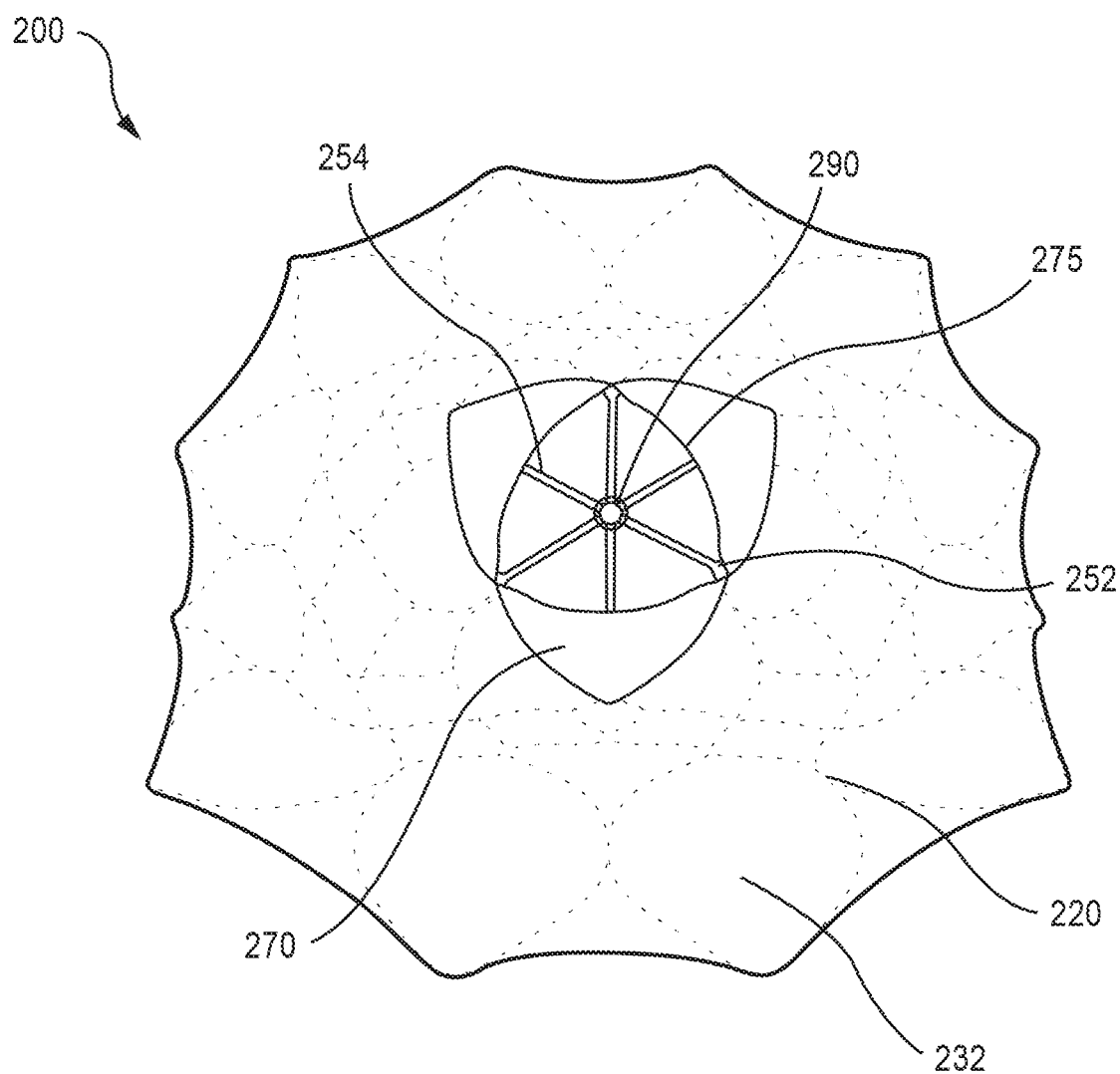

FIGS. 3-14 illustrate another embodiment of a prosthetic heart valve that can be delivered and deployed within a left atrium of a heart using a variety of different delivery approaches including, for example, a transfemoral delivery approach or a transatrial delivery approach. FIGS. 3-5 are front, bottom, and top views, respectively, of a prosthetic heart valve 200 according to an embodiment. Prosthetic heart valve 200 (also referred to herein as "valve" or "prosthetic valve") is designed to replace a damaged or diseased native heart valve such as a mitral valve. Valve 200 includes an outer frame assembly 210 and an inner valve assembly 240 coupled to the outer frame assembly 210.

As shown, outer frame assembly 210 includes an outer frame 220, covered on all or a portion of its outer face with an outer covering 230, and covered on all or a portion of its inner face by an inner covering 232. Outer frame 220 can provide several functions for prosthetic heart valve 200, including serving as the primary structure, as an anchoring mechanism and/or an attachment point for a separate anchoring mechanism to anchor the valve to the native heart valve apparatus, a support to carry inner valve assembly 240, and/or a seal to inhibit paravalvular leakage between prosthetic heart valve 200 and the native heart valve apparatus.

Outer frame 220 has a biased expanded configuration and can be manipulated and/or deformed (e.g., compressed and/or constrained) and, when released, return to its original unconstrained shape. To achieve this, outer frame 220 can be formed of materials, such as metals or plastics that have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used.

As best shown in FIG. 3, outer frame assembly 210 has an upper end (e.g., at the atrium portion 216), a lower end (e.g., at the ventricle portion 212), and a medial portion (e.g., at the annulus portion 214) therebetween. The upper end or atrium portion 216 (also referred to as "outer free end portion") defines an open end portion of the outer frame assembly 210. The medial or annulus portion 214 of the outer frame assembly 210 has a perimeter that is configured (e.g., sized, shaped) to fit into an annulus of a native atrioventricular valve. The upper end of the outer frame assembly 210 has a perimeter that is larger than the perimeter of the medial portion. In some embodiments, the perimeter of the upper end of the outer frame assembly 210 has a perimeter that is substantially larger than the perimeter of the medial portion. As shown best in FIG. 5, the upper end and the medial portion of the outer frame assembly 210 has a D-shaped cross-section. In this manner, the outer frame assembly 210 promotes a suitable fit into the annulus of the native atrioventricular valve.

Inner valve assembly 240 includes an inner frame 250, an outer covering (not shown), and leaflets 270. As shown, the inner valve assembly 240 includes an upper portion having a periphery formed with multiple arches. The inner frame 250 includes six axial posts or frame members that support the outer covering of the inner valve assembly and leaflets 270. Leaflets 270 are attached along three of the posts, shown as commissure posts 252 (best illustrated in FIG. 4), and the outer covering of the inner valve assembly 240 is attached to the other three posts, 254 (best illustrated in FIG. 4), and optionally to commissure posts 252. Each of the outer covering of the inner valve assembly 240 and leaflets 270 are formed of approximately rectangular sheets of material, which are joined together at their upper, or atrium end. The lower, ventricle end of the outer covering may be joined to inner covering 232 of outer frame assembly 210, and the lower, ventricle end of leaflets 270 may form free edges 275, though coupled to the lower ends of commissure posts 252.

Although inner valve assembly 240 is shown as having three leaflets, in other embodiments, an inner valve assembly can include any suitable number of leaflets. The leaflets 270 are movable between an open configuration and a closed configuration in which the leaflets 270 coapt, or meet in a sealing abutment.

Outer covering 230 of the outer frame assembly 210 and inner covering 232 of outer frame assembly 210, outer covering of the inner valve assembly 240 and leaflets 270 of the inner valve assembly 240 may be formed of any suitable material, or combination of materials, such as those discussed above. In this embodiment, the inner covering 232 of the outer frame assembly 210, the outer covering of the inner valve assembly 240, and the leaflets 270 of the inner valve assembly 240 are formed, at least in part, of porcine pericardium. Moreover, in this embodiment, the outer covering 230 of the outer frame assembly 210 is formed, at least in part, of polyester.

Figure 6:
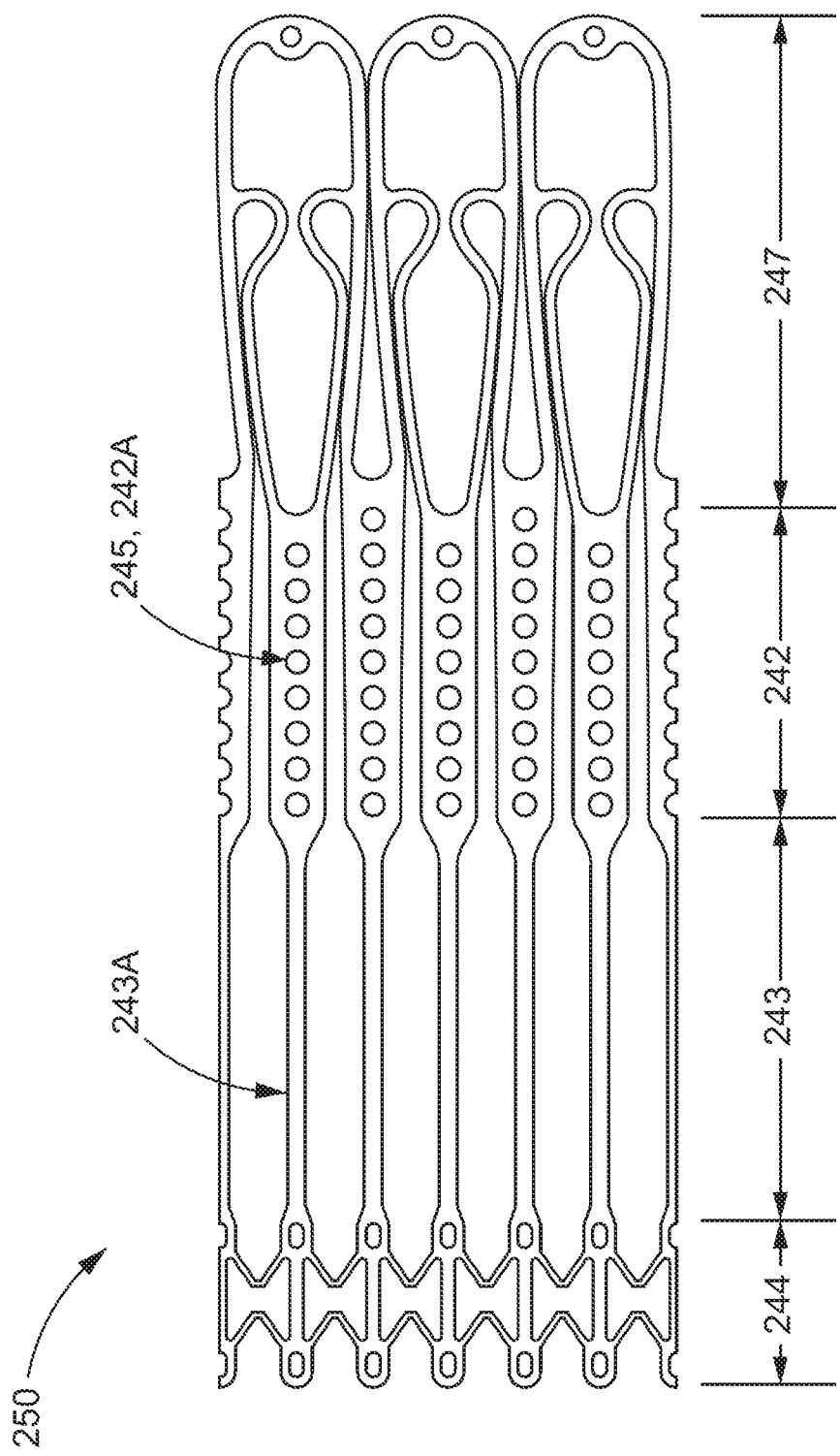
FIG. 6 is an opened and flattened view of the inner frame of the prosthetic heart valve of FIGS. 3-5, in an unexpanded configuration.
Figure 7:
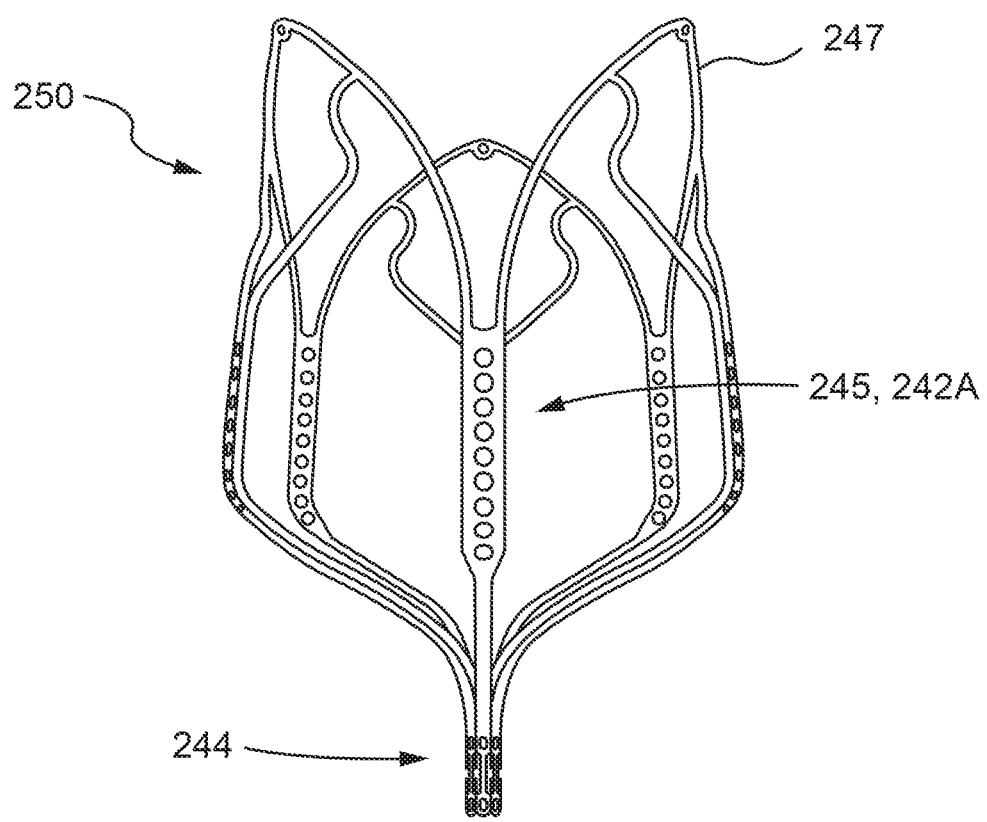
FIGS. 7 and 8 are side and bottom views, respectively, of the inner frame of FIG. 6 in an expanded configuration.
Figure 8:
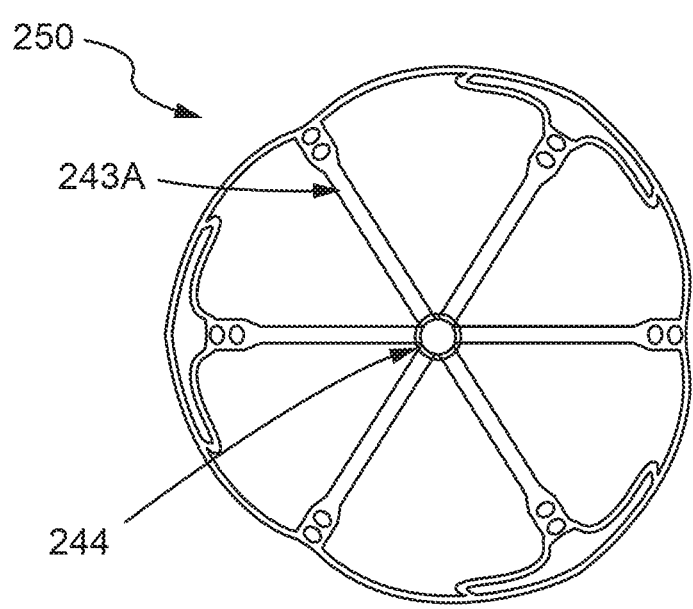

Inner frame 250 is shown in more detail in FIGS. 6-8. Specifically, FIGS. 6-8 show inner frame 250 in an undeformed, initial state (FIG. 6), a side view of the inner frame 250 in an expanded configuration (FIG. 7), and a bottom view of the inner frame 250 in the expanded configuration (FIG. 8), respectively, according to an embodiment.

In this embodiment, inner frame 250 is formed from a laser-cut tube of Nitinol®. Inner frame 250 is illustrated in FIG. 6 in an undeformed, initial state, i.e. as laser-cut, but cut and unrolled into a flat sheet for ease of illustration. Inner frame 250 can be divided into four portions, corresponding to functionally different portions of the inner frame 250 in final form: atrial portion 247, body portion 242, strut portion 243, and tether clamp or connecting portion 244. Strut portion 243 includes six struts, such as strut 243A, which connect body portion 242 to tether connecting portion 244.

Tether connecting portion 244 (also referred to as first end portion of inner frame) includes longitudinal extensions of the struts, connected circumferentially by pairs of opposed, slightly V-shaped connecting members (or "micro-Vs"). Tether connecting portion 244 is configured to be radially collapsed by application of a compressive force, which causes the micro-Vs to become more deeply V-shaped, with the vertices moving closer together longitudinally and the open ends of the V shapes moving closer together circumferentially. Thus, tether connecting portion 244 can be configured to compressively clamp or grip one end of a tether, either connecting directly onto a tether line (e.g. braided filament line) or onto an intermediate structure, such as a polymer or metal piece that is in turn firmly fixed to the tether line.

In contrast to tether connecting portion 244, atrial portion 247 (also referred to as "inner frame free end portion") and body portion 242 are configured to be expanded radially. Strut portion 243 forms a longitudinal connection and radial transition between the expanded body portion and the compressed tether connecting portion 244. Body portion 242 provides an inner frame coupling portion 245 that includes six longitudinal posts, such as post 242A. The inner frame coupling portion 245 can be used to attach leaflets 270 to inner frame 240, and/or can be used to attach inner assembly 240 to outer assembly 210, such as by connecting inner frame 250 to outer frame 220. In the illustrated embodiment, the posts include openings through which connecting members (such as suture filaments and/or wires) can be passed to couple the posts to other structures.

Inner frame 250 is shown in a fully deformed, i.e. the final, deployed configuration, in side view and bottom view in FIGS. 7 and 8, respectively.

Figure 9:
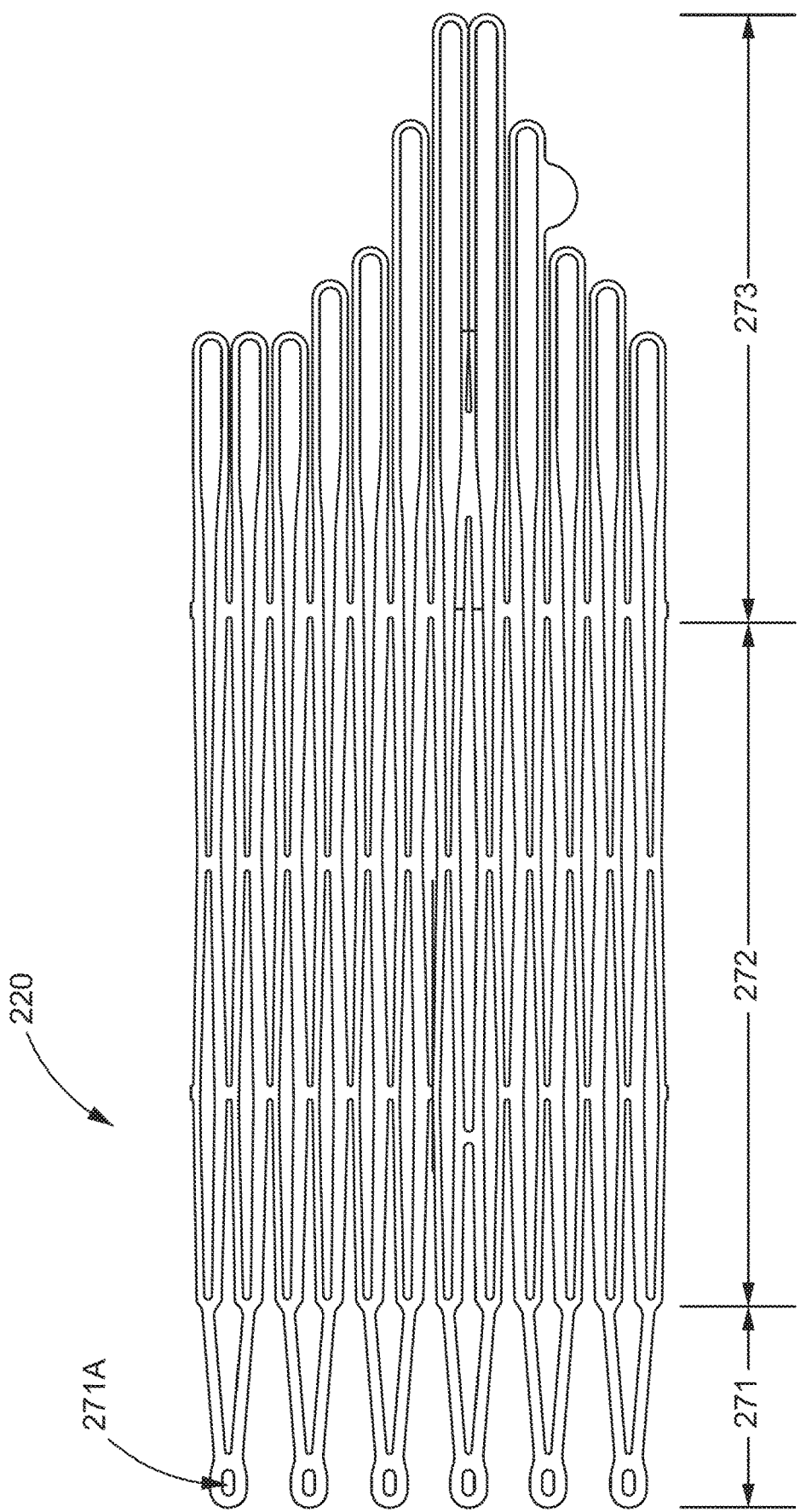
FIG. 9 is an opened and flattened view of the outer frame of the valve of FIGS. 3-5, in an unexpanded configuration.
Figure 10:
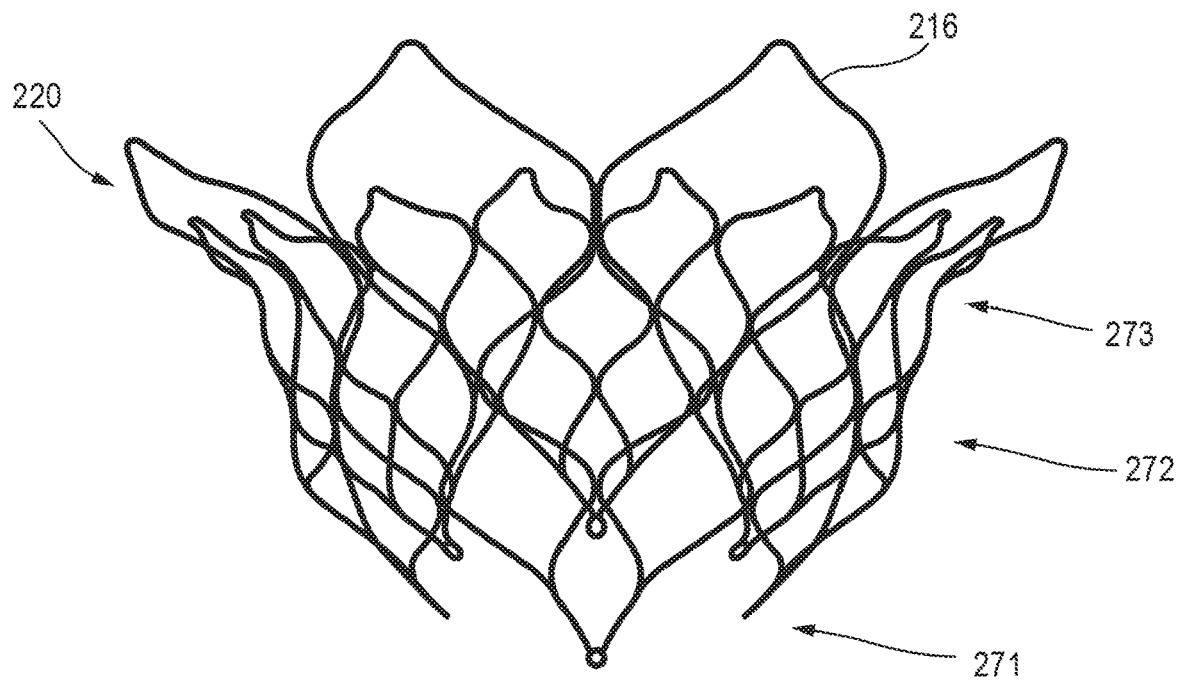
FIGS. 10 and 11 are side and top views, respectively, of the outer frame of FIG. 9 in an expanded configuration.
Figure 11:
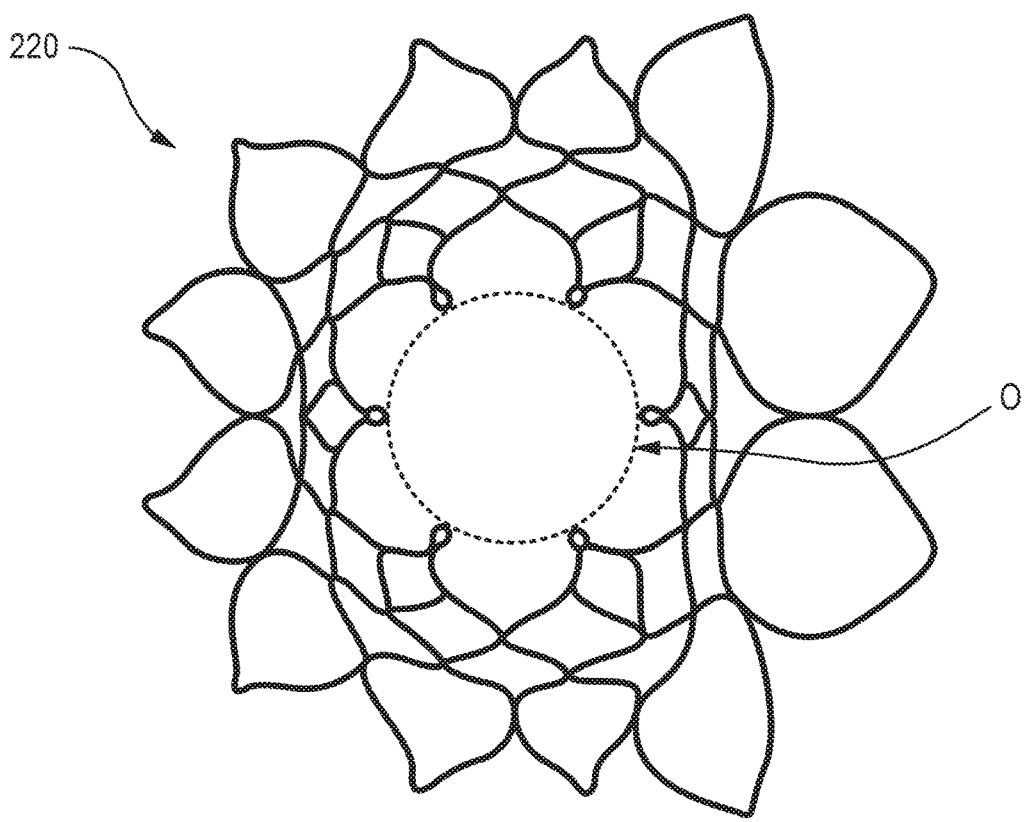

Outer frame 220 of valve 200 is shown in more detail in FIGS. 9-11. In this embodiment, outer frame 220 is also formed from a laser-cut tube of Nitinol®. Outer frame 220 is illustrated in FIG. 9 in an undeformed, initial state, i.e. as laser-cut, but cut and unrolled into a flat sheet for ease of illustration. Outer frame 220 can be divided into an outer frame coupling portion 271, a body portion 272, and a cuff portion 273 (which includes the atrium or free end portion 216), as shown in FIG. 9. Outer frame coupling portion 271 includes multiple openings or apertures, such as 271A, by which outer frame 220 can be coupled to inner frame 250, as discussed in more detail below.

Outer frame 220 is shown in a fully deformed, i.e. the final, deployed configuration, in side view and top view in FIGS. 10 and 11, respectively. As best seen in FIG. 11, the lower end of outer frame coupling portion 271 forms a roughly circular opening (identified by "O" in FIG. 11). The diameter of this opening preferably corresponds approximately to the diameter of body portion 242 of inner frame 250, to facilitate coupling of the two components of valve 200.

Figure 12:
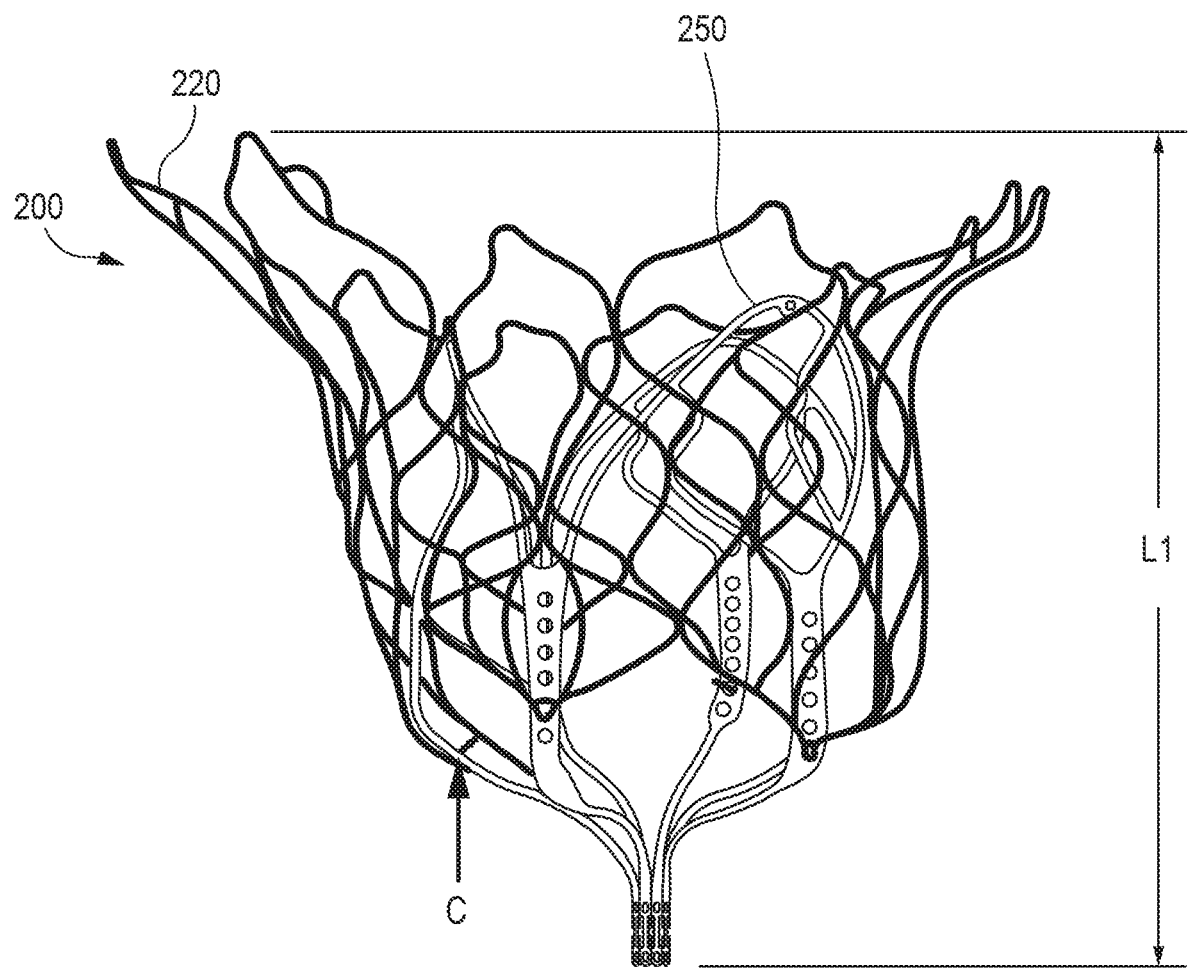
FIGS. 12-14 are side, front, and top views of an assembly of the inner frame of FIGS. 6-8 and the outer frame of FIGS. 9-11.
Figure 13:
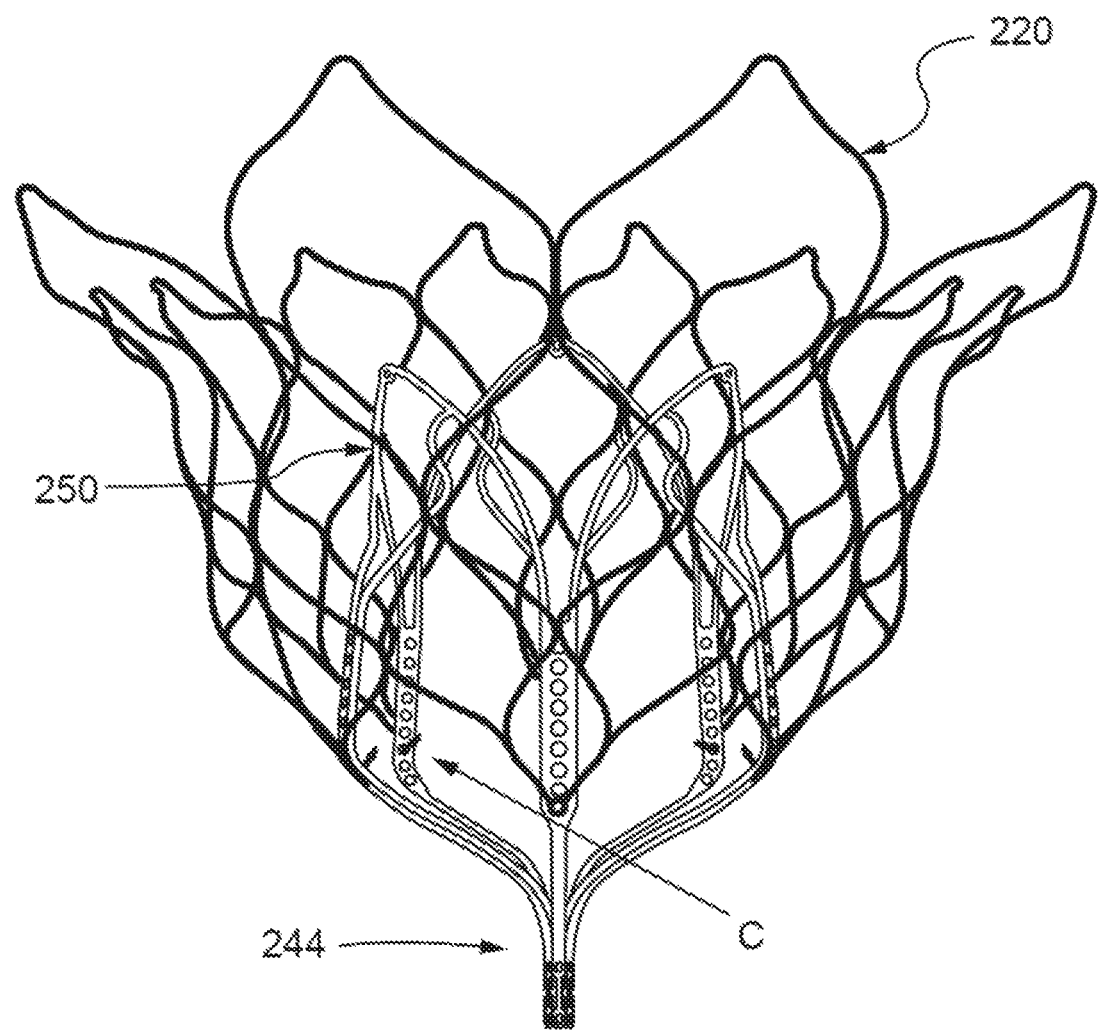
Figure 14:
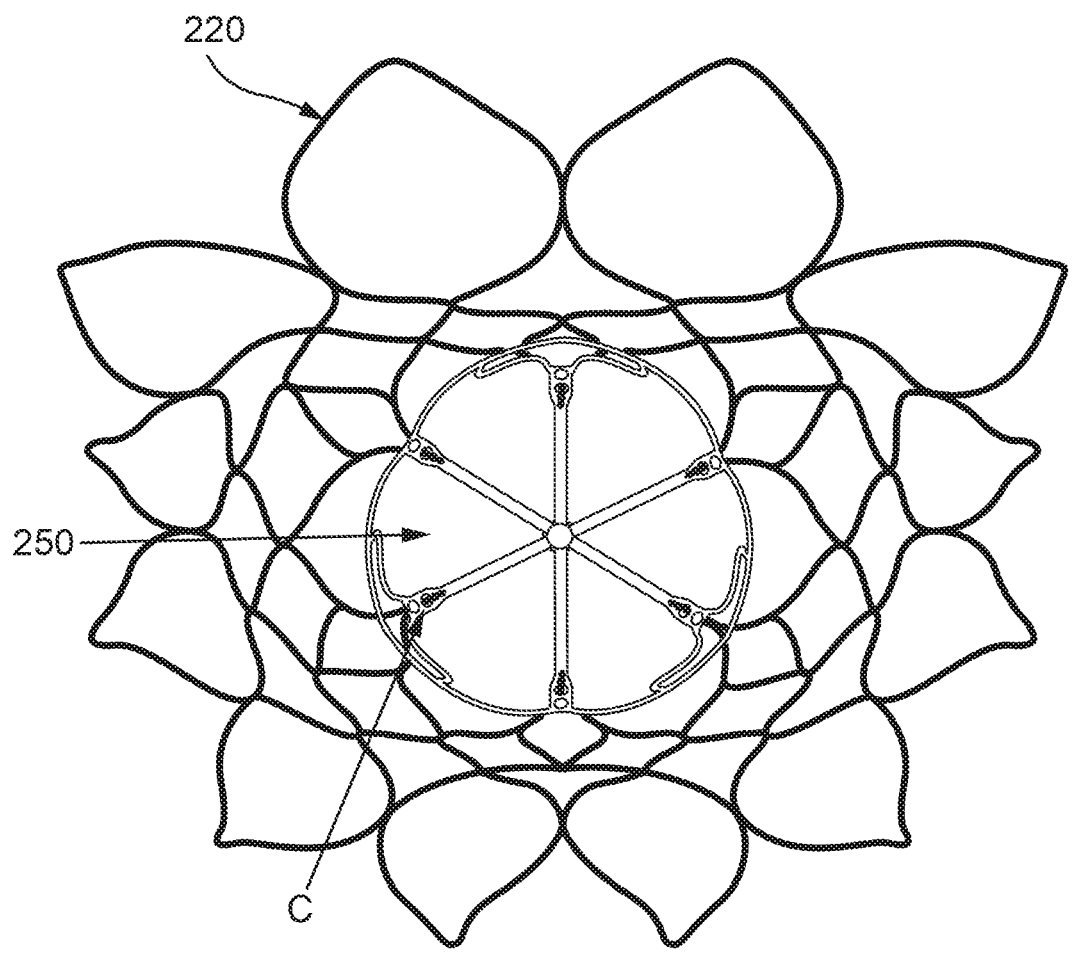

Outer frame 220 and inner frame 250 are shown coupled together in FIGS. 12-14, in front, side, and top views, respectively. The two frames collectively form a structural support for a prosthetic valve such as valve 200. The frames support the valve leaflet structure (e.g., leaflets 270) in the desired relationship to the native valve annulus, support the coverings (e.g., outer covering 230, inner covering 232, outer covering of inner valve assembly 240) for the two frames to provide a barrier to blood leakage between the atrium and ventricle, and couple to the tether (e.g., tether assembly 290) (by the inner frame 250) to aid in holding the prosthetic valve 200 in place in the native valve annulus by the tether connection to the ventricle wall. The outer frame 220 and the inner frame 250 are connected at six coupling points (representative points are identified as "C"). In this embodiment, the coupling points are implemented with a mechanical fastener, such as a short length of wire, passed through an aperture (such as aperture 271A) in outer frame coupling portion 271 and corresponding openings in inner frame coupling portion 245 (e.g., longitudinal posts, such as post 242A) in body portion 242 of inner frame 250. Inner frame 250 is thus disposed within the outer frame 220 and securely coupled to it.

FIGS. 15-21 illustrate a method of reconfiguring a prosthetic heart valve 300 (e.g., prosthetic mitral valve) prior to inserting the prosthetic heart valve 300 into a delivery sheath 326 (see, e.g., FIGS. 17-21) for delivery into the atrium of the heart. The prosthetic heart valve 300 (also referred to herein as "valve") can be constructed the same as or similar to, and function the same as or similar to the valves 100 and 200 described above. Thus, some details regarding the valve 300 are not described below. It should be understood that for features and functions not specifically discussed, those features and functions can be the same as or similar to the valve 200.

Figure 15:
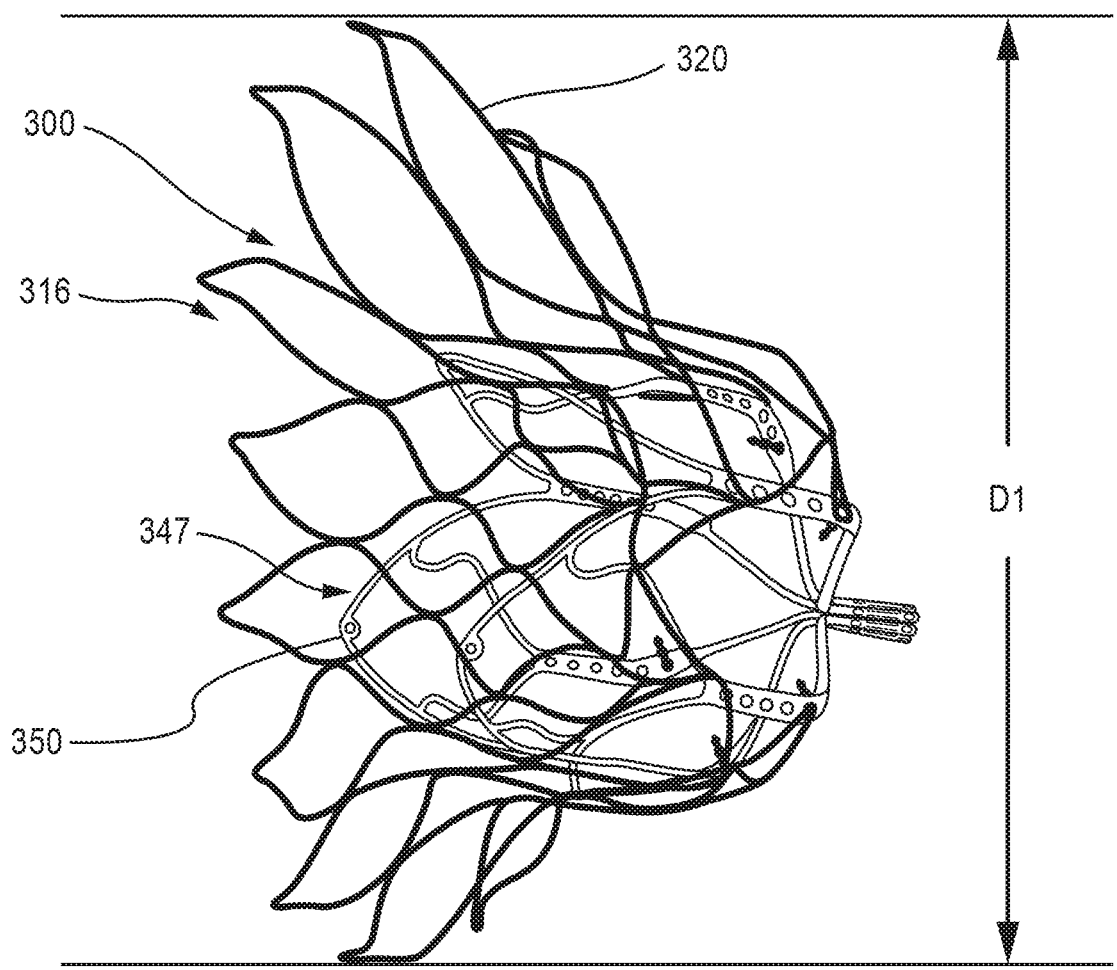
FIG. 15 is a side perspective view of an assembly of an inner frame and an outer frame shown in a biased expanded configuration, according to an embodiment.
Figure 16:
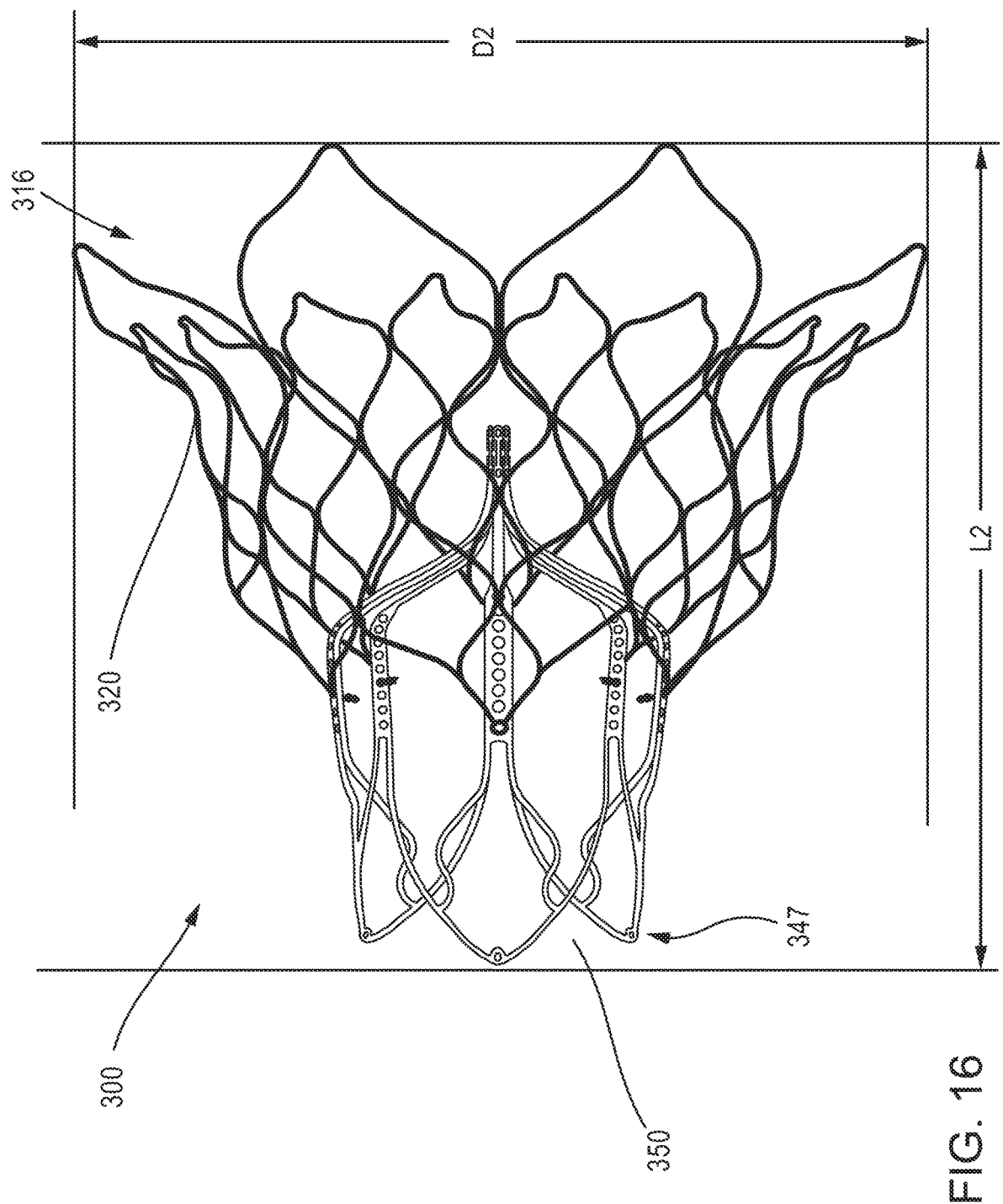
FIG. 16 is a side perspective view of the assembly of FIG. 15 with the outer frame shown inverted.
Figure 17:
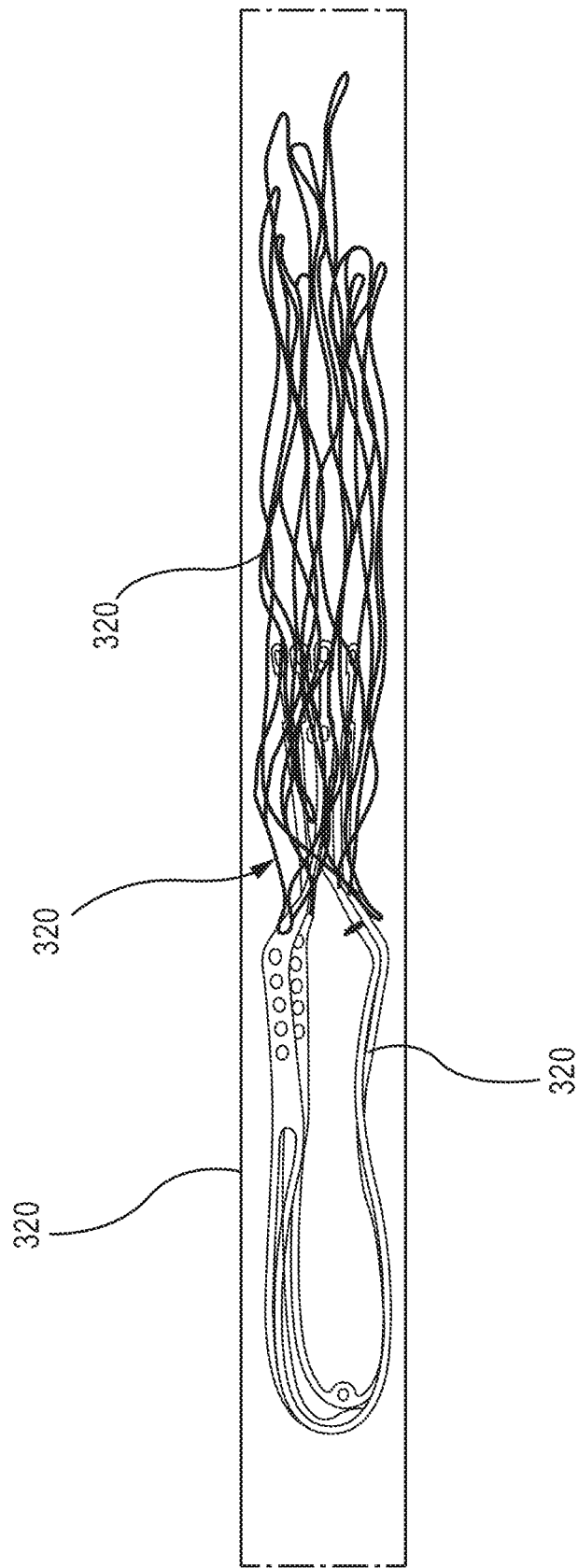
FIG. 17 is side view of the assembly of FIG. 16 shown in a collapsed configuration within a lumen of a delivery sheath.

As shown in FIG. 15, the valve 300 has an outer frame 320 and an inner frame 350. As discussed above for valves 100 and 200, the outer frame 320 and the inner frame 350 of valve 300 can each be formed with a shape-memory material and have a biased expanded configuration. The outer frame 320 and the inner frame 350 can be moved to a collapsed configuration for delivery of the valve 300 to the heart. In this example method of preparing the valve 300 for delivery to the heart, the outer frame 320 of the valve 300 is first disposed in a prolapsed or inverted configuration as shown in FIG. 16. Specifically, the elastic or superelastic structure of outer frame 320 of valve 300 allows the outer frame 320 to be disposed in the prolapsed or inverted configuration prior to the valve 300 being inserted into the lumen of the delivery sheath 326. As shown in FIG. 16, to dispose the outer frame 320 in the inverted configuration, the outer frame 320 is folded or inverted distally (to the right in FIG. 16) such that an open free end 316 of the outer frame 320 is pointed away from an open free end 347 of the inner frame 350. As described above for valve 100, in this inverted configuration, the overall outer perimeter or outer diameter of the valve 300 is reduced and the overall length is increased. For example, the diameter D1 shown in FIG. 15 is greater than the diameter D2 shown in FIG. 16, and the length L1 (shown in FIG. 12 for valve 200) is less than the length L2 shown in FIG. 16 for valve 300. With the outer frame 320 in the inverted configuration relative to the inner frame 350, the valve 300 can be placed within a lumen of a delivery sheath 326 as shown in FIG. 17 for delivery of the valve 300 to the left atrium of the heart. By disposing the outer frame 320 in the inverted configuration relative to the inner frame 350, the valve 300 can be collapsed into a smaller overall diameter, i.e. when placed in a smaller diameter delivery sheath, than would be possible if the valve 300 in the configuration shown in FIG. 15 were collapsed radially without being inverted. This is because in the configuration shown in FIG. 15, the two frames are concentric or nested, and thus the outer frame 320 must be collapsed around the inner frame 350, whereas in the configuration shown in FIG. 16, the two frames are substantially coaxial but not concentric or nested. Thus, in the configuration shown in FIG. 16 the outer frame 320 can be collapsed without the need to accommodate the inner frame 350 inside of it. In other words, with the inner frame 350 disposed mostly inside or nested within the outer frame 320, the layers or bulk of the frame structures cannot be compressed to as small a diameter. In addition, if the frames are nested, the structure is less flexible, and therefore, more force is needed to bend the valve, e.g. to pass through tortuous vasculature or to make tight turns in the left atrium after passing through the atrial septum to be properly oriented for insertion into the mitral valve annulus.

Figure 22:
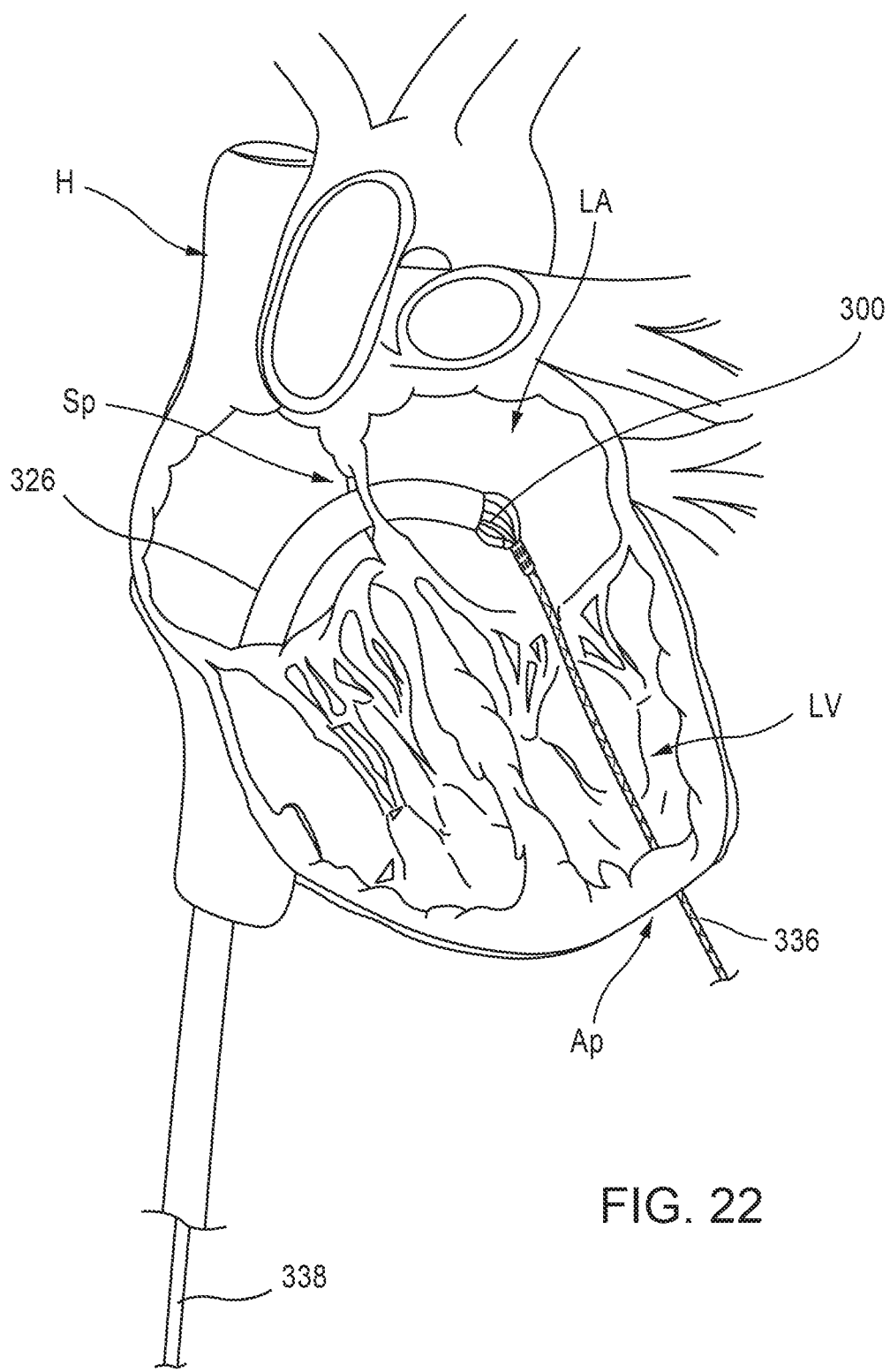
FIGS. 22-24 illustrate steps of a portion of a method to deliver the prosthetic valve of FIGS. 15-21 to an atrium of a heart and within the native mitral annulus.
Figure 23:
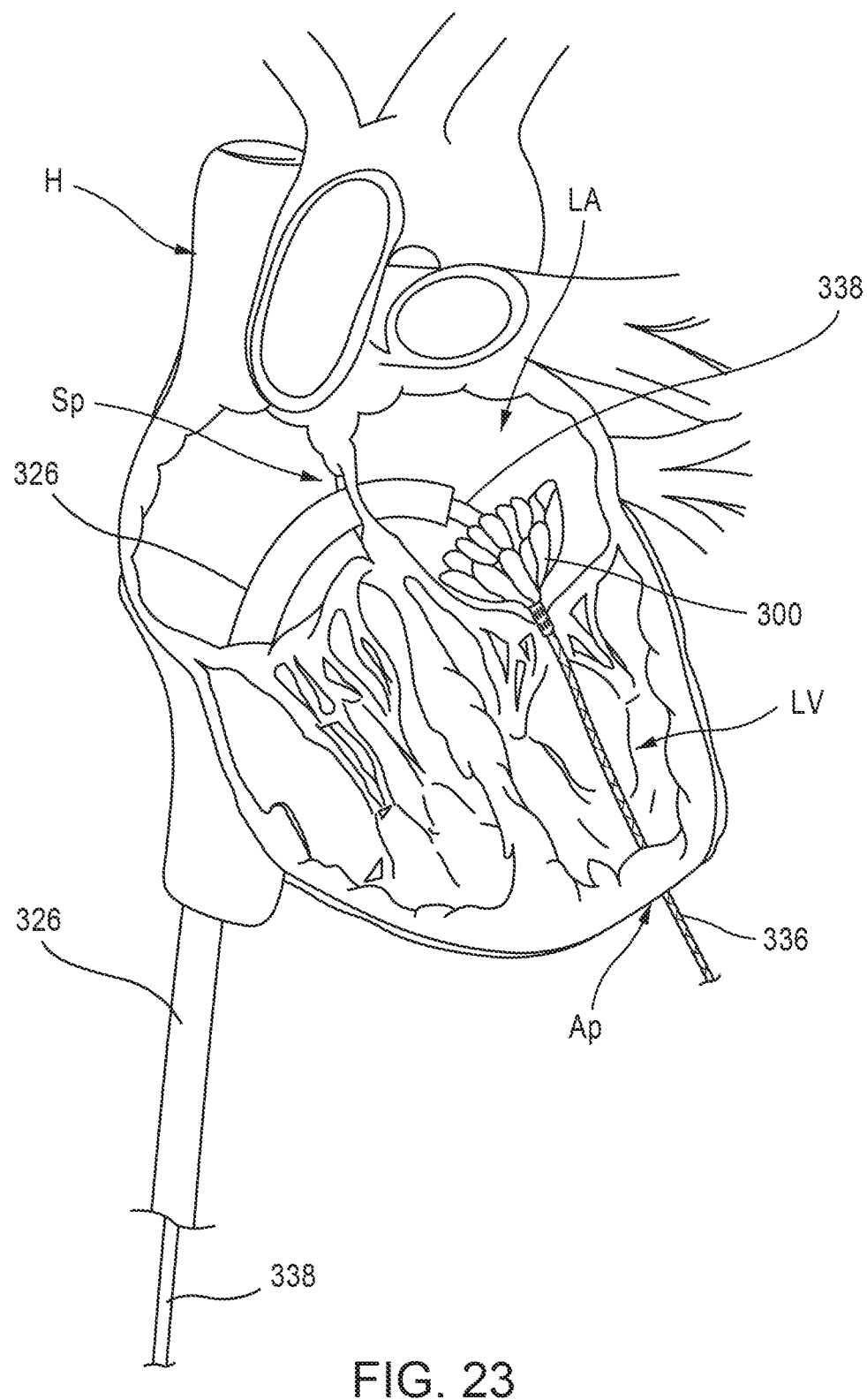
Figure 24:
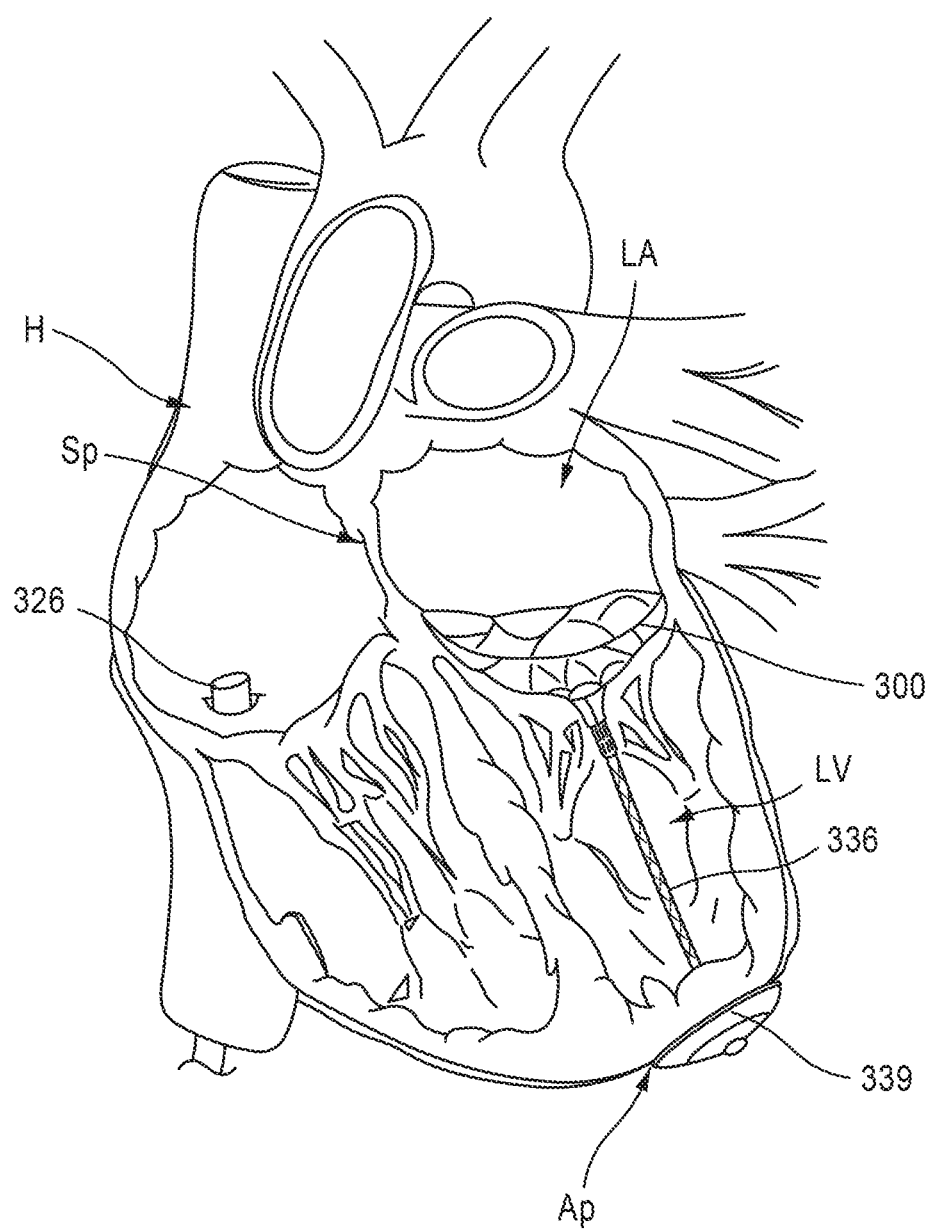

FIGS. 22-24 illustrate a portion of a procedure to deliver the valve 300 to the heart. In this embodiment, the valve 300 is shown being delivered via a transfemoral delivery approach as described, for example, in the '572 PCT application incorporated by reference above. The delivery sheath 326, with the valve 300 disposed within a lumen of the delivery sheath 326 and in an inverted configuration as shown in FIG. 17, can be inserted into a femoral puncture, through the femoral vein, through the inferior vena cava, into the right atrium, through the septum Sp and into the left atrium LA of the heart. With the distal end portion of the delivery sheath 326 disposed within the left atrium of the heart, the valve 300 can be deployed outside a distal end of the delivery sheath 326. For example, in some embodiments, a pusher device 338 can be used to move or push the valve 300 out the distal end of the delivery sheath 326. As shown in FIGS. 22-24, a tether 336 can be attached to the valve 300, and extend though the mitral annulus, through the left ventricle LV, and out a puncture site at the apex Ap. In some embodiments, the valve 300 can be moved out of the delivery sheath 326 by pulling proximally on the tether 336. In some embodiments, the valve 300 can be deployed by pushing with the pusher device and pulling with the tether.

Figure 18:
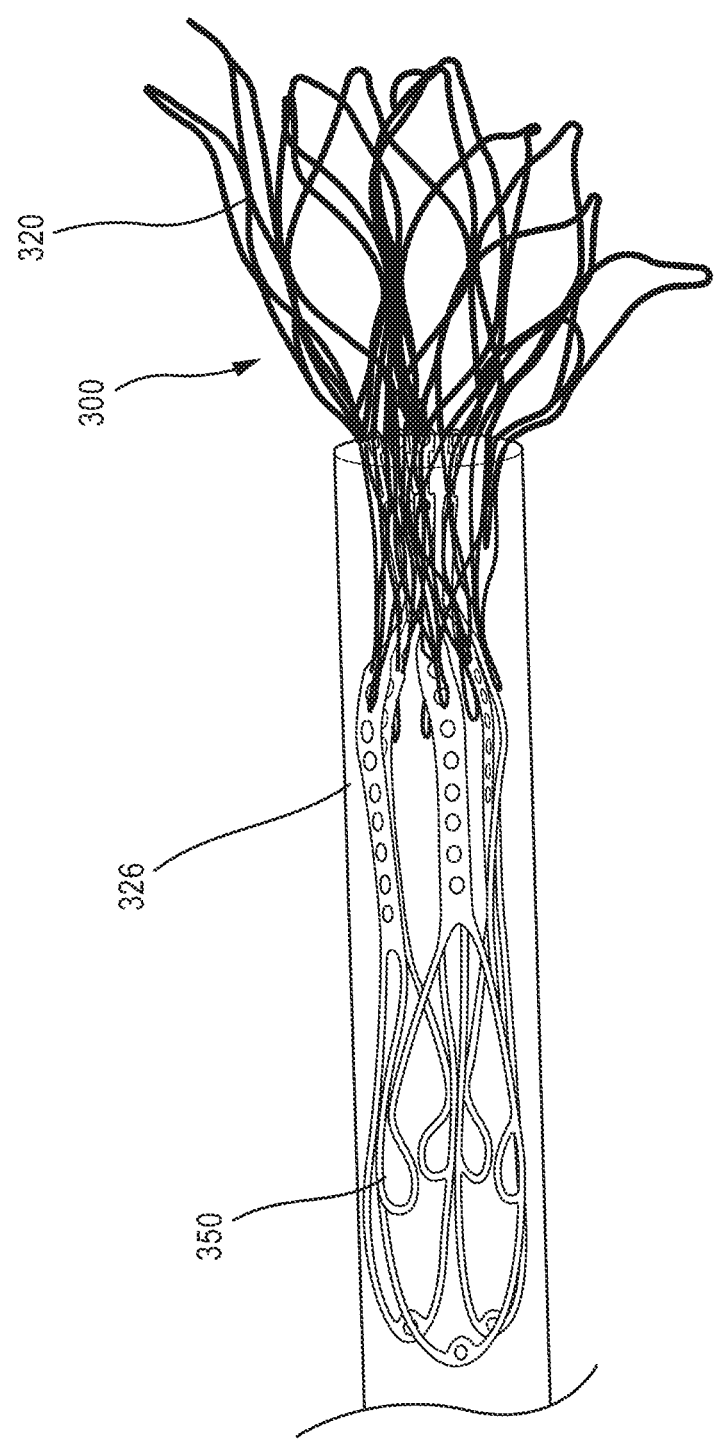
FIG. 18 is a side view of the assembly of FIG. 17 shown in a first partially deployed configuration.
Figure 19:
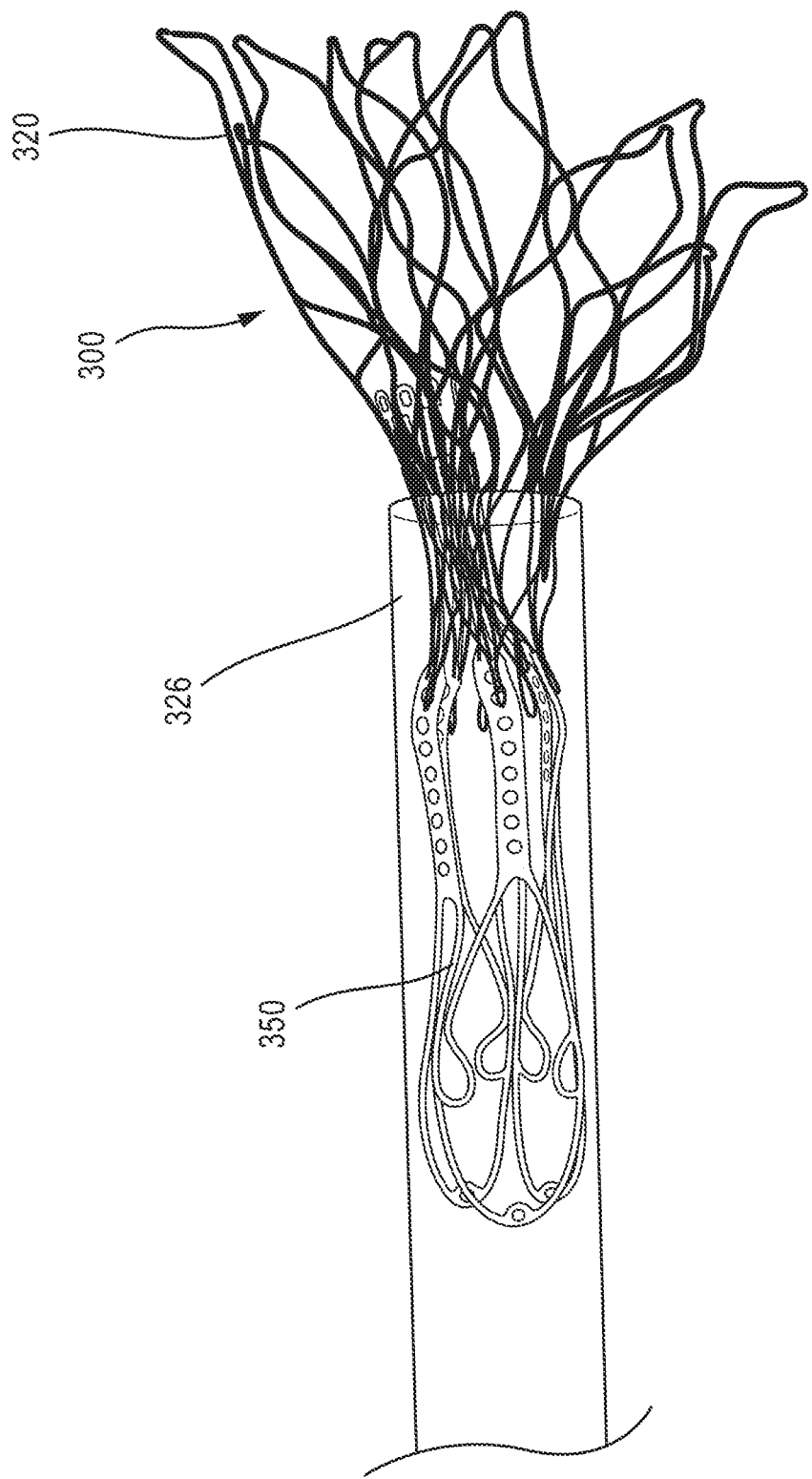
FIG. 19 is a side view of the assembly of FIG. 17 shown in a second partially deployed configuration.
Figure 20:
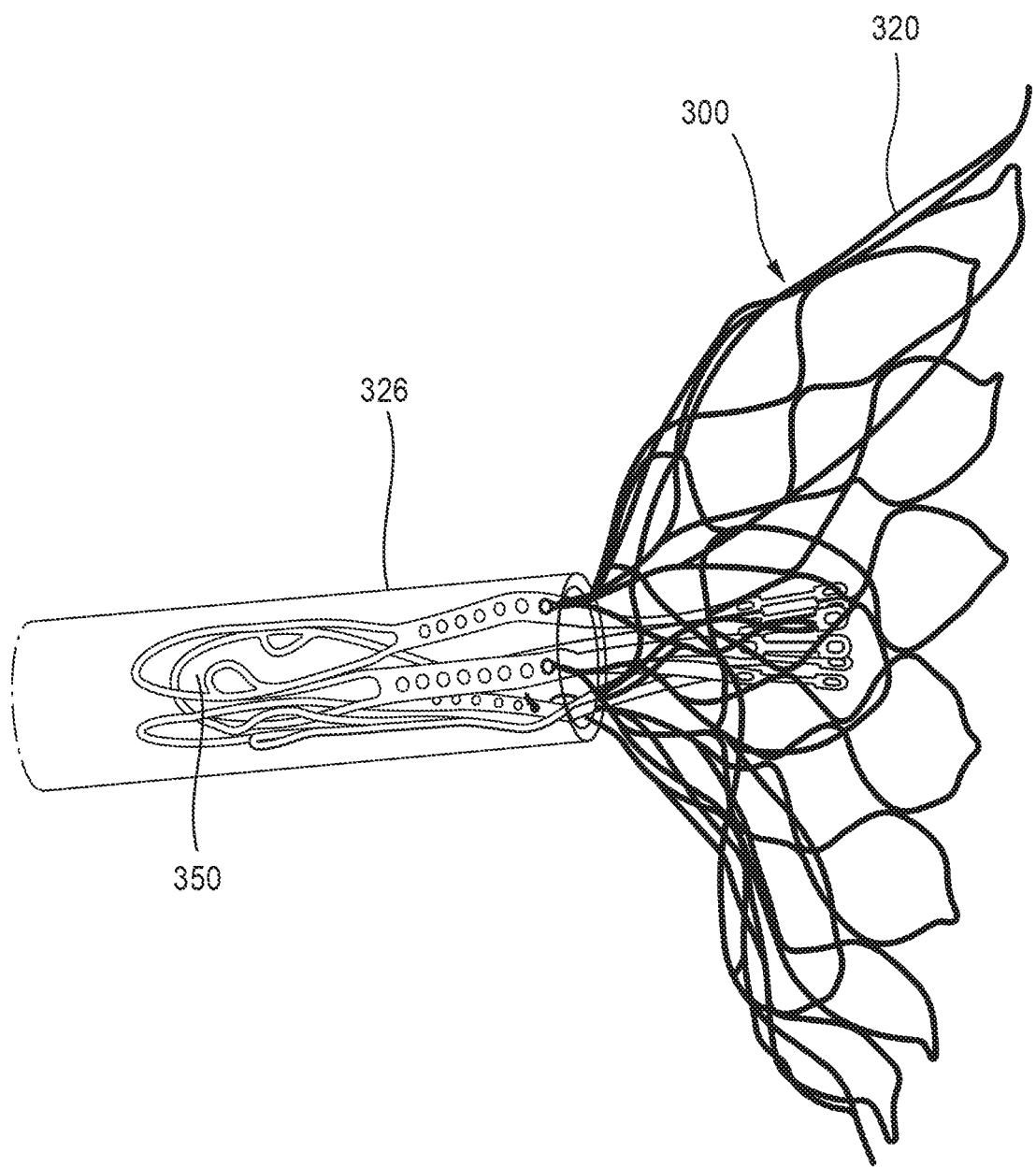
FIG. 20 is a side view of the assembly of FIG. 17 shown in a third partially deployed configuration in which the inverted outer frame is substantially deployed outside of the delivery sheath.
Figure 21:
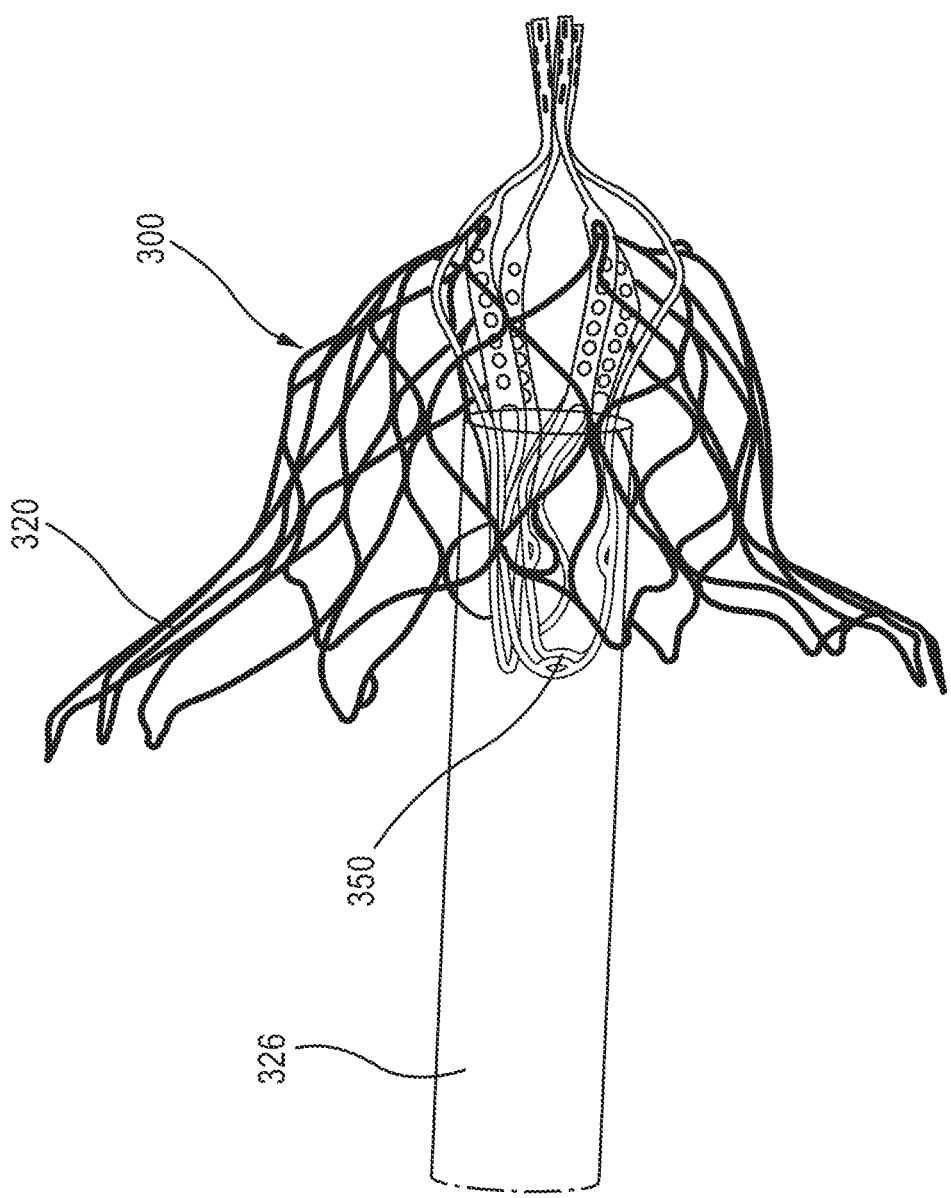
FIG. 21 is a side view of the assembly of FIG. 17 shown in a fourth partially deployed configuration in which the outer frame has reverted and assumed a biased expanded configuration.

As the valve 300 exits the lumen of the delivery sheath 326, the outer frame assembly 310 exits first in its inverted configuration as shown in the progression of FIGS. 18-20 (see also FIG. 22). After the outer frame assembly 310 is fully outside of the lumen of the delivery sheath 326, the outer frame 320 can revert to its expanded or deployed configuration as shown in FIGS. 21, 23 and 24. In some embodiments, the outer frame 320 can revert automatically after fully exiting the lumen of the delivery sheath due to its shape-memory properties. In some embodiments, a component of the delivery sheath or another device can be used to aid in the reversion of the outer frame assembly 310. In some embodiments, the pusher device and/or the tether can be used to aid in the reversion of the outer frame assembly 310. The valve 300 can continue to be deployed until the inner frame 350 is fully deployed with the left atrium and the valve 300 is in the expanded or deployed configuration (as shown, e.g., in FIGS. 15 and 24). The valve 300 and the tether 336 can then be secured to the apex of the heart with an epicardial pad device 339 as shown in FIG. 24 and as described in more detail in the '572 PCT application and the '305 PCT application incorporated by reference above.

Figure 25:
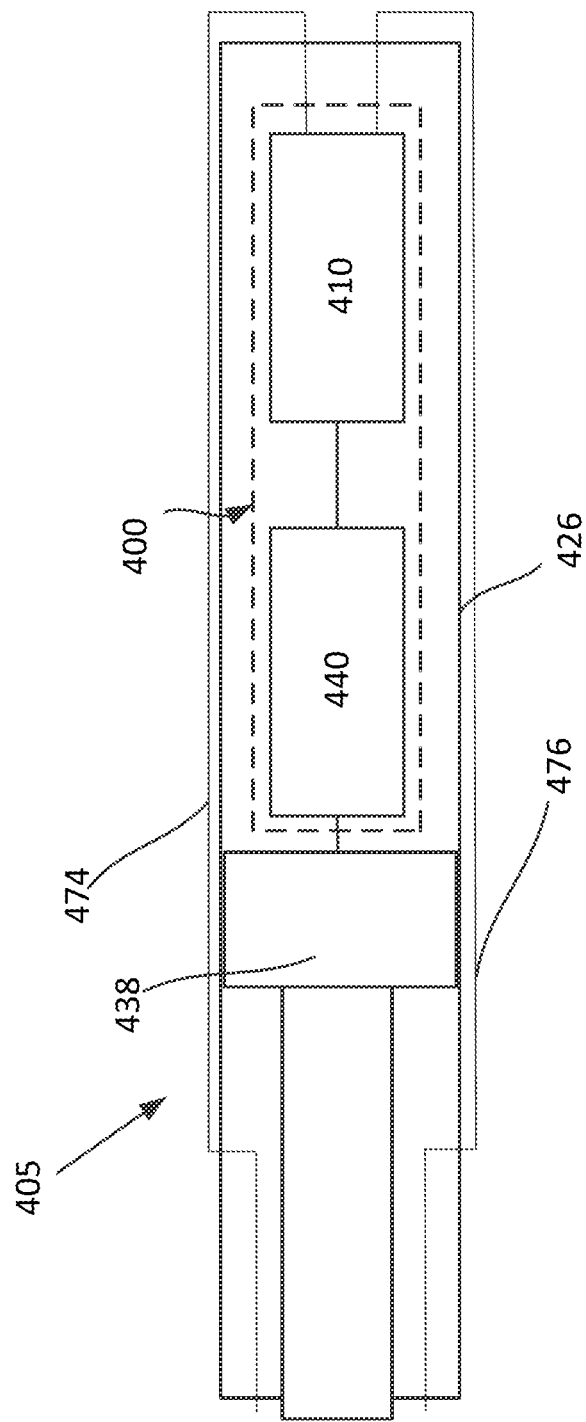
FIG. 25 is a schematic illustration of a delivery device and prosthetic heart valve, according to an embodiment.

FIG. 25 illustrates schematically an embodiment of a delivery system (also referred to as a "delivery device") that can be used to deliver and deploy a prosthetic heart valve within a heart of a patient with, for example, a transvascular approach. In this embodiment, a delivery system 405 includes a delivery sheath 426, a valve holder 438 (also referred to as a "pusher"), and one or more actuation wires 474 and 476. In this schematic illustration, only two actuation wires are illustrated, but in other embodiments, only one actuation wire or more than two actuation wires can be used. The actuation wires 474, 476 can be, for example, a flexible tension member/tether, made of monofilament or multiple filaments woven, knit, or braided, polymer, metal, natural fiber, etc. The actuation wires 474, 476 can be, for example, a suture.

Figure 26B:
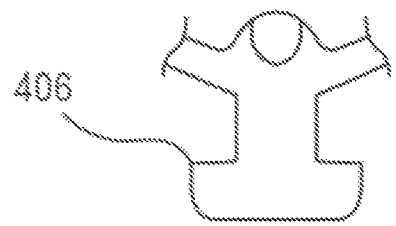
FIG. 26B is a side view of an attachment member of the prosthetic valve of FIG. 26A.
Figure 26C:
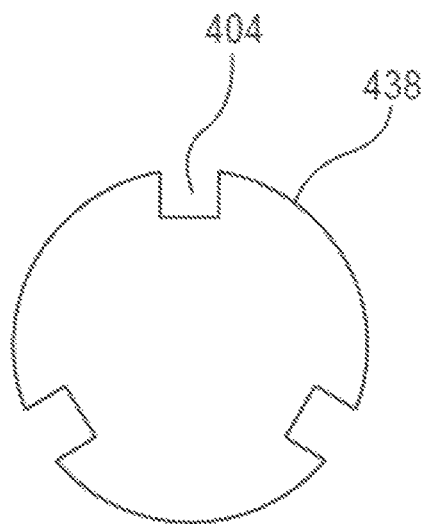
FIG. 26C is an end view of the valve holder of FIG. 26A.
Figure 26A:
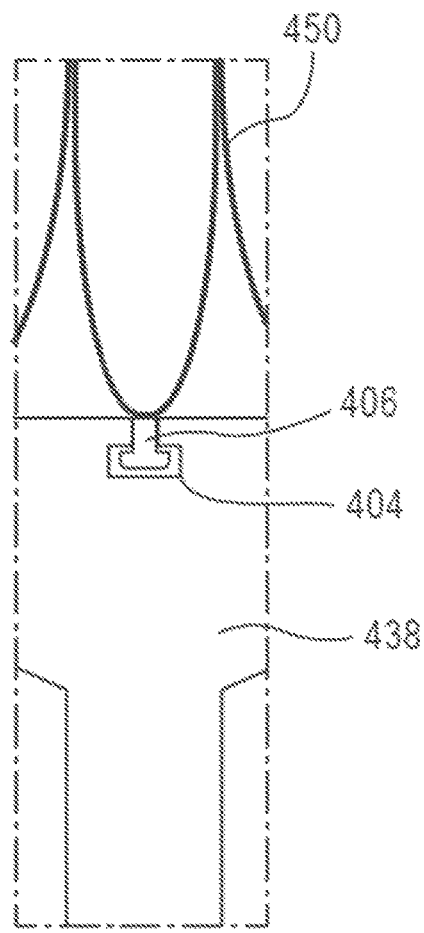
FIG. 26A is a side view of a portion of the prosthetic heart valve of FIG. 25 shown within a delivery sheath and coupled to a valve holder.

The delivery sheath 426 can be used to deliver a valve 400 that includes an inner valve assembly 440 including an inner frame (not labeled in FIG. 25) and an outer frame assembly 410 including an outer frame (not labeled in FIG. 25). The valve 400 can be constructed the same as or similar to, and function the same as or similar to, for example, any of the prosthetic valves described herein and/or in the '305 PCT application, and can be moved between a deployed or expanded configuration and a delivery configuration in which the outer frame is disposed in an inverted position relative to the inner frame as described herein and/or in the '305 PCT application. As shown in FIG. 25, the valve 400 can be disposed within a lumen of the delivery sheath 426 when the valve is in the delivery configuration (i.e., the outer frame is inverted relative to the inner frame). In this embodiment, when in the delivery configuration and placed within a delivery sheath, the outer frame assembly 410 is disposed distal of the inner valve assembly 440. The valve holder 438 is coupled to the inner valve assembly 440 and the actuation wires are coupled to the outer fame assembly 410. The valve holder 438 can be releasably coupled to the inner frame assembly 440 via couplers 406 that are attached to the inner frame assembly 440 as shown in FIGS. 26A-26C. In this embodiment, the couplers 406 are in the form of a T-bar or hammer shape. It should be understood that couplers with other configurations and shapes can be used.

As shown in FIG. 26A, the couplers 406 are received within the recesses 404 and the valve 400 and the valve holder 438 can be disposed within the lumen of the delivery sheath 426. The inner diameter of the delivery sheath 426 can be sized such that when the valve holder 438 and valve 400 are disposed therein, the couplers 406 are unable to exit the recesses 404. In other words, the inner walls of the delivery sheath 426 maintain the couplers 406 within the recesses 404. When the valve 400 is moved outside of the delivery sheath 426, the couplers 406 will be able to freely exit the recesses 404 releasing the inner frame 450 from the valve holder 438.

In alternative embodiments, the valve holder 438 can be removably coupled to the valve 400 (e.g., the inner frame 450 of the valve 400) via wires or sutures that can be cut after delivery of the valve 400 to the heart. In some cases, the valve holder 438 can be decoupled from the valve 400 when the valve is still disposed within the delivery sheath 426, while in other instances the valve holder 438 can be decoupled from the valve 400 after the valve 400 exits the delivery sheath 426 within the heart.

The actuation wires 474 and 476 can be coupled to the outer frame of the outer frame assembly 410 with a variety of different coupling methods. For example, the outer frame 410 can include loops (as described below, for example, with respect to outer frame 510, and in the '305 PCT application) through which the actuation wires 474 and 476 can be received or threaded. The number of loops on the outer frame can vary and the number of loops through which each actuation wire is connected can vary. For example, in some embodiments, the outer frame includes 12 loops and a first actuation wire is threaded through 6 of the loops and a second actuation wire is threaded through 6 of the loops. In other embodiments, the outer frame can include 12 loops and there can be 4 actuation wires, each coupled to 3 of the loops. In some embodiments, a single actuation wire is coupled through all of the loops of the outer frame.

In this embodiment, the delivery sheath 426 can be used to deliver the valve 400 to the left atrium of the heart using a transvascular approach (e.g., transfemoral, transatrial, transjugular). When the distal end of the delivery sheath 426 is disposed within the left atrium, the valve 400 is moved out of the lumen of the delivery sheath 426 using the actuation wires 474, 476 to assist in pulling the valve 400 out of the delivery sheath 426. In some cases, the valve holder 438 can also be used to push the valve 400 out of the delivery sheath 426. More specifically, the actuation wires 474 and 476 can extend from the outer frame assembly 410 out a distal end of the delivery sheath and extend proximally. In some embodiments, the actuation wires 474, 476 extend proximally outside the delivery sheath 426, then pass back into the lumen of the delivery sheath 426 through side apertures or holes (not shown) and then out a proximal end of the delivery sheath 426. Thus, a user (e.g., physician) can pull the proximal end portions of the actuation wires 474 and 476 to in turn pull the outer frame assembly 410 out of the distal end of the delivery sheath 426. In some embodiments, the actuation wires 474, 476 extend proximally from the outer frame assembly 410, back through the distal end of the delivery sheath 426 (e.g., rather than through side apertures or holes of the delivery sheath) and within the lumen of the delivery sheath, and then out a proximal end of the delivery sheath 426. Various different embodiments and configurations are described in more detail below and in the '305 PCT application.

As the outer frame assembly 410 exits the delivery sheath 426 it will still be in an inverted configuration relative to the inner frame assembly 440. After the outer frame assembly 410 is at least partially outside of the lumen of the delivery sheath 426, the outer frame assembly 410 can begin to revert to its expanded or deployed configuration (not shown in FIG. 25). In this embodiment, however, the actuation wires 474 and 476 can function to selectively (e.g., by an operator) assist and/or control the expansion, deployment and/or articulation of the valve 400 as the valve 400 is delivered to the heart. In this manner, in use, the proximal end portions of the actuation wires 474, 476 can be pulled distally to manipulate the outer frame assembly 410 to assist and control the transition of the outer frame assembly 410 from its inverted configuration relative to the inner frame assembly 440 to its expanded or deployed configuration (not shown). In some embodiments, the actuation wires 474, 476 can be manually grasped by a user to pull the actuation wires proximally. In some embodiments, the actuation wires 474, 476 can be operatively coupled to the delivery system 405 such that the user does not have to manually handle the actuation wires. For example, the actuation wires can be coupled to a delivery sheath and/or to a handle assembly (not shown) of the delivery system 405. Various embodiments of a delivery system are described in more detail below and in the '305 PCT application.

Figure 27:
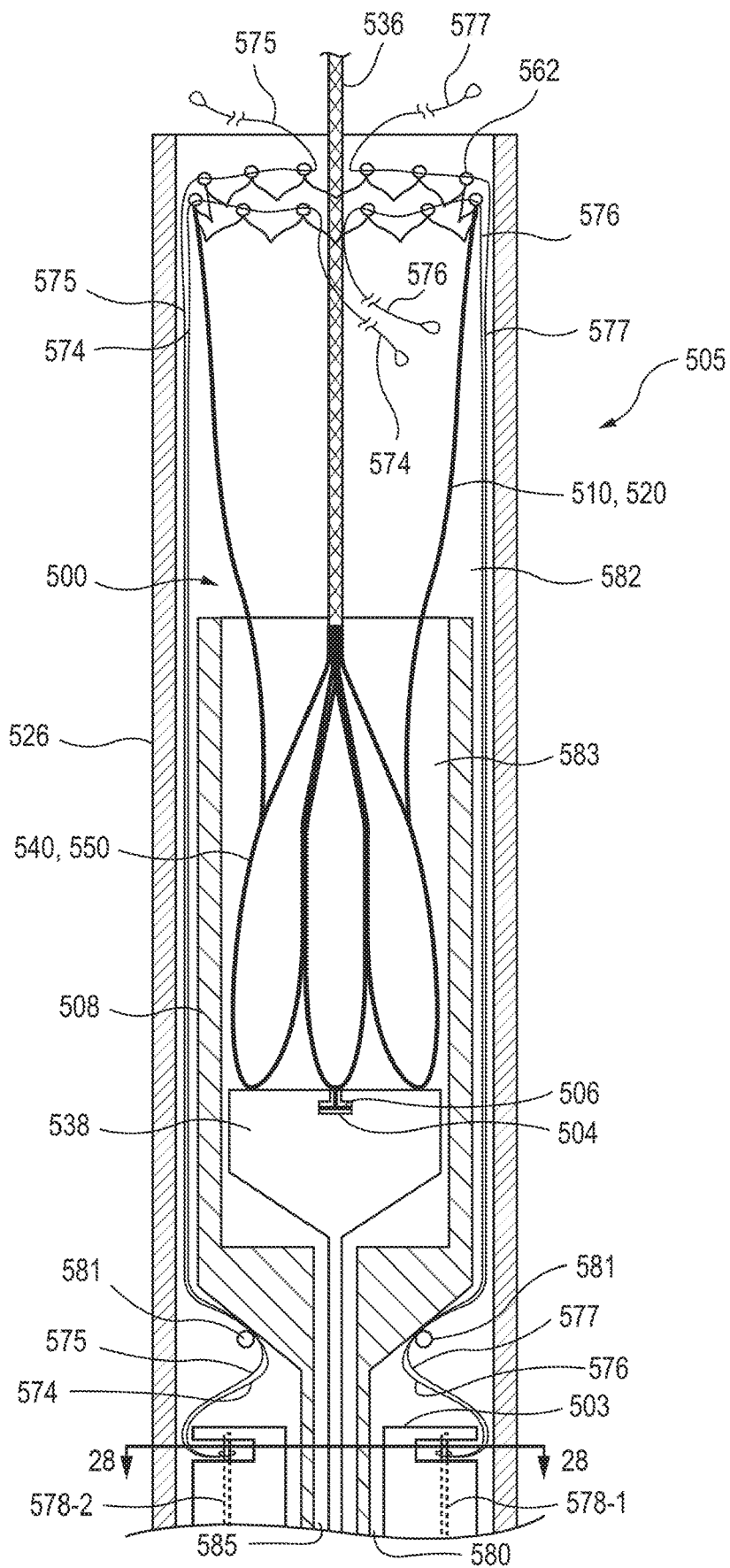
FIG. 27 is a partial cross-sectional side view of a delivery system and prosthetic heart valve, according to an embodiment.

FIGS. 27-35 illustrate a delivery system 505 for delivering and deploying a prosthetic heart valve, such as, prosthetic heart valve 500, within a heart, according to another embodiment. The prosthetic heart valve 500 (also referred to herein as "valve") can be constructed the same as or similar to, and function the same as or similar to any of the valves described herein. Thus, some details regarding the valve 500 are not described herein. As shown in FIG. 27, the valve 500 has an outer frame assembly 510 with an outer frame 520 and an inner valve assembly 540 with an inner frame 550, and a tether 536 coupled to the inner frame 550. As described above for previous embodiments (e.g., valve 100, 200, 300 etc.), the outer frame 520 and the inner frame 550 of valve the 500 can each be formed with a shape-memory material and have a biased, expanded or deployed configuration. The outer frame 520 and the inner frame 550 can be moved to a collapsed or undeployed configuration for delivery of the valve 500 to the heart in which the outer frame 520 is inverted relative to the inner frame 550. To prepare the valve 500 for delivery to the heart, the outer frame 520 of the valve 500 is first disposed in a prolapsed or inverted configuration as shown in FIG. 27. Specifically, the elastic or superelastic structure of outer frame 520 of valve 500 allows the outer frame 520 to be disposed in the prolapsed or inverted configuration relative to the inner frame 550 as described above, for example with respect to valve 100.

For example, to dispose the outer frame 520 in its inverted configuration relative to the inner frame 550, the outer frame 520 is folded or inverted distally such that the outer frame 520 is pointed away from the inner frame 550. With the outer frame 520 in the inverted configuration, the valve 500 can be placed within a lumen of the delivery system 505 as shown in FIG. 27 for delivery of the valve 500 to the left atrium of the heart. As discussed above, by disposing the outer frame 520 of the valve 500 in the inverted configuration, the valve 500 can be collapsed into a smaller overall diameter, i.e., placed in a smaller diameter delivery sheath, than would be possible if the valve 500 were collapsed radially when the inner frame 550 and the outer frame 520 are disposed concentric to one another.

In this embodiment, the delivery system 505 includes an outer delivery sheath 526, an inner sheath 508, a valve holder 538 (also referred to as a "pusher") and a multi-lumen elongate tube member 503 (also referred to as "tube" or "tube member" or "multi-lumen elongate member"). As shown in FIGS. 27 and 32-34, the tube member 503 is movably disposed within a lumen 582 defined by the outer delivery sheath 526. The inner sheath 508 is movably disposed within the lumen 582 and within a lumen 580 defined by the tube member 503. The valve holder 538 is movably disposed within a first lumen 583 and a second lumen 585 defined by the inner sheath 508 that are in fluid communication with each other.

To deploy the valve 500 within a heart, the outer frame 520 of the valve 500 is first moved or placed in its inverted configuration relative to the inner frame 550. As shown in FIG. 27, a portion of the valve 500 is placed within the lumen 582 of the outer sheath and a portion of the valve 500 is placed within the lumen 583 of the inner sheath 508. As described above for previous embodiments, when the valve 500 is placed within the delivery system (e.g., outer sheath 526 and inner sheath 508) the valve 500 can be compressed or collapsed to a smaller configuration (e.g., a smaller outer perimeter).

The inner frame 550 can be releasably coupled to the valve holder 538 via couplers 506 that are received within corresponding recesses 504 defined by the valve holder 538 in the same manner as described above for delivery system 405 (see, e.g., FIGS. 26A-26C). In this manner, the valve holder 538 can be used to hold the valve 500 to aid in the control and manipulation of the valve 500 as it is being deployed within a heart. In addition, the valve holder 538 can limit radial expansion of the inner frame 550 as the valve 500 is moved within the lumen of the delivery sheath 526 and during deployment outside of the delivery sheath 526. As described above for valve 400, an inner diameter 582 of the inner sheath 508 can be sized such that when the valve holder 538 and valve 500 are disposed therein, the couplers 506 are unable to exit the recesses 504. In other words, the inner walls of the inner sheath 508 maintain the couplers 506 within the recesses 504. When the valve 500 is moved outside of the inner sheath 508, the couplers 506 will be able to freely exit the recesses 504, releasing the inner frame 550 from the valve holder 538.

In alternative embodiments, the valve holder 538 can be removably coupled to the valve 500 (e.g., the inner frame 550 of the valve 500) via wires or sutures that can be cut after delivery of the valve 500 to the heart. In some cases, the valve holder 538 can be decoupled from the valve 500 when the valve is still disposed within the outer delivery sheath 526, while in other instances the valve holder 538 can be decoupled from the valve 500 after the valve 500 exits the delivery sheath 526 within the heart.

Although not shown, in other embodiments, the valve holder 538 can merely contact and push the valve 500 during deployment, as described for previous embodiments, without securing the inner frame 550 to the valve holder 538. In such embodiments, in some instances, radial expansion of the inner frame 550 can be restricted by the inner sheath 508 when the inner frame 550 is disposed therein.

In this embodiment a first actuation wire 576, a second actuation wire 574, a third actuation wire 576 and a fourth actuation wire 577 are each coupled to the outer frame assembly 510. More specifically, the outer frame 550 of the outer frame assembly 510 includes loops 562 through which the actuation wires 574-577 can be threaded or received therethrough. In this embodiment, the outer frame 520 includes 12 loops 562 and each actuation wire 574-577 is threaded through 3 of the loops 562. In other embodiments, there can be a different number of loops disposed on the outer frame 520 and there can be a different number of actuators. Further, each actuation wire can be threaded or received through a different number of loops than shown for this embodiment.

When the valve 500 is disposed within the delivery system 505 as shown, for example, in FIG. 27, the actuation wires 574-577 each extend from the outer frame 520 proximally within the lumen 582 of the outer sheath and along an outside wall of the inner sheath 508, are tucked or placed behind one or more seals 581 or other holding device, and pinned by an elongate pinning member 578-1, 578-2, 578-3, 578-4 (collectively referred to as pinning members 578) to the tube member 503. The seal 581 can be configured such that the actuation wires 574-577 can slide relative to the seal 581 during actuation and deployment of the valve 500 as described in more detail below.

As shown in FIGS. 27 and 32-34, a first end of the actuation wire 574 and a first end of the actuation wire 575 are pinned by a pinning member 578-2, and a first end of the actuation wire 576 and a first end of the actuation wire 577 are pinned by a pinning member 578-1. A second end of the actuation wire 574 and a second end of the actuation wire 576 are pinned by a pinning member 578-4 (not shown in the partial cross-sectional views of FIGS. 27 and 32-34), and a second end of the actuation wire 575 and a second end of the actuation wire 577 are pinned by a pinning member 578-3 (not shown in the partial cross-sectional views of FIGS. 27 and 32-34). The second ends of the actuation wires are shown detached in FIGS. 27 and 32-34 for ease of illustration.

Figure 28:
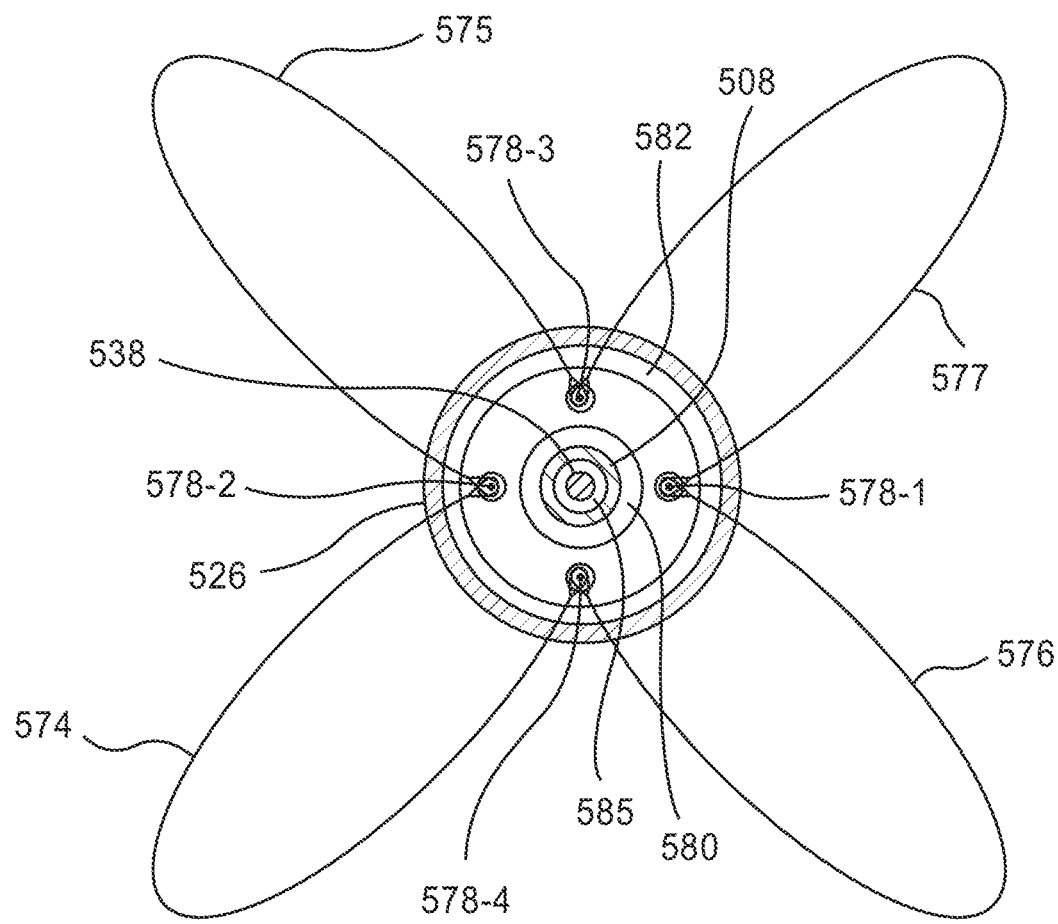
FIG. 28 is a cross-sectional view taken along line 28-28 in FIG. 27 showing the actuation wires coupled to a tube member of the delivery system.
Figure 31A:
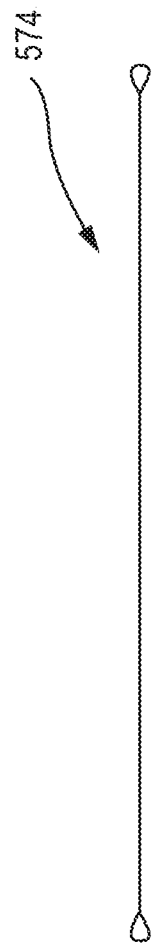
FIGS. 31A-31D are each a side view of a different embodiment of an actuation wire.
Figure 31B:
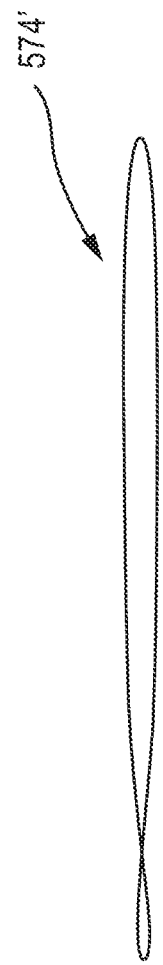
Figure 31C:
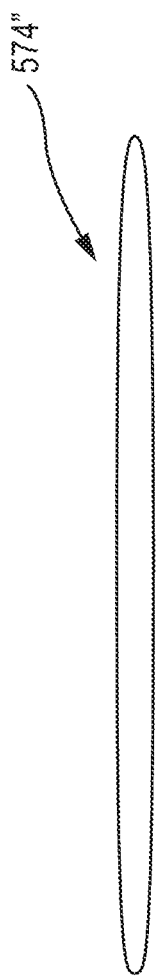
Figure 31D:
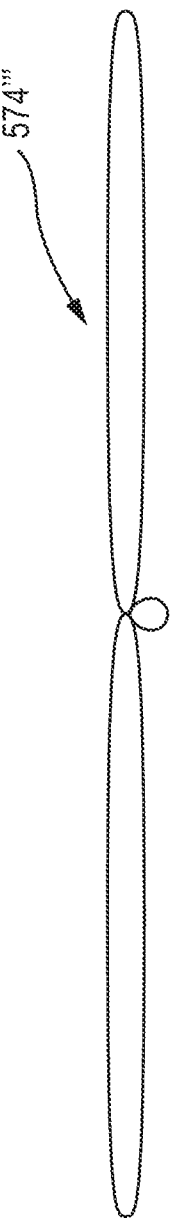

FIG. 28 is a cross-sectional view taken along line 28-28 in FIG. 27 and illustrates the pinning of the actuation wires 574-577. The actuation wires 574-577 are shown unattached to the outer frame for illustration purposes. FIG. 31A illustrates the actuation wire 574 and is representative of the other actuation wires 575-577. FIGS. 31B, 31B and 31C illustrate alternative embodiments for the actuation wires labeled 574', 574" and 574'". As shown in FIG. 31A, the actuation wires 574-577 each include a loop on both ends of the actuation wire, which is pinned by the pinning members 578. In FIG. 31B, the pinning members can pin the smaller loop on one end of the actuation wire 574' and the end of the larger loop on the opposite end of the actuation wire 574'. In FIG. 31C, the actuation wire 575" is in the form of a closed loop and each end of the loop can be pinned by a pinning member. In FIG. 31D, the actuation wire 574'" includes two elongate loops and a center smaller loop. In this embodiment, the actuation wire 574'" can be pinned by three pinning members, a first pinning member can pin an end of one of the larger loops, a second pinning member can pin an end of the other larger loop, and the small loop can be pinned by a third pinning member. In each of the embodiments of FIGS. 31B-31D, a double layer of the actuation wire would be passed or threaded through the loops of the outer frame of the valve. Other alternative configurations can also be used.

As shown in FIGS. 29 and 30A, the multi-lumen tube member 503 defines four pinning member lumens 579-1, 579-2, 579-3, 579-4 (collectively referred to as pinning member lumens 579). The end portions of the actuation wires 574-577 are placed within the circumferential recess or groove 584 defined by the tube member 503, where the pinning members 578 are received through the loops on the ends of the actuation wires 574-577, pinning the actuation wires 574-577 to the tube member 503. Thus, during deployment of the valve 500 within a heart, a user (e.g., physician) can use the tube member 503, to which the actuation wires 574-577 are coupled, to control and/or manipulate movement of the valve 500 as described in more detail below.

Figure 30B:
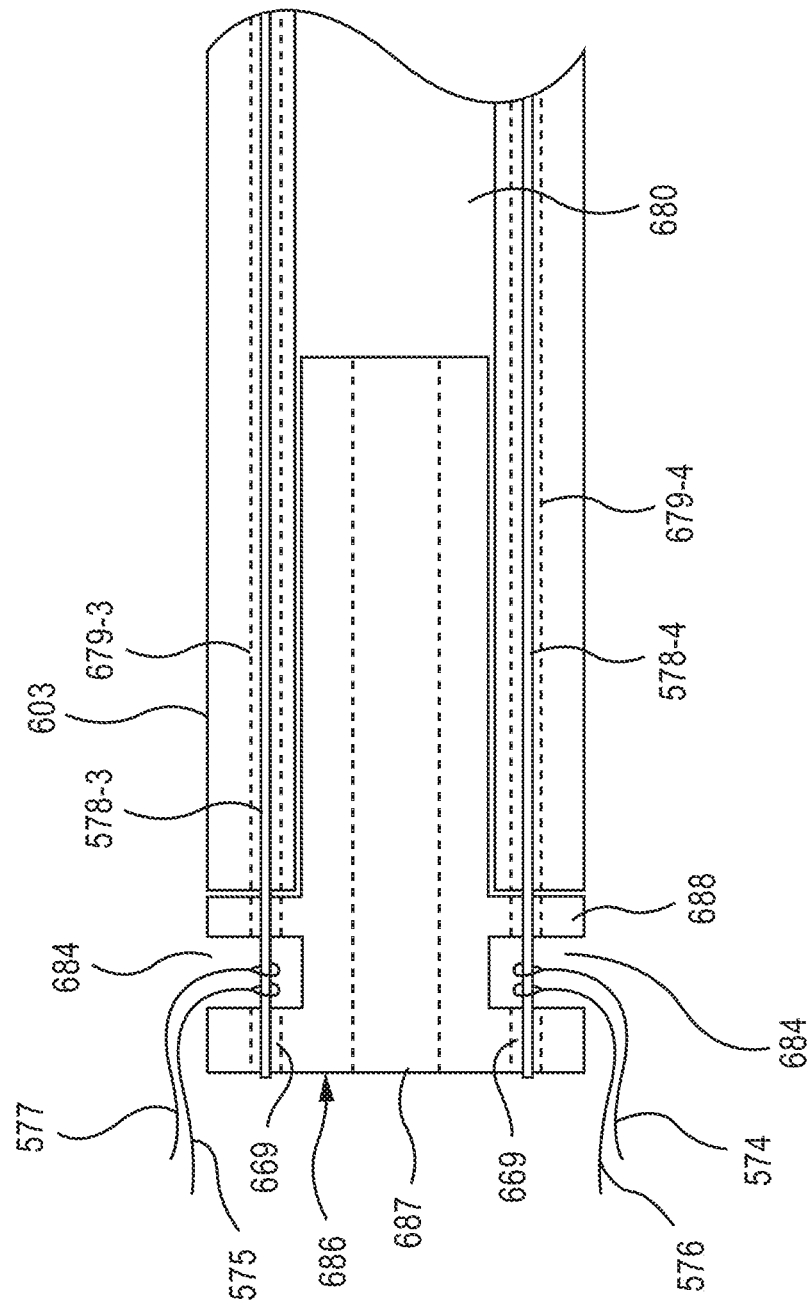
FIG. 30B is a side view of a portion of a multi-lumen tube member according to another embodiment and a distal retention element according to an embodiment.
Figure 30C:
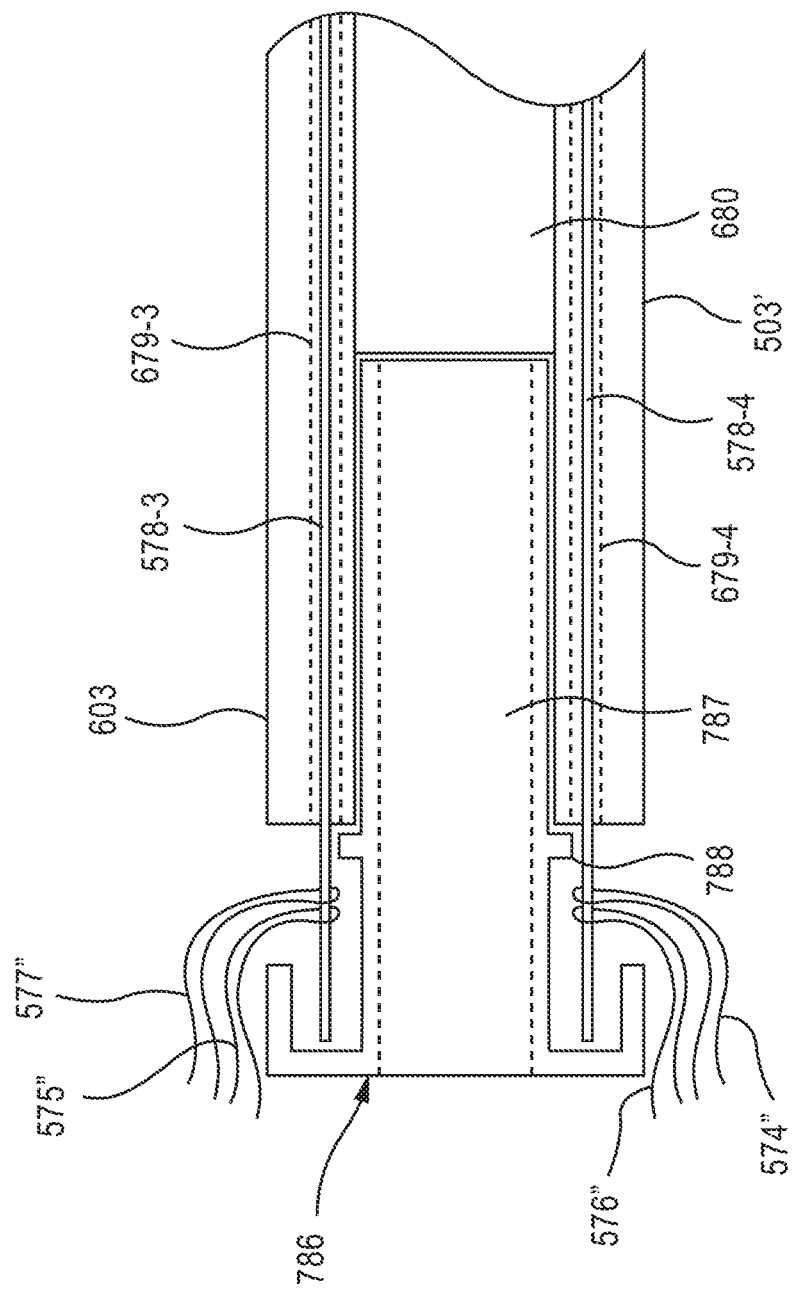
FIG. 30C view of a portion of the multi-lumen tube member of FIG. 30B and a distal retention element, according to another embodiment.

FIGS. 30B and 30C illustrate an alternative embodiment of a multi-lumen tube member 603 that can be used with a distal retention element 686 as shown in FIG. 30B, or a distal retention element 786 as shown in FIG. 30C. The distal retention elements 686 and 786 can be disposed abutting a distal end of the multi-lumen tube member 603 and can define at least in part a recess area to receive the loop ends of the actuation wires, and can provide increased overall strength and durability to the multi-lumen tube member 603 during delivery and deployment of the prosthetic valve. The distal retention element 686, 786 can be formed with the same or a different material as the multi-lumen tube member 603. In some embodiments, it may be desirable for the distal retention element 686, 786 to be formed of a material having greater strength characteristics than the multi-lumen tube member 603. For example, the distal retention element 686, 786 can be formed with a metal or rigid plastic.

As shown in FIGS. 30B and 30C, the multi-lumen tube member 603 (also referred to herein as "tube member") can define a center lumen 680 and multiple pinning member lumens, including pinning member lumens 679-3 and 679-4 (collectively referred to as 679) shown in FIGS. 30B and 30C that can receive therein pinning members, such as pinning members 578-3 and 578-4, respectively. Although not show, the tube member 603 can also define pinning member lumens that can receive pinning members 578-1 and 578-2 as shown for tube member 503 in FIG. 29.

As shown in FIG. 30B, the distal retention element 686 can be received within the lumen 680 and can define a lumen 687 through which the valve holder 538 can be slidably received. Although not shown, the distal retention element 686 can be coupled to the tube member 603 using various different coupling methods. For example, in some embodiments, the distal retention element 686 can be bonded to the tube member 603. In some embodiments the distal retention element 686 can include a feature(s), such as barbs, that allow it to be inserted into the tube member 603, but not removed. In some embodiments the distal retention element 686 can include notches that interlock with a corresponding feature of the tube member 603 and/or the tube member 603 can be reflowed or molded over the retention element 686. Various other coupling methods and/or combinations of securement strategies could be used to couple the distal retention element 686 to the tube member 603. In some embodiments, the distal retention element 686 can extend proximally within the lumen 680 of the tube member 603 and be coupled at a proximal end portion of the tube member 603.

The distal retention element 686 also defines pinning member lumens 669 that align with the pinning member lumens 679 of the multi-lumen tube member 2603 such that the pinning members 578 can be received therein. A proximal shoulder 688 can be disposed abutting a distal end of the multi-lumen tube member 603. The distal retention element 686 also defines a circumferential recess area 684 defined between the proximal shoulder 688 and a distal end portion of the distal retention element 686. As shown in FIG. 30B, the loop ends of the actuation wires 574-577 can be received within the recess area 684 and pinned by the pinning members 578 as described above for multi-lumen tube member 503.

FIG. 30C illustrates a distal retention element 786 disposed abutting the distal end of the multi-lumen tube member 603. As with the previous embodiment, the distal retention element 786 can be received within the lumen 680 and can define a lumen 787 through which the valve holder 538 can be slidably received. The distal retention element 786 can be coupled to the tube member 603 in the same manner as described above for distal retention element 686. The distal retention element 786 also includes a proximal shoulder 788 configured to abut the distal end of the multi-lumen tube member 603. The distal retention element 786 also defines a circumferential recess area 784 that can receive the loop ends of actuation wires 574"-577", which can be pinned by the pinning members 578 (578-3 and 578-4 shown in FIG. 30C). In this example, the actuation wires are configured as a closed loop as shown for actuation wire 574" in FIG. 31C.

Figure 32:
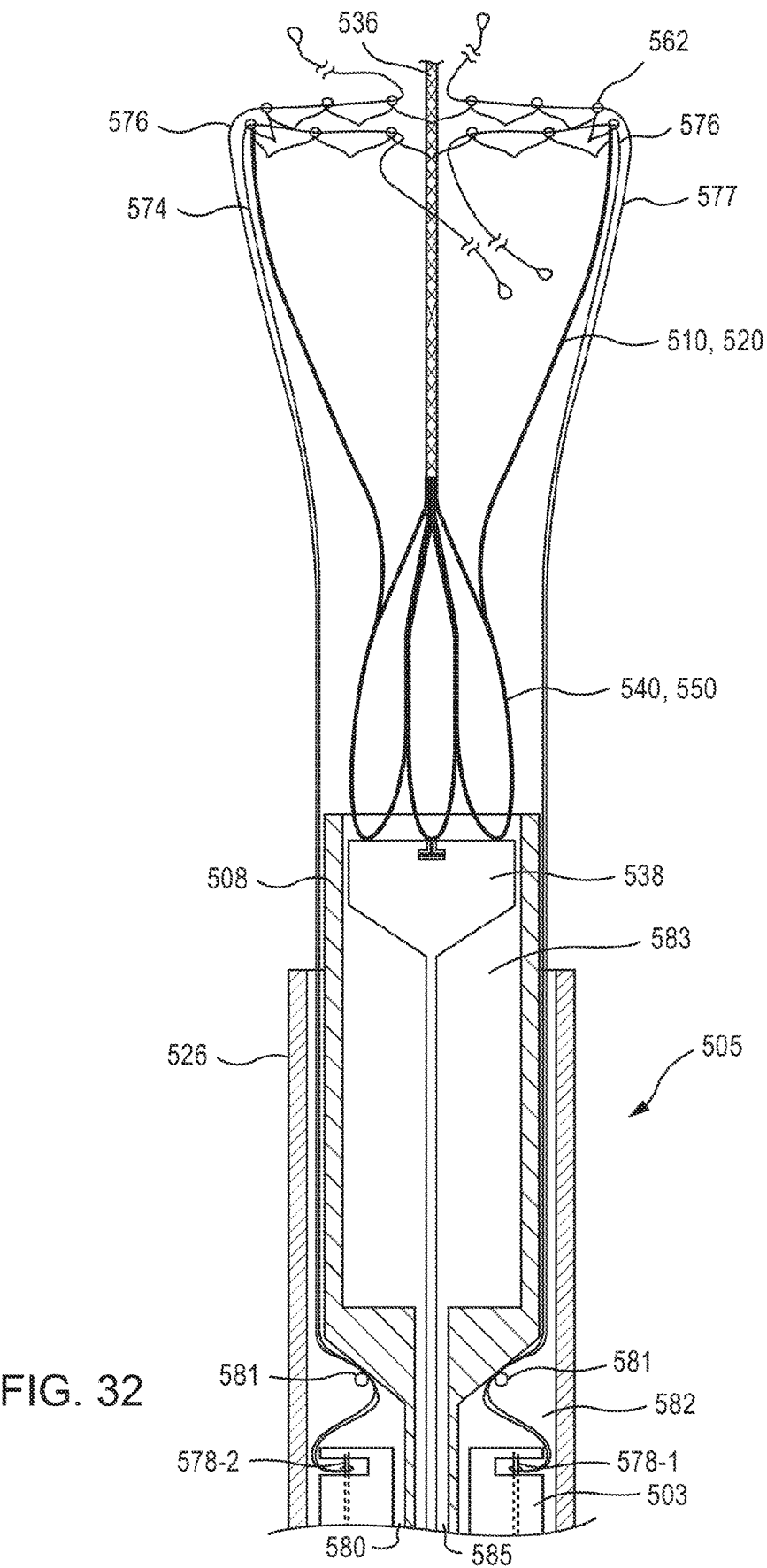
FIG. 32 is a partial cross-sectional side view of the delivery system and prosthetic heart valve of FIG. 27, shown in a first partially deployed configuration.

The procedure to deliver the valve 500 to the heart can be the same as or similar to any of the procedures described herein, in '572 PCT application or in the '305 PCT application incorporated by reference above. For example, the valve 500, disposed within the delivery system 505 in an inverted configuration, can be delivered to the left atrium of the heart in the same or similar manner as described above with reference to FIGS. 43-48 in the '305 PCT application. With the distal end portion of the delivery sheath 526 disposed within the left atrium of the heart, the valve 500 can be deployed outside of the delivery sheath 526. For example, as shown in FIG. 32, the inner sheath 508, valve holder 538 and tube member 503 can be moved distally relative to the outer sheath 526, moving or pushing the valve 500 outside the lumen 582 of the outer sheath 526. In addition, or alternatively, the outer sheath 526 can be moved or pulled proximally, leaving at least a portion of the valve 500 disposed within the heart. In some cases, the tether 536 coupled to the valve 500 can be used to help pull the valve 500 out of the lumen of the outer sheath 526.

Figure 33:
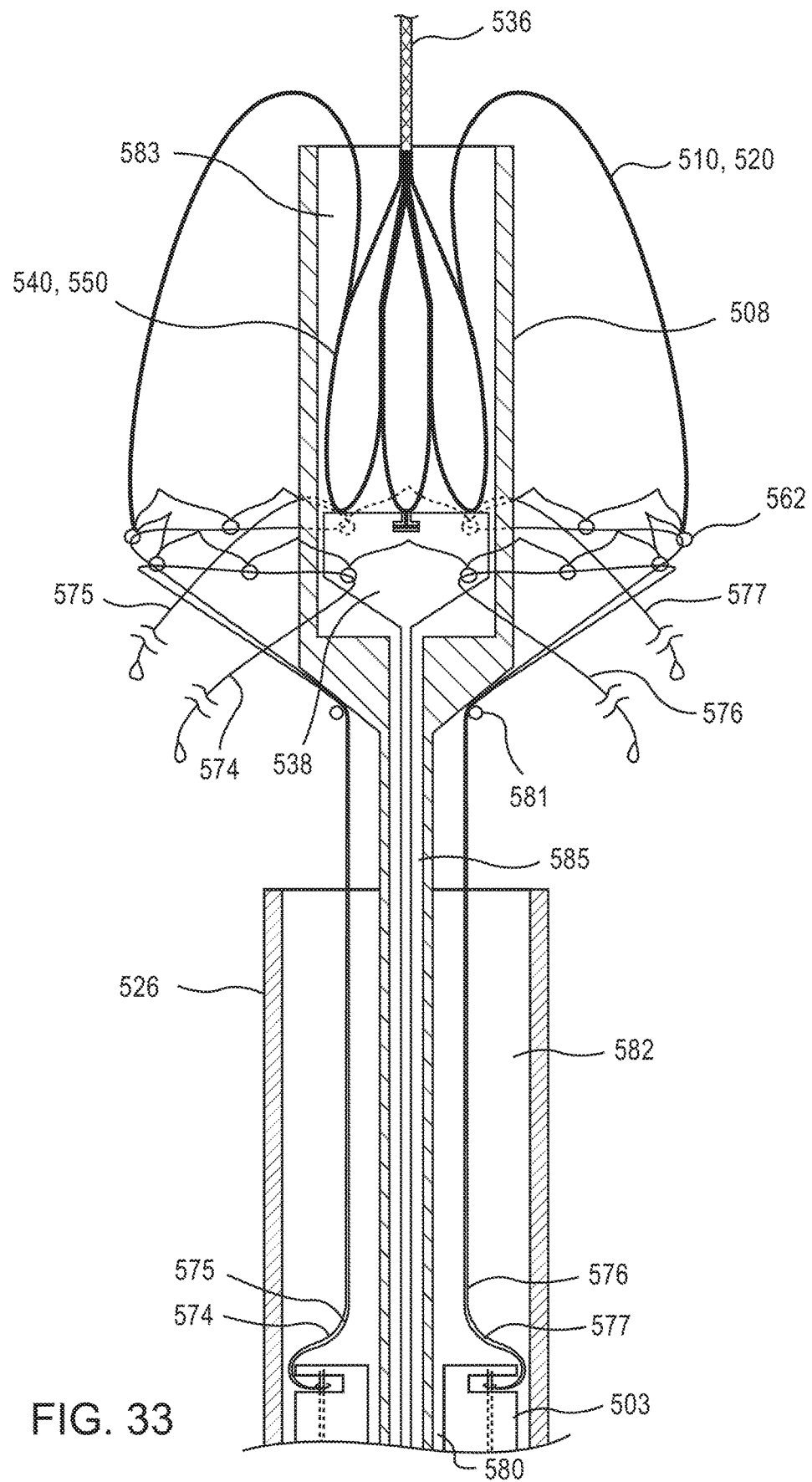
FIG. 33 is a partial cross-sectional side view of the delivery system and prosthetic heart valve of FIG. 27, shown in a second partially deployed configuration.

As described above for previous embodiments, as the outer frame 520 becomes unconstrained by the outer sheath 526, the outer frame 520 can begin to revert to its expanded or uninverted configuration. The actuation wires 575-577 can be used to control the reversion of the outer frame 520. More specifically, the tube member 503 can be pulled proximally such that the actuation wires (pinned to the tube member 503) pull the distally disposed portion of the outer frame 520 proximally (as shown in FIG. 33) in a controlled manner and such that the reversion of the outer frame 520 from its inverted configuration relative to the inner frame 550 can be controlled.

Figure 34:
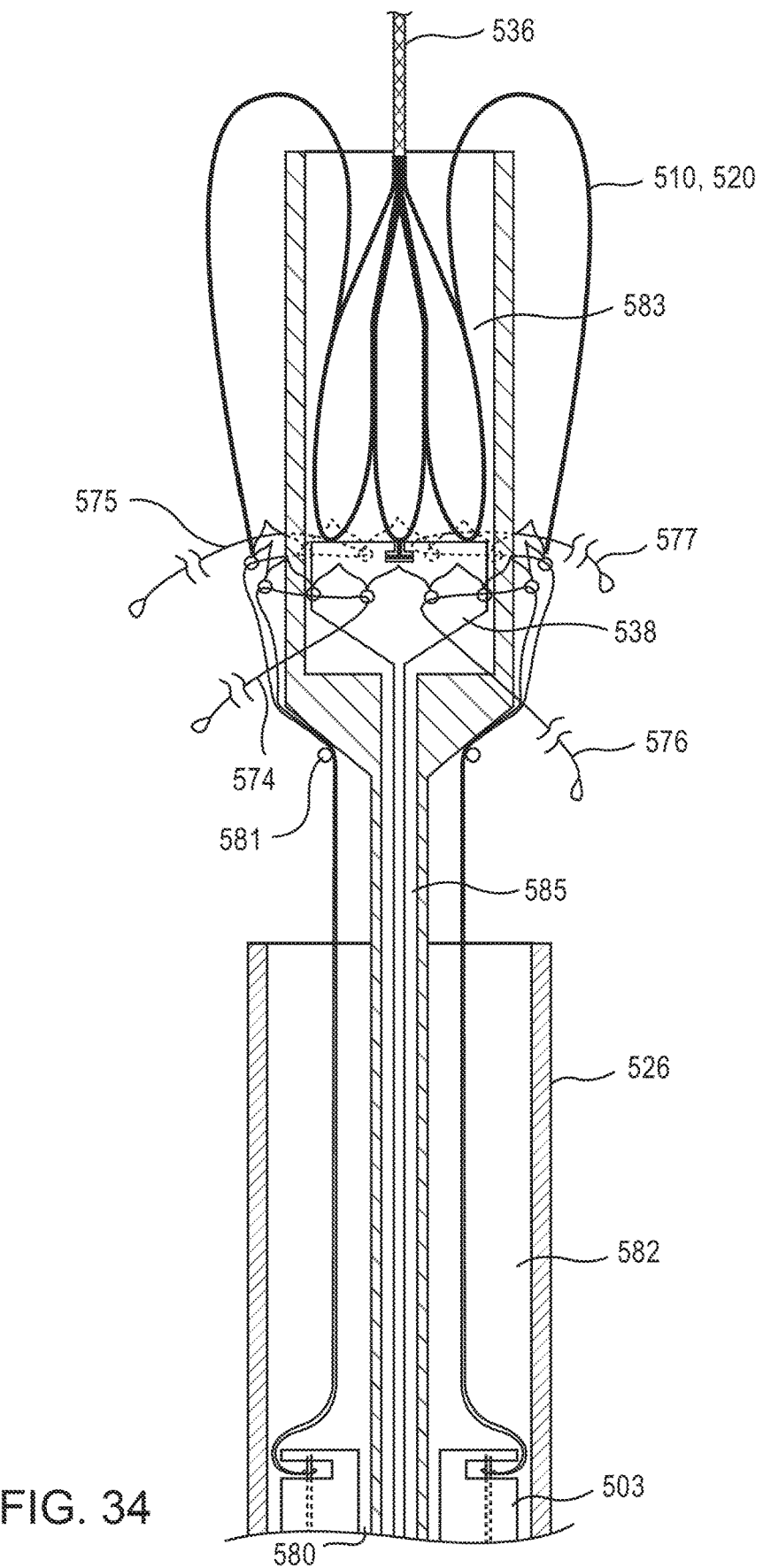
FIG. 34 is a partial cross-sectional side view of the delivery system and prosthetic heart valve of FIG. 27, shown in a third partially deployed configuration.

In addition, in some instances, the actuation wires 574-577 can assist in the articulation and placement of the valve 500 into its destination (e.g., a native annulus of an atrioventricular valve of a heart). For example, as shown in FIG. 34, the actuation wires 574-577 can also be used to constrain, collapse, or otherwise move the valve 500 (e.g., radially compress the outer frame 520 of the valve 500) after the valve 500 exits the outer sheath 526 and is in its reverted, expanded or partially expanded configuration. More specifically, in this embodiment, the tube member 503 with the actuation wires 574-577 pinned thereto, can be manipulated by a user to move or urge the outer frame to a more compressed configuration (as shown in FIG. 34) by pulling or moving the tube member 503 proximally. This may be desirable, for example, to reposition the valve 500 within the heart before fully deploying the valve 500.

Referring back to FIG. 33, when the outer frame 520 of the valve 500 is disposed in its non-inverted and at least partially expanded configuration, and is in a desired position within the heart, the inner frame 550 can be deployed. As described above for valve 400, to decouple the inner frame 550 from the valve holder 538, the valve holder 538 can be moved distally and/or the inner sheath 208 can be moved proximally such that the valve holder 238 is disposed outside of the lumen 583 of the inner sheath 508. As such, the couplers 506 can be released from the recesses 504 releasing or decoupling the inner frame 550 from the valve holder 538. In some embodiments, the tether 536 can be pulled to help move the inner frame 550 outside of the inner sheath 508. When the inner frame 550 is released from the valve holder 538 and disposed outside the inner sheath 508, the inner frame 550 can assume its biased expanded configuration.

Figure 35:
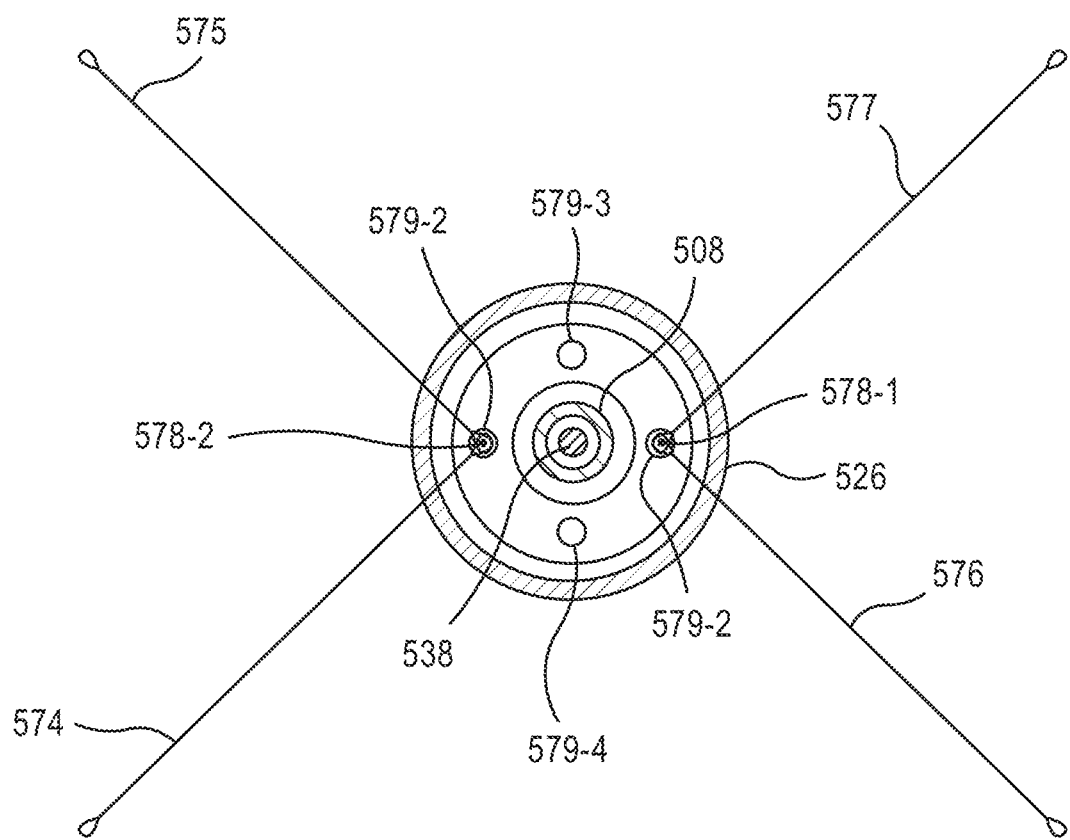
FIG. 35 is a cross-sectional view taken along line A-A in FIG. 27 showing the actuation wires in a partially released position.

The actuation wires 574-577 can also be released or decoupled from the outer frame 520 before or after the inner frame 550 is released from the valve holder 538. To decouple the actuation wires 574-577 from the outer frame 520, one end of each of the actuation wires 574-577 can be unpinned or decoupled from the tubular member 503. For example, as shown in FIG. 35, the pinning member 578-3 (See FIG. 28) can be withdrawn proximally from groove 584 such that the second end of the actuation wire 577 and the second end of the actuation wire 575 are each released or unpinned from the tube member 503, but remain pinned by pinning members 578-2 and 578-1, respectively. Similarly, the pinning member 578-4 (see FIG. 28) can be withdrawn proximally from groove 584 such that the second end of the actuation wire 574 and the second end of actuation wire 576 can each be released or unpinned from the tube member 503, but remain pinned by pinning members 578-2 and 578-1, respectively. With one end of each of the actuation wires 575-577 coupled to the tube member 503 (via pinning members 578-1 and 578-2 in this example), the tube member 503 can be pulled proximally, which in turn will pull the opposite ends of the actuation wires 574-577 out of the loops 562 of outer frame 520. Thus with the actuation wires 574-577 detached from the outer frame 520, the outer frame can assume a biased expanded or partially expanded configuration.

Although in the above example, the pinning members 578-3 and 578-4 are shown withdrawn to release the ends of the actuation wires 574-577, alternatively, the pinning members 578-1 and 578-2 can be withdrawn leaving the actuation wires 574-577 pinned by pinning members 578-3 and 578-4. Further, the actuation wires 574-577 can be decoupled from the outer frame 520 at any suitable sequence or time period within the procedure. For example, in some instances it may be desirable for the actuation wires 574-577 to be released after the valve 500 has at least partially exited the delivery sheath 526 but before the valve 500 is seated within the native annulus of the atrioventricular valve. In other instances, for example, the actuation wires 574-577 can be released after the valve 500 has at least partially exited the outer delivery sheath 526 and after the valve 500 is seated within the native annulus of the atrioventricular valve.

FIGS. 36A-38 illustrate another embodiment of a delivery system 805 (also referred to as a "delivery device") that can be used to deliver and deploy a prosthetic heart valve 800 (shown schematically in FIG. 37) within a heart in a procedure similar to or the same as the procedures described with respect to other embodiments described herein and embodiments described in the '305 PCT application. Thus, some details regarding the valve and procedures performed therewith are not described herein. It should be understood that for features and functions not specifically discussed, those features and functions can be the same as or similar to the valves described herein (e.g., the valve 500) and/or in the '305 PCT application. The valve 800 can be constructed the same as or similar to, and function the same as or similar to any of the valves described herein and/or in the '305 PCT application. For example, the valve can include an outer frame assembly 810 that has an outer frame, an inner valve assembly 840 that has an inner frame, and a tether (not shown) coupled to the inner valve assembly. The delivery system 805 can include the same or similar components as delivery system 505 described above. For example, the delivery system 805 can include an outer delivery sheath 826 and a valve holder 838 (also referred to as a "pusher"). In this embodiment, the delivery system 805 includes an elongate tube member 815 (also referred to as "tube" or "tube member") which can be slidably disposed within a lumen 882 of the delivery sheath 826 and can be coupled to a retention device (described below) that can be used to secure and release actuation wires 874, 875 and 876 (875 only shown in FIGS. 41A and 41B) as described in more detail below. The valve holder 838 can be coupled to an elongate member 837 that can be movably disposed within a lumen 880 defined by the elongate tube member 815 and a lumen defined by a retention device 860 described below.

As with other embodiments described herein and embodiments of the '305 PCT application, the delivery system 805 can be used to deliver the valve 800, which can be moved from a biased expanded configuration to an inverted configuration for delivery of the valve to the heart. To deploy the valve 800 within a heart, the outer frame of the valve 800 can be moved to an inverted configuration relative to the inner frame as described above for previous embodiments and placed within a distal end portion of the lumen 882 of the delivery sheath 826 and/or a lumen of an inner sheath (not shown) that can be movably disposed within the lumen 882 of the outer delivery sheath 826, such that the valve 800 is compressed or collapsed within the delivery sheath 826 as shown schematically in FIG. 36C.

The inner frame of the valve 800 can be releasably coupled to the valve holder 838 via couplers (not shown) that are received within corresponding recesses (not shown) defined by the valve holder 838 in the same or similar manner as described above for delivery system 405 (see, e.g., FIGS. 26A-26C). In this manner, the valve holder 838 can be used to hold the valve to aid in the control and manipulation of the valve as it is delivered and deployed. For example, as described above for valves 400 and 500, an inner diameter of the outer delivery inner sheath 826 or an inner diameter of an inner sheath (not shown) in which the valve is disposed for delivery, can be sized such that when the valve holder 838 and valve are disposed therein, the couplers are unable to exit the recesses. In other words, the inner walls of the inner sheath or delivery sheath maintain the couplers within the recesses. When the valve is moved outside of the inner sheath or delivery sheath, the couplers will be able to freely exit the recesses, releasing the inner frame of the valve from the valve holder 838. In some embodiments, the valve holder 838 can include an inner member that can be used to maintain the couplers within the recesses of the valve holder 838, rather than a component on the outer surface of the valve holder 838 as described for delivery systems 405 and 505. For example, the inner member of the valve holder 838 can be moved distally outside of the valve holder 838 to release the couplers from the recesses and moved back proximally within the valve holder 838 to secure the couplers in the recesses.

In this embodiment, the elongate tube member 815 is coupled to a retention device 860 that includes retention components or members that are coupled together coaxially and can be actuated to secure and release actuation wires coupled to the delivery system 805. FIGS. 36A-38 illustrate three retention components or members, but in other embodiments, more or less than three retention components can be included. More specifically, the retention device 860 includes a first or proximal retention member 864 that is fixedly coupled to a distal end portion of the tube member 815, a second or center retention member 866 that is movably coupled to the proximal retention member 864 and a third or distal retention member 868 that is movably coupled to the center retention member 866 and movably coupled to the proximal retention member 864. The center retention member 866 can be coupled to the proximal retention member 864 via a first actuation rod or rods 865, and the distal retention member 868 can be coupled to the center retention member 866 and to the proximal retention member 864 via a second actuation rod or rods 867. The actuation rods 865 and 867 can extend to a proximal end of the delivery device 805 and be operably coupled to a handle assembly 818 (see FIG. 38). Although two actuation rods 865 and two actuation rods 867 are shown in FIGS. 36A-38, in alternative embodiments, the delivery system can include a single actuation rod 865 and a single actuation rod 867 or more than two actuation rods 865, 867. In some embodiments, two actuation rods 867 are fixedly attached to the distal retention member 868, and a single actuation rod 865 is fixedly attached to the center retention member 866. More specifically, the actuation rods 867 are attached to the distal retention member 868, extend through lumens/passageways defined by the center retention member 866 and through lumens defined by the proximal retention member 864 such that the distal retention member 868 can be moved relative to the center retention member 866 and the proximal retention member 864. The actuation rod 865 is fixedly attached to the center retention member 864, and extends through a lumen/passageway defined in the proximal retention member 864 such that the center retention member 866 can be moved relative to the proximal retention member 864. The proximal retention member 864 can be fixedly attached to the tube member 815 with a connecting rod (not shown) such that the proximal retention member 864 can move with the tube member 815.

The retention device 860 also defines a lumen through which the valve holder 838 can be movably disposed. For example, each of the proximal retention member 864, the center retention member 866 and the distal retention member 868 can define a lumen and the valve holder 838 and elongate member 837 can be movably disposed within each lumen.

Multiple pins 898 are fixedly attached to the center retention member 866 and include a proximal portion 878 (also referred to as "pin" or "pin portion") that extends proximally from the center retention member 866 and a distal portion 888 (also referred to as "pin" or "pin portion") that extends distally from the center retention member 866. In some embodiments, the pins 898 extend through lumens (not shown in FIGS. 36A-38) defined by the center retention member 866. The proximal and distal pin portions 878 and 888 can be used to releasably hold actuation wires 874, 875 and 876 to the delivery device 805 in a similar manner as described above for delivery system 505 and pins 578. For example, the pins 878 can be received within apertures or lumens 863 defined by the proximal retention member 864 and the pins 888 can be received within apertures or lumens 861 defined by the distal retention member 868. Pins 878 and pins 888 can be formed as separate pins and attached to the center retention member 866 or can be formed as a single component with the pins 878 extending proximally from the center retention member 866 and the pins 888 extending distally from the center retention member 866. For example, the pins 878, 888 can be a single component that extends through an opening in the center retention member 866 and is attached (e.g., welded) to the center retention member 866, or is otherwise attached to the center retention member 866 (without passing through an opening). The pins 878, 888 can be for example, welded to the center retention member 866. Only two pins 878 and two pins 888 are shown in FIGS. 36A-38, but a third pin 878 and a third pin 888 are also included to pin the actuation wires 874, 875, 876. Thus, in this embodiment, there are three actuation wires and three pins 878 and three pins 888. In other embodiments there can be more or less than three actuation wires and more or less than three pins 878 and three pins 888.

Figure 48:
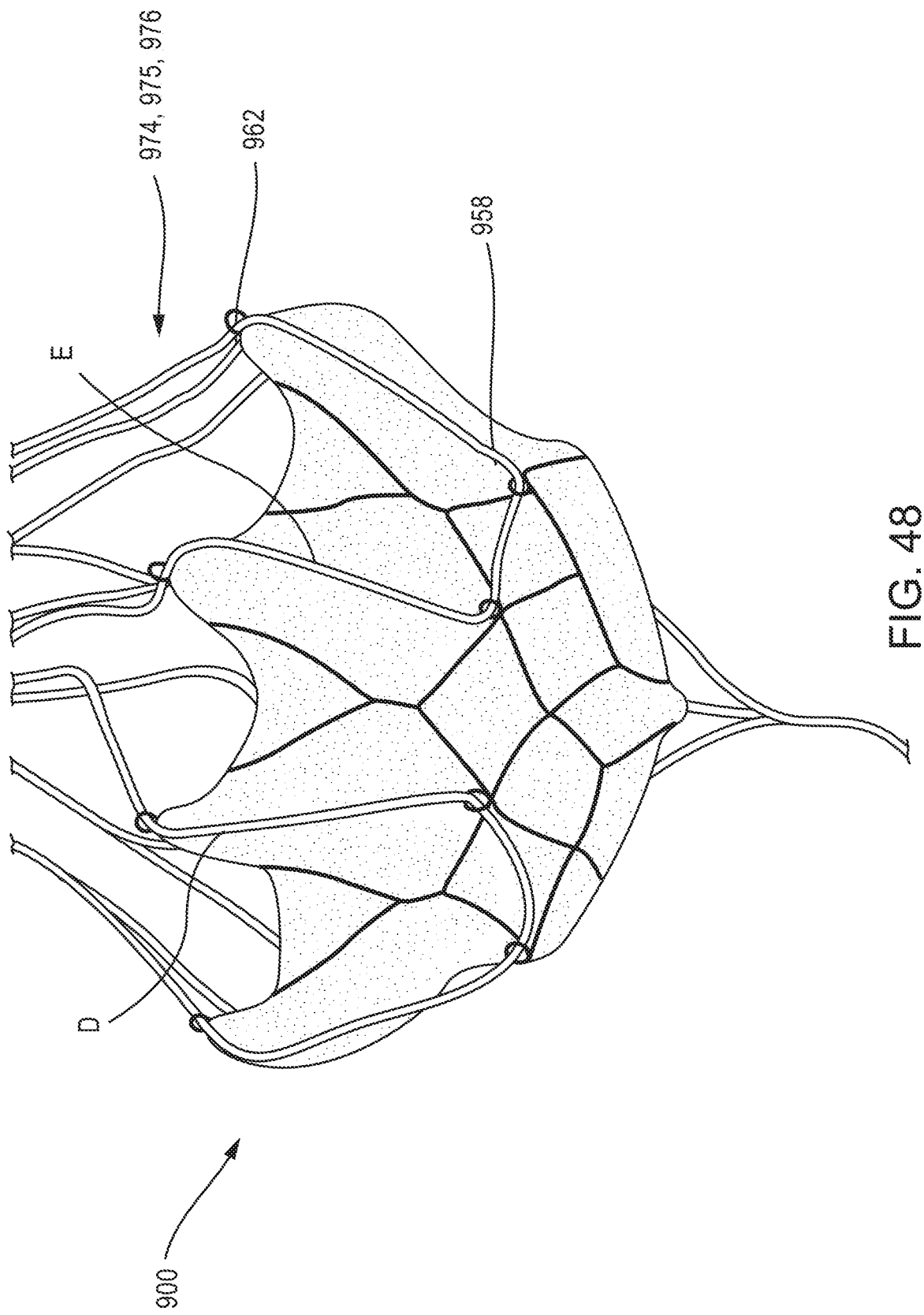
FIG. 48 is a side view of the prosthetic valve of FIG. 46 shown in an expanded configuration.

As with previous embodiments, multiple actuation wires can be coupled to the outer frame assembly of the prosthetic valve and used to help revert and manipulate the prosthetic valve into a desired position within the heart, and then can be released from the valve when the desired positioning has been achieved. More specifically, the outer frame of the valve can include loops through which the actuation wires 874-877 can be threaded or received therethrough in the same or similar manner as described herein (e.g., with respect to valve 500) and/or in the '305 PCT application. For example, if the outer frame includes 12 loops, each actuation wire 874, 875 and 876 can be threaded through 4 of the loops. In other embodiments, there can be a different number of loops disposed on the outer frame and there can be a different number of actuation wires. Further, each actuation wire can be threaded or received through a different number of loops than shown for this embodiment. In some embodiments, the actuation wires can be coupled to (e.g., threaded through) the outer frame at a second set of loops disposed at a location between the free end of the outer frame and where the outer frame is attached to the inner frame. An example of such an embodiment is shown in FIG. 48.

Figure 40:
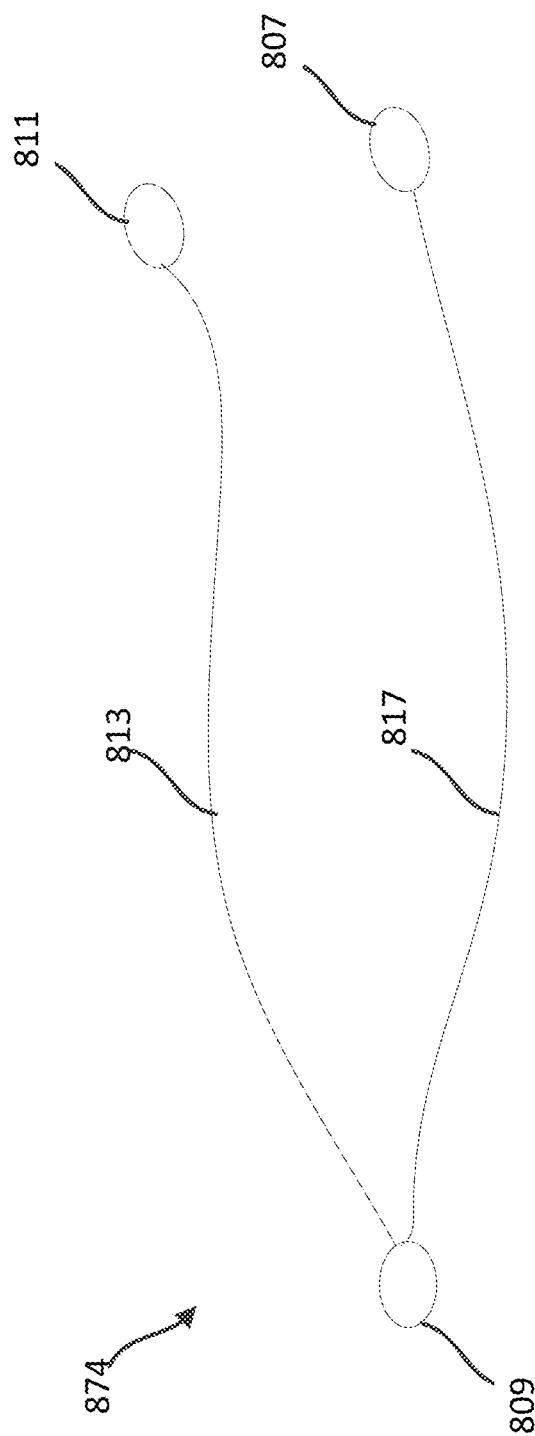
FIG. 40 is a top view of an actuation wire according to an embodiment.

FIG. 40 illustrates an embodiment of an actuation wire 874 that can be used with delivery device 805. It should be understood that this is just one example of a configuration of an actuation wire that can be used. Other alternative embodiments can be used, such as, for example, those described above with reference to FIGS. 31A-31D and described below with reference to FIGS. 46 and 53-57. The actuation wire 874 includes a center loop 809 and two end loops 807 and 811. The center loop 809 is connected to the end loop 807 by a strand 817 and the center loop 809 is connected to the end loop 811 by a strand 813. Actuation wires 875 and 876 can be constructed the same as actuation wire 874 or have a different construction. As shown in FIGS. 36B-38, the end loops 807 and 811 can be pinned by pins 878 between the center retention member 866 and the distal retention member 868 and the center loops 809 can be pinned by pins 888 between the center retention member 866 and the proximal retention member 864 More specifically, FIGS. 36B-38 show the center loop 809 of actuation wire 874 pinned by a pin 878 and the end loops 807 and 811 pinned by a pin 888, and the center loop 809 of the actuation wire 876 pinned by a pin 878 and the end loops 807 and 811 pinned by pins 888. In some embodiments, the actuation wires 874-876 are also routed through apertures (not shown in FIGS. 36A-38) defined by the valve holder 838. This helps maintain the actuation wires 874-876 close to the valve holder 838 and within the lumen of the delivery sheath 826 during delivery.

Figure 41A:
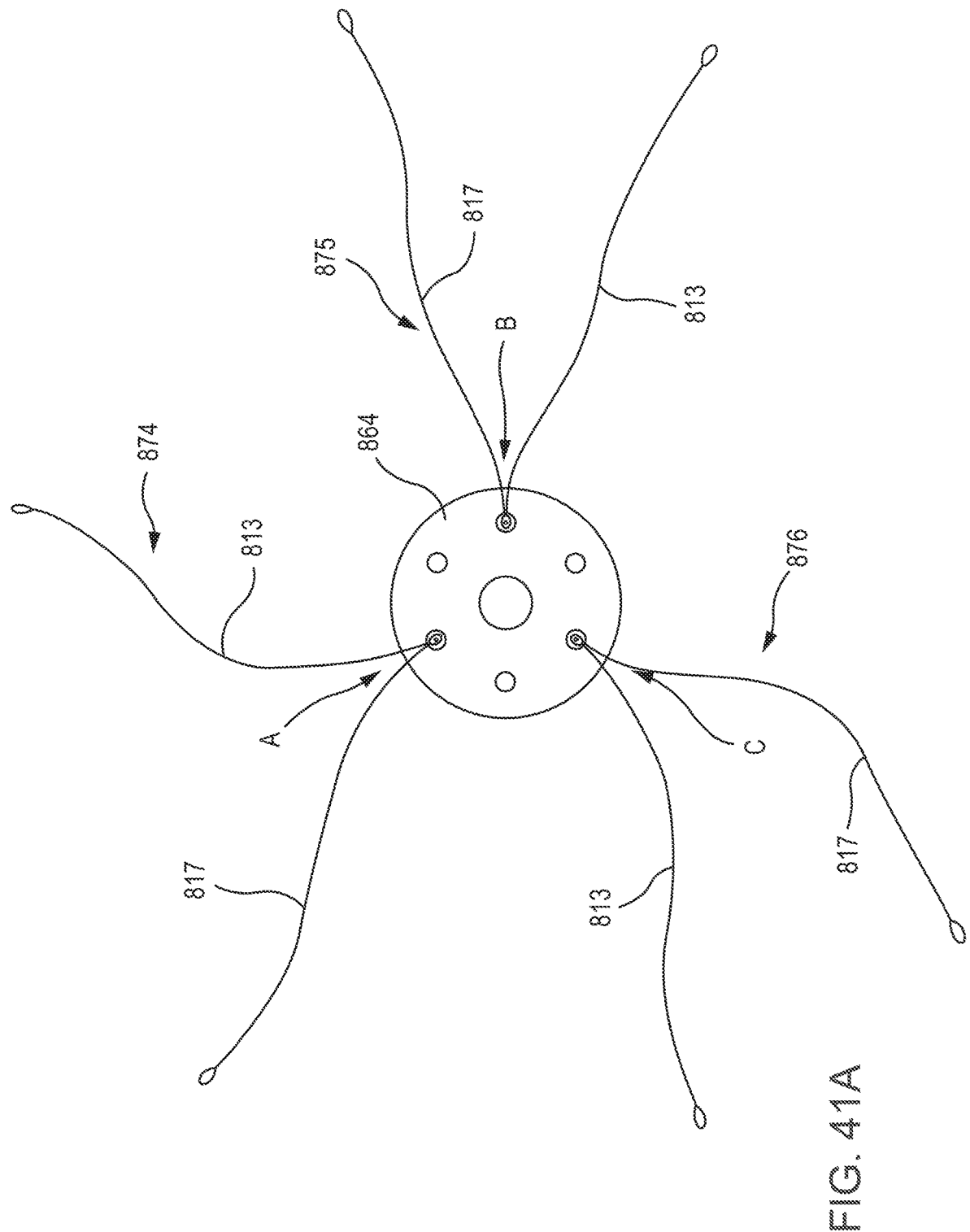
FIG. 41A is an end view of a portion of the delivery system of FIGS. 36A-38 illustrating the pinning of the center loops of the actuation wires to the proximal retention member of the retention device.
Figure 41B:
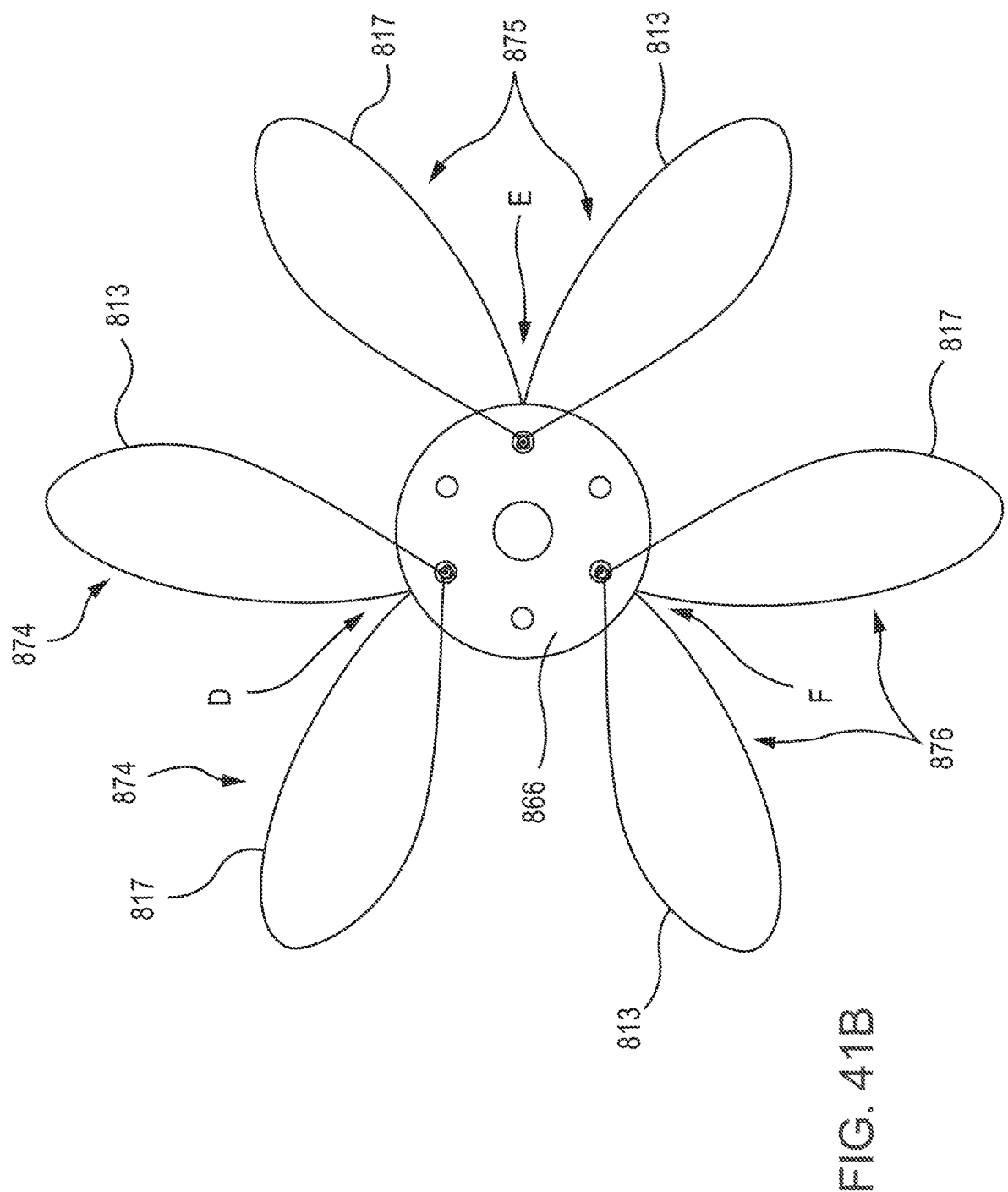
FIG. 41B is an end view of a portion of the delivery system of FIGS. 36A-38 illustrating the pinning of the end loops of the actuation wires to the center retention member of the retention device.
Figure 42:
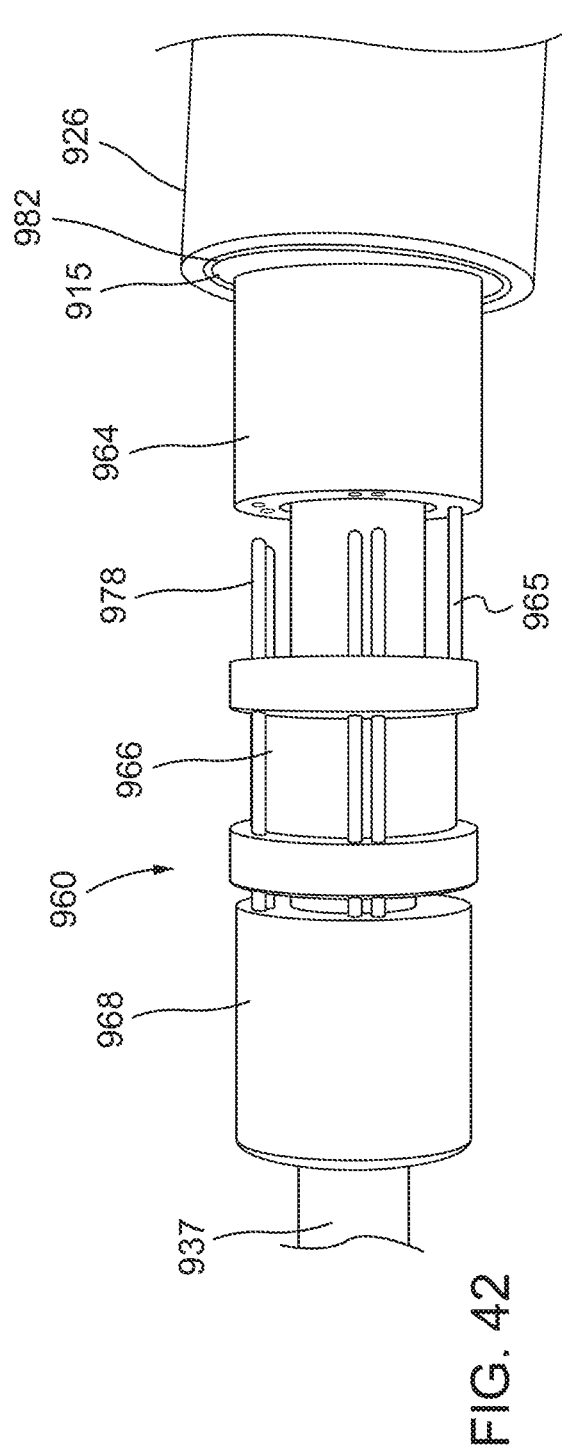
FIG. 42 is a side view of a portion of a delivery system, according to an embodiment and shown in a first configuration.

FIGS. 41A and 41B illustrate the pinning of the loops of the actuation wires 874, 875 and 876. An end view of the proximal retention member 864 is shown in FIG. 41A and an end view of the center retention member 866 (distal retention member 868 is not shown in FIGS. 41A and 41B) to help illustrate how the loops and actuation wires are routed/pinned to the retention device 860. The routing of the actuation wires through the prosthetic valve is not shown in FIGS. 41A and 41B for ease of illustration. As shown in FIG. 41A, the center loop 809 of actuation wire 874 is pinned by a pin 878 at A, the center loop 809 of actuation wire 875 is pinned by a pin 878 at B and the center loop 809 of the actuation wire 876 is pinned by a pin 878 at C. As shown in FIG. 41B, the end loop 807 and the end loop 811 of actuation wire 874 are both pinned by a pin 888 at D; the end loop 807 and the end loop 811 of actuation wire 875 are both pinned by a pin 888 at E, and the end loop 807 and the end loop 811 of actuation wire 876 are both pinned by a pin 888 at F.

Figure 36A:
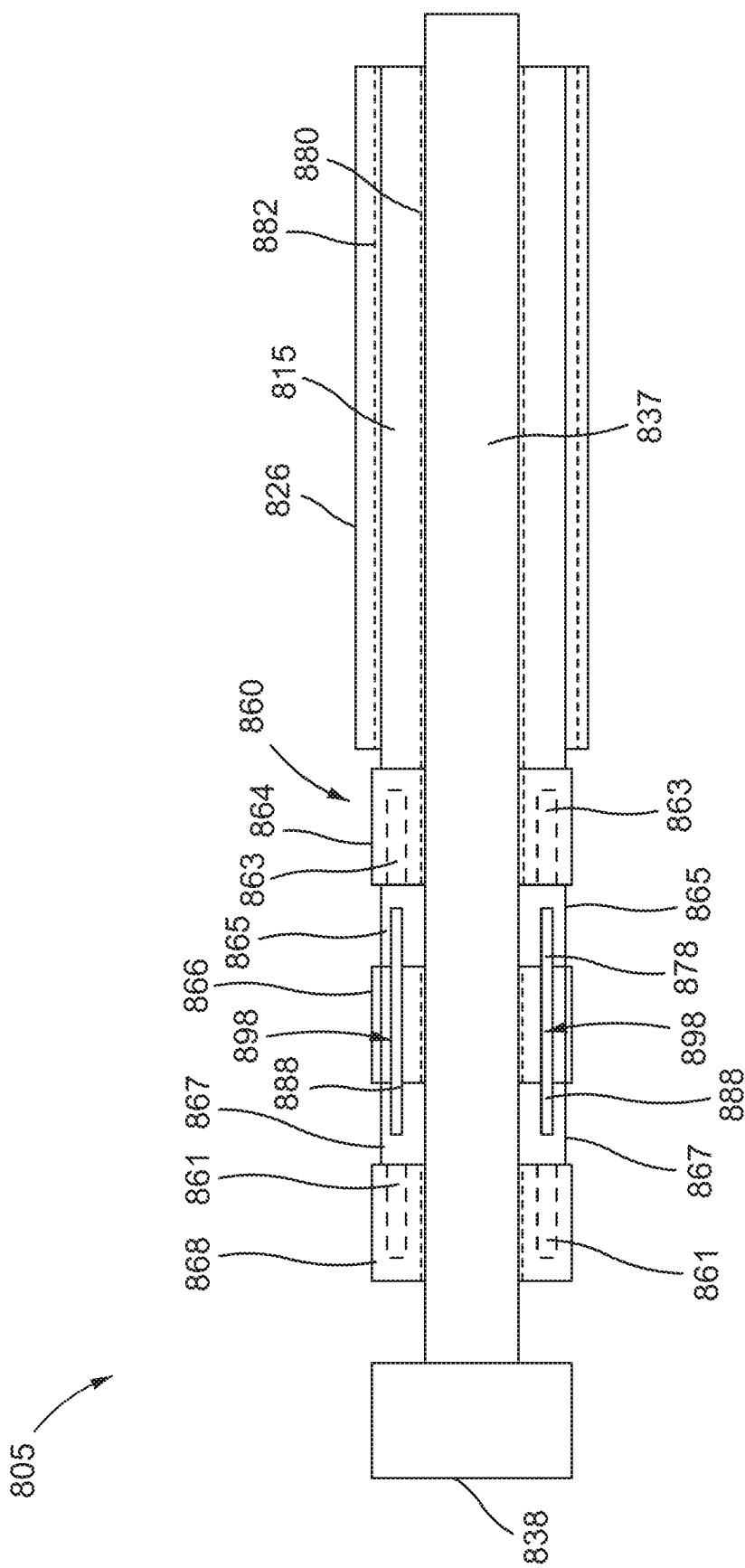
FIG. 36A is a schematic illustration of a side view of a delivery system according to another embodiment, shown in a first configuration.
Figure 36B:
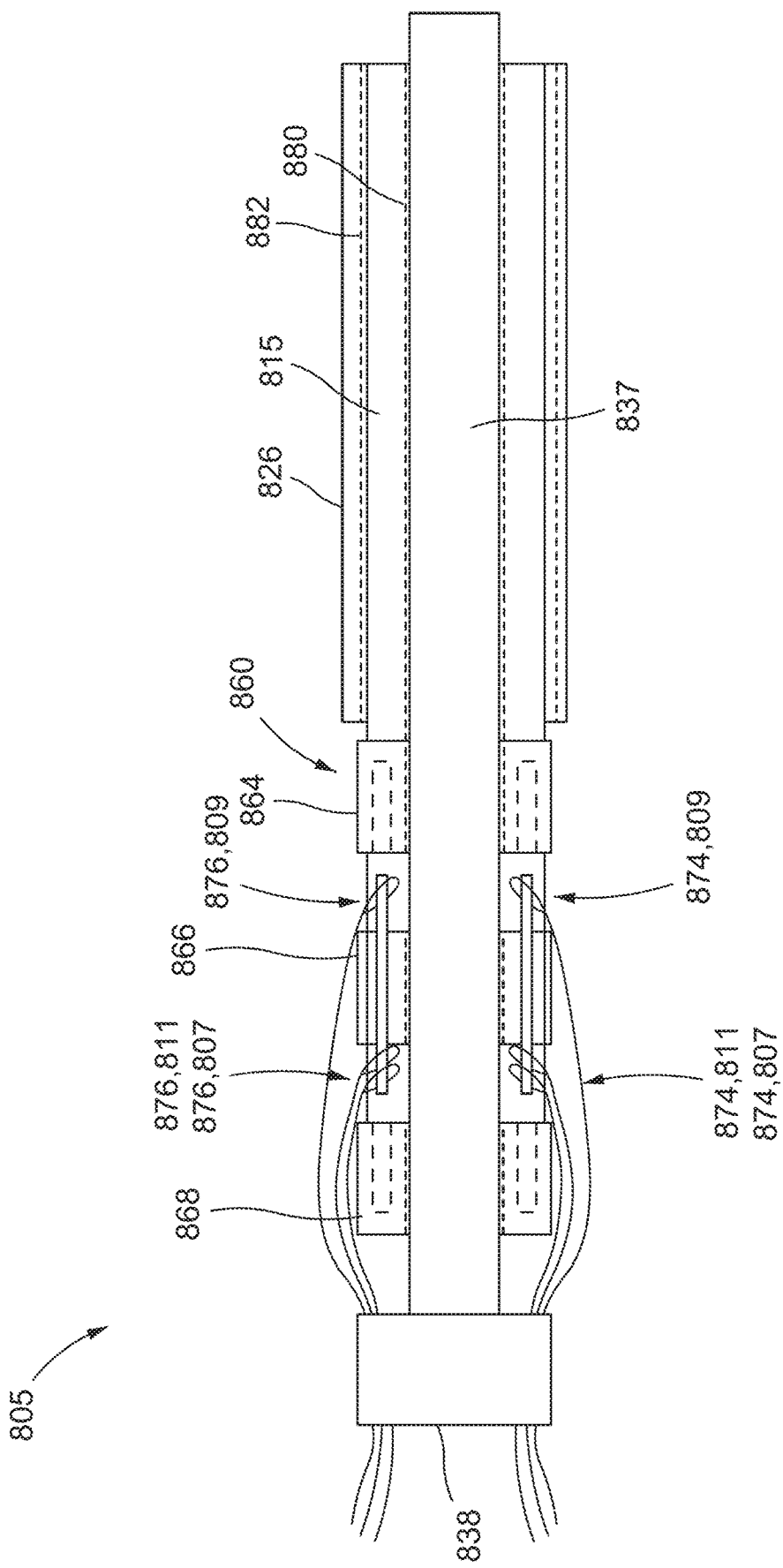
FIG. 36B is a schematic illustration of a side view of the delivery of FIG. 36A, shown with actuation wires coupled thereto.
Figure 36C:
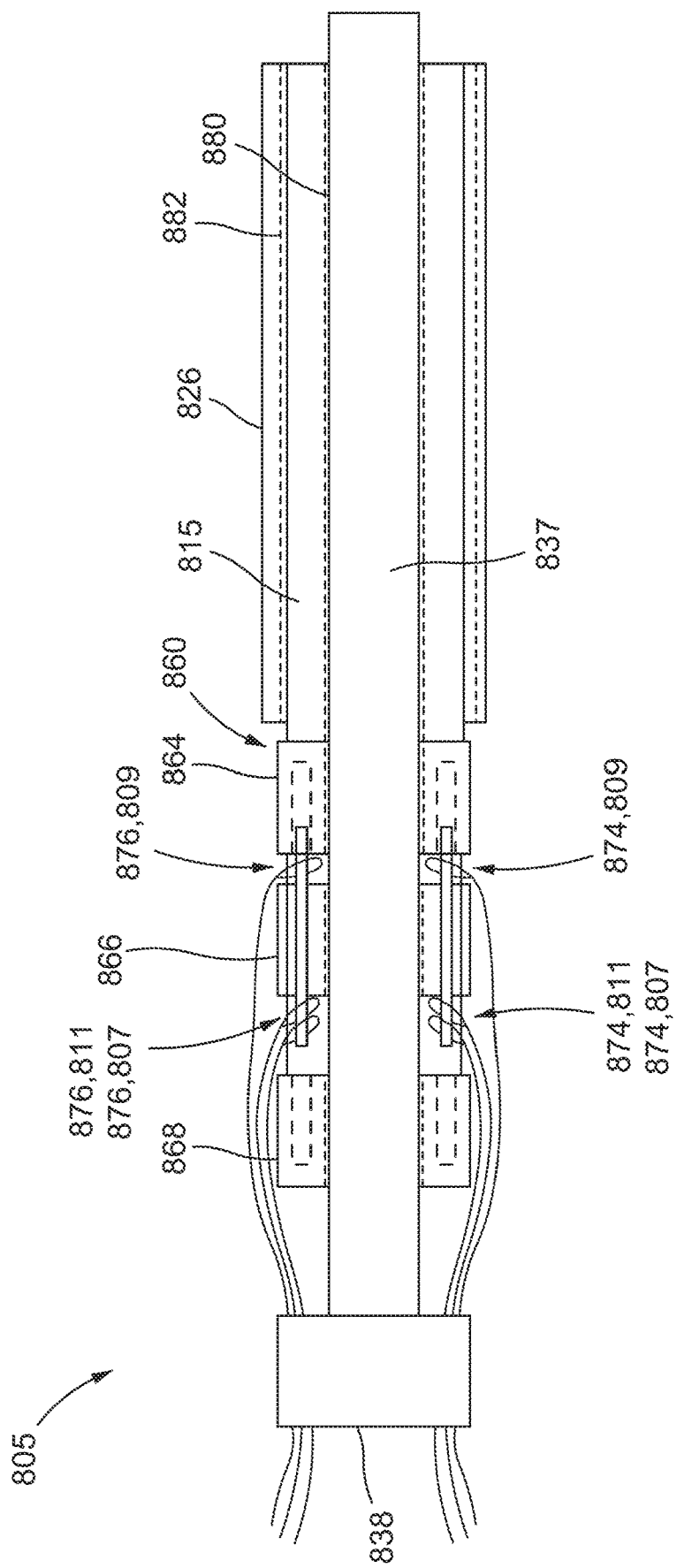
FIG. 36C is a schematic illustration of a side view of the delivery system and actuation wires of FIG. 36A, shown in a second configuration.
Figure 36D:
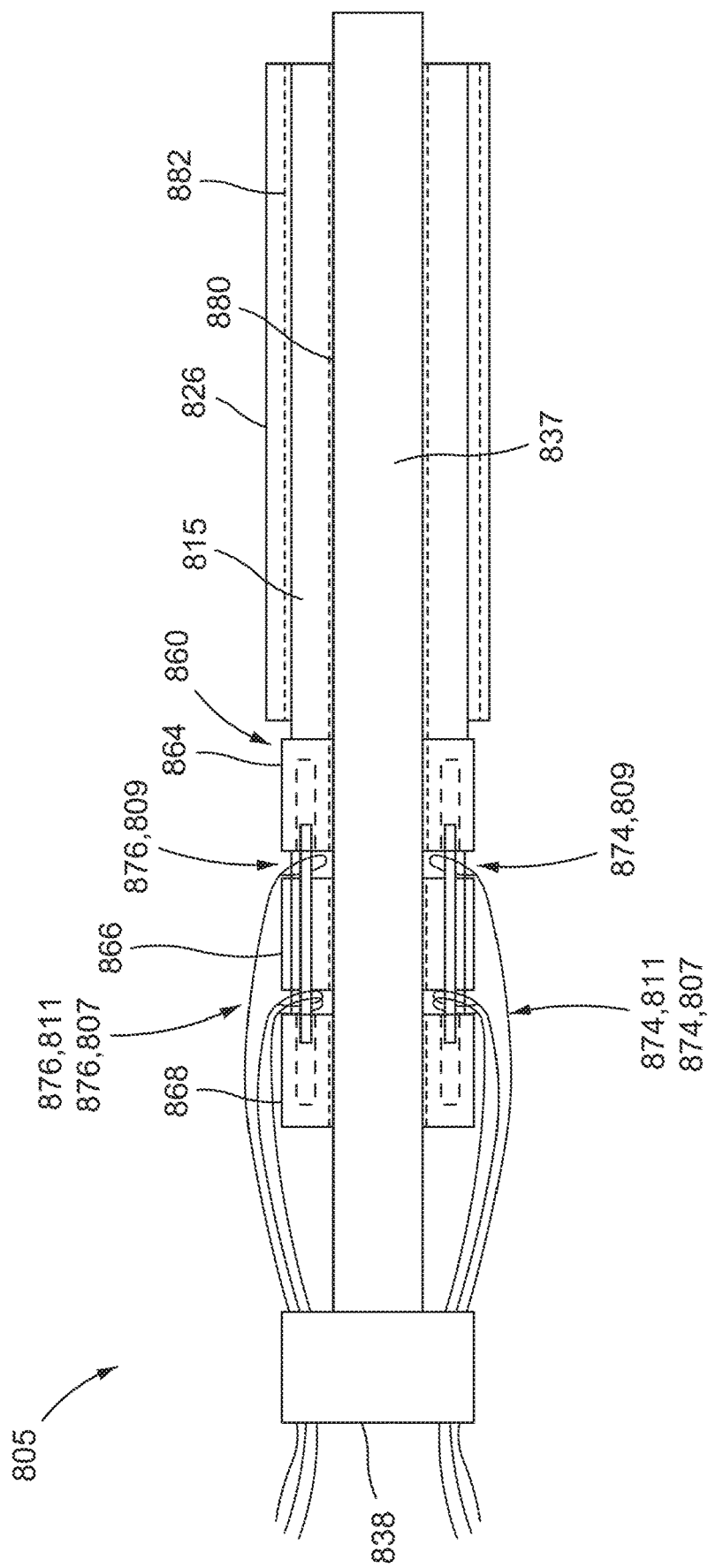
FIG. 36D is a schematic illustration of a side view of the delivery system and actuation wires of FIG. 36A, shown in a third configuration.
Figure 37:
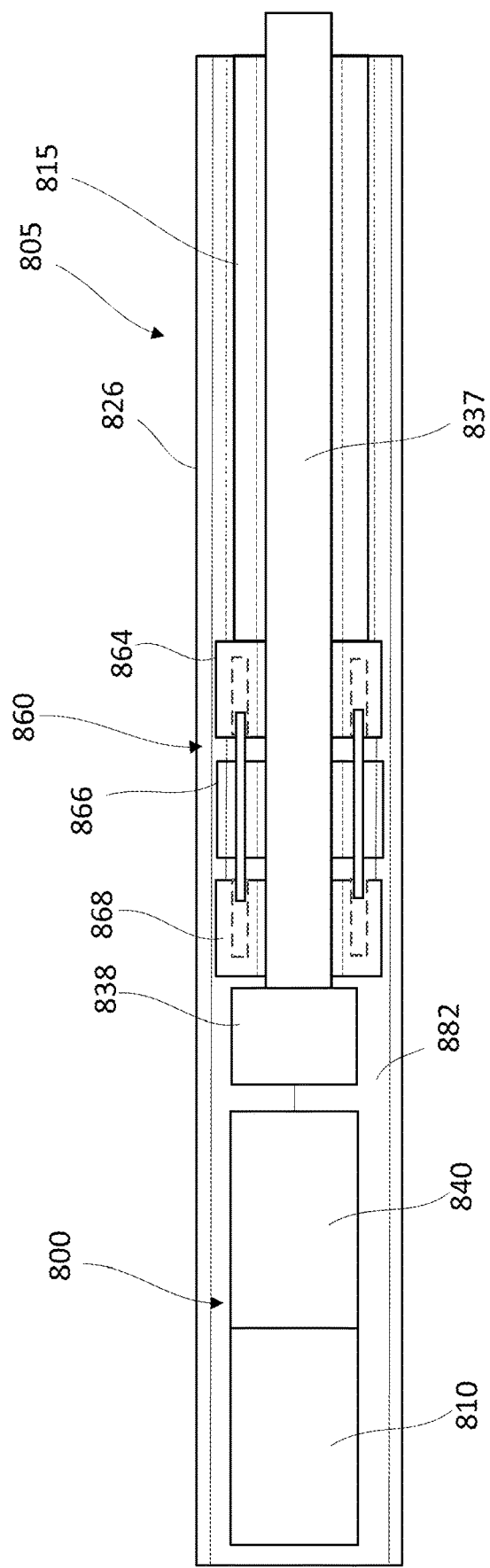
FIG. 37 is a schematic illustration of a side view of the delivery system of FIG. 36A showing a prosthetic valve disposed within a lumen of the delivery sheath.
Figure 38:
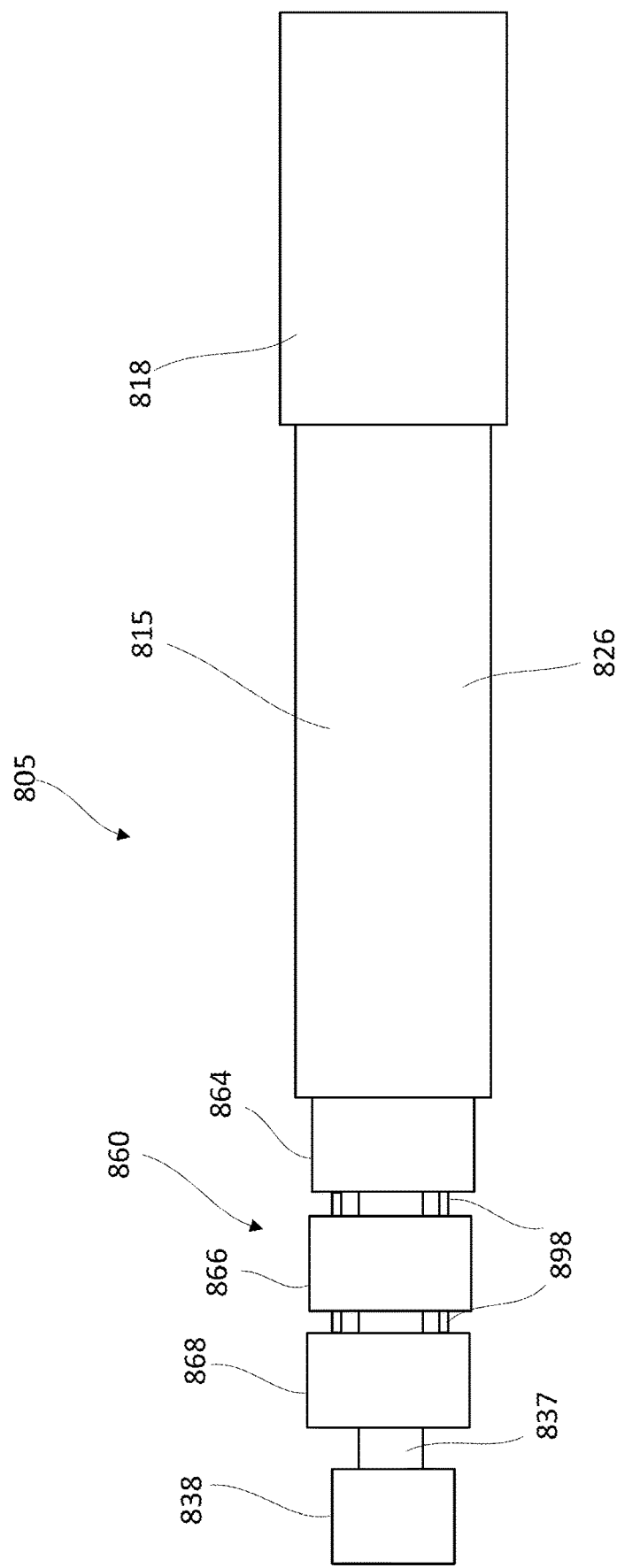
FIG. 38 is a schematic illustration of a side view of the delivery system of FIGS. 36A-37.

In operation, the loops 809 of the actuation wires 874-876 are placed over the pins 878 (as shown in FIG. 36B). The retention device 860 is actuated to move the center retention member 866 proximally such that the pins 878 are received in the apertures 863 of the proximal retention member 864, pinning the loops 809 (i.e., middle loop) of actuation wires 874-876 by pins 878 (as shown in FIG. 36C). The loops 807, 811 of the actuation wires 874-876 are placed over the pins 888 (as shown in FIG. 36B) and the distal retention member 868 is actuated to move the distal retention member 868 proximally toward the center retention member 866 such that the pins 888 are received in the apertures 861 of the distal retention member 868, pinning the loops 807, 811 (i.e., end loops) of the actuation wires 874-876 by pins 888 (as shown in FIG. 36D). The actuation of the distal retention member 868 can be done either sequentially or simultaneously with the actuation of the center retention member 866. In other embodiments, the movement of the various retention members can be varied. For example, in some embodiments, the distal retention member 868 can be fixedly attached to the tube member 815 and the proximal retention member 864 can be moved relative to the center retention member 866. Further, the order of placing the loops on the pins can be varied and the order of actuating the distal retention member 868 and the center retention member 866 can be varied.

With the actuation wires 874-876 pinned to the tube member 815, during deployment of the prosthetic valve 800 within a heart, a user (e.g., physician) can use the tube member 815 to control and/or manipulate movement of the valve (to which the actuation wires are coupled) as described in more detail below. The procedure to deliver the valve to the heart can be the same as or similar to any of the procedures described herein, in the '572 PCT application or in the '305 PCT application incorporated by reference above. For example, a valve, disposed within the delivery system 805 in an inverted configuration, can be delivered to the left atrium of the heart in the same or similar manner as described with reference to FIGS. 43-48 in the '305 PCT application.

With the distal end portion of the delivery sheath 826 disposed within the left atrium of the heart, the valve 800 can be deployed outside of the delivery sheath 826. For example, the valve holder 838 and tube member 815 can be moved distally relative to the outer sheath 826, moving or pushing the valve 800 outside the lumen 882 of the outer sheath 826. In addition, or alternatively, the outer sheath 826 can be moved or pulled proximally, leaving at least a portion of the valve 800 disposed within the heart. In some cases, a tether coupled to the valve 800 can be used to help pull the valve out of the lumen 882 of the outer sheath 826.

As described above for previous embodiments, as the outer frame of the valve becomes unconstrained by the outer sheath 826, the outer frame can begin to revert to its expanded or uninverted configuration. The actuation wires 874-876 can be used to control the reversion of the outer frame. More specifically, the tube member 815 can be pulled proximally such that the actuation wires (pinned to the tube member 815) pull the distally disposed portion of the outer frame proximally in a controlled manner and such that the reversion of the outer frame from its inverted configuration relative to the inner frame of the valve can be controlled.

In addition, as described above for previous embodiments, in some instances, the actuation wires 874-876 can assist in the articulation and placement of the valve into its destination (e.g., a native annulus of an atrioventricular valve of a heart). For example, the actuation wires 874-876 can also be used to constrain, collapse, or otherwise move the valve (e.g., radially compress the outer frame of the valve) after the valve exits the outer sheath 826 and is in its reverted, expanded or partially expanded configuration. More specifically, in this embodiment, the tube member 815 with the actuation wires 874-876 pinned thereto, can be manipulated by a user to move or urge the outer frame to a more compressed configuration by pulling or moving the tube member 815 proximally. This may be desirable, for example, to reposition the valve within the heart before fully deploying the valve. An example repositioning procedure is shown in FIGS. 49A-49D and described below.

When the outer frame of the valve is disposed in its non-inverted and at least partially expanded configuration, and is in a desired position within the heart, the inner frame can be deployed. As described above for valve 400, in some embodiments, to decouple the inner frame from the valve holder 838, the valve holder 838 can be moved distally and/or an inner sheath (not shown) can be moved proximally such that the valve holder 838 is disposed outside of the lumen of the inner sheath. As such, the couplers (e.g., 406, 506) can be released from the recesses (404, 504) releasing or decoupling the inner frame from the valve holder 838. In some embodiments in which the valve holder 838 includes an inner member that holds the couplers within the valve holder 838, the inner member can be moved distally to release the couplers from the valve holder 838. When the inner frame is released from the valve holder 838 and disposed outside the delivery sheath 826, the inner frame can assume its biased expanded configuration.

The actuation wires 874-876 can also be released or decoupled from the outer frame before or after the inner frame is released from the valve holder 838. In this embodiment, to decouple the actuation wires 874-876 from the outer frame, the end loops 807, 811 of the actuation wires 874-876 can be unpinned or decoupled from the tubular member 815 by actuating the distal retention member 868 to release the loops 807, 811 from the pins 888. The center loops 809 of the actuation wires 874-876 remain pinned by the pins 878 and thus the actuation wires 874-876 remain coupled to the tube member 815. With the center loop 809 of each of the actuation wires 874-876 coupled to the tube member 815 (via pinning members 878 in this example), the tube member 815 can be pulled proximally, which in turn will pull the ends of the actuation wires 874-876 out of the loops of outer frame of the valve. Thus with the actuation wires 874-876 detached from the outer frame, the outer frame can assume a biased expanded or partially expanded configuration.

As described above for previous embodiments, the actuation wires 874-876 can be decoupled from the outer frame at any suitable sequence or time period within the procedure. For example, in some instances it may be desirable for the actuation wires 874-876 to be released after the valve has at least partially exited the delivery sheath 826 but before the valve is seated within the native annulus of the atrioventricular valve. In other instances, for example, the actuation wires 874-876 can be released after the valve has at least partially exited the outer delivery sheath 826 and after the valve is seated within the native annulus of the atrioventricular valve.

Figure 39:
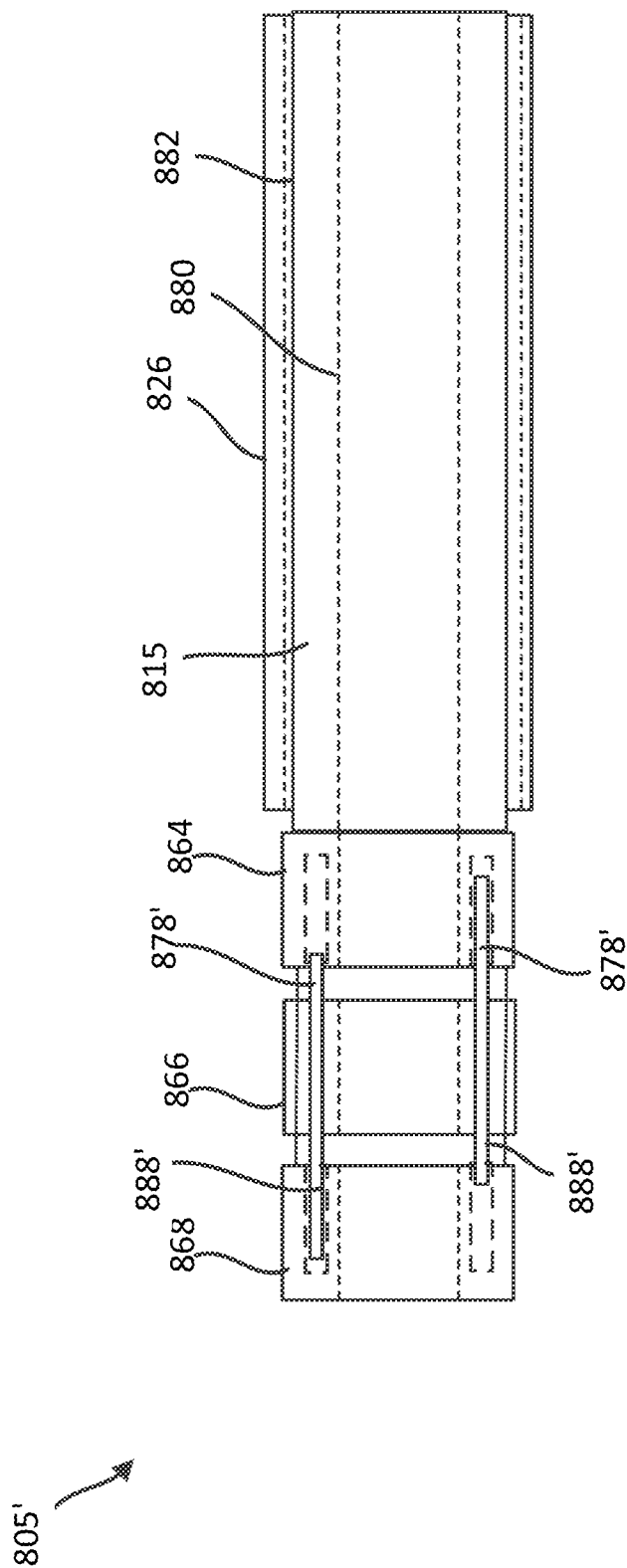
FIG. 39 is a schematic illustration of a side view of a delivery system according to another embodiment, with a different pin configuration than the delivery system of FIGS. 36A-38.
Figure 60:
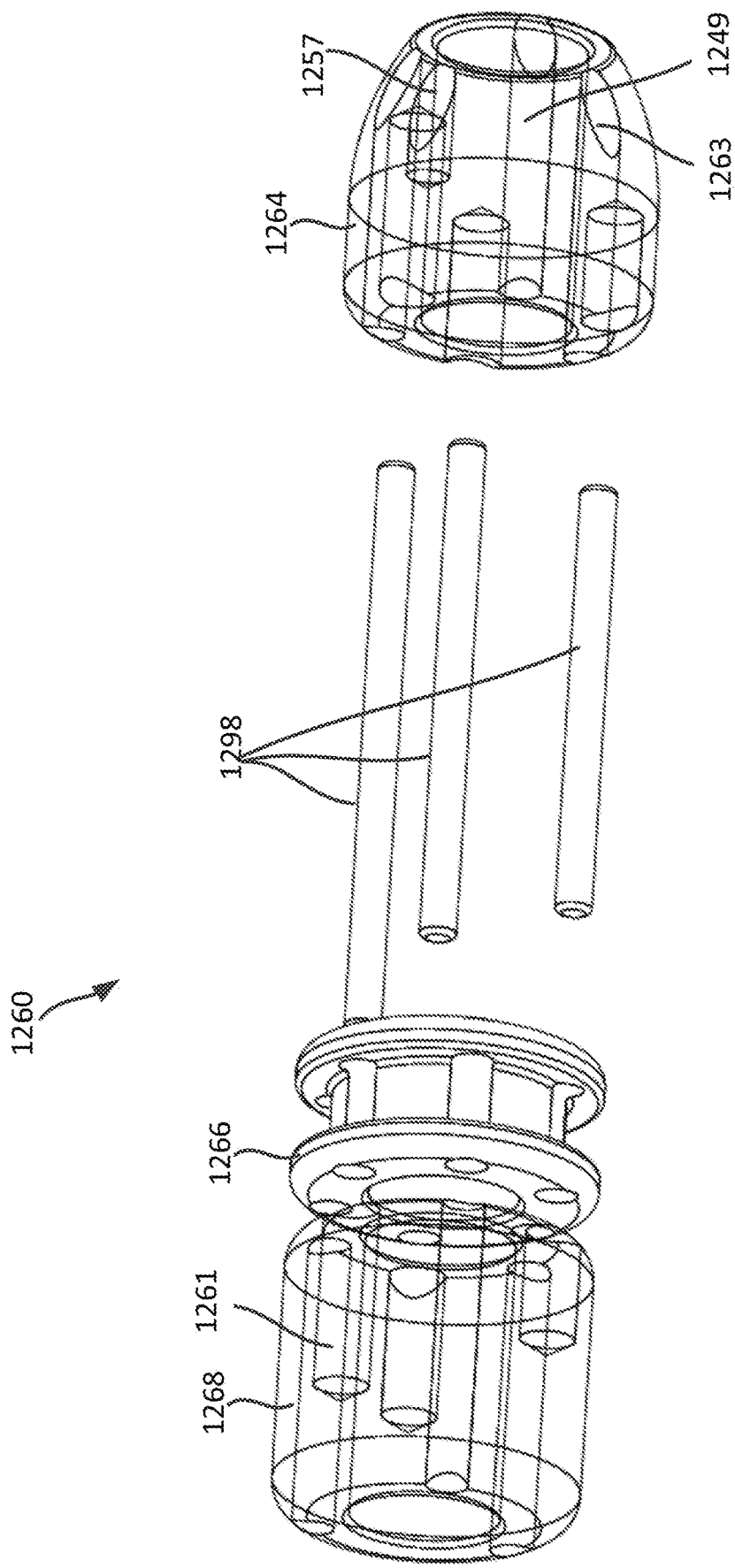
FIG. 60 is an exploded perspective view of the retention device of FIG. 59, shown partially transparent.
Figure 61:
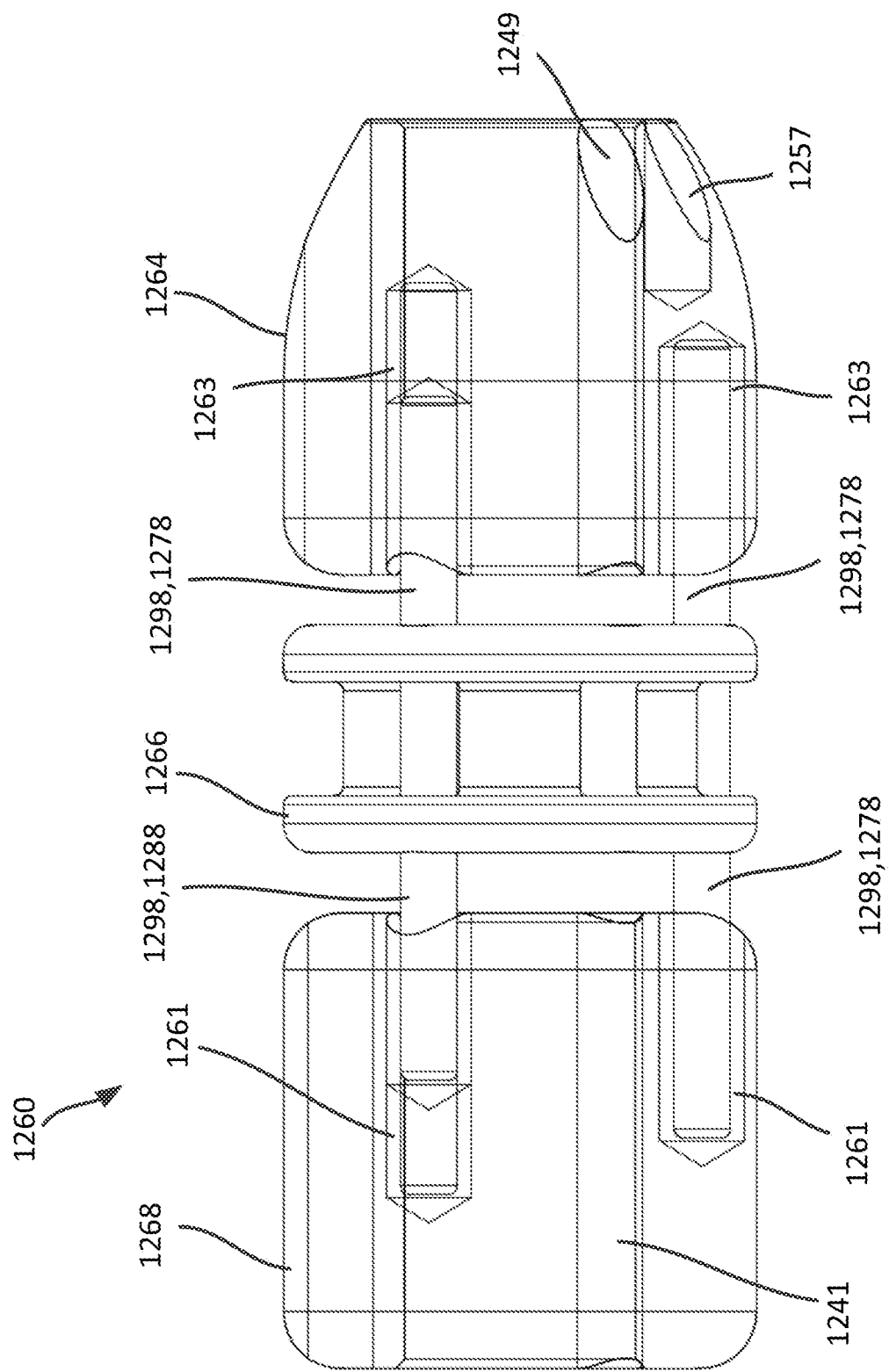
FIG. 61 is a side view of the retention device of FIG. 59.
Figure 64B:
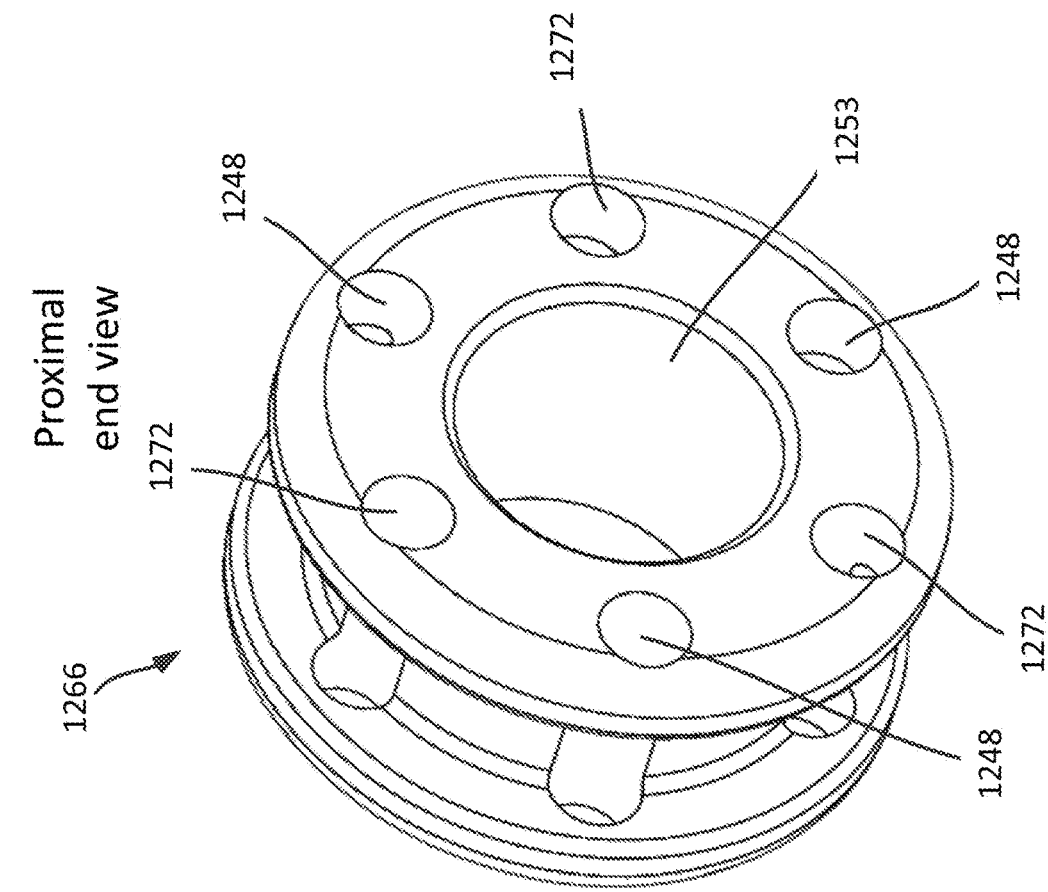
FIG. 64A is a perspective distal end view and FIG. 64B is a perspective proximal end view of a center retention member of the retention device of FIG. 59.
Figure 64A:
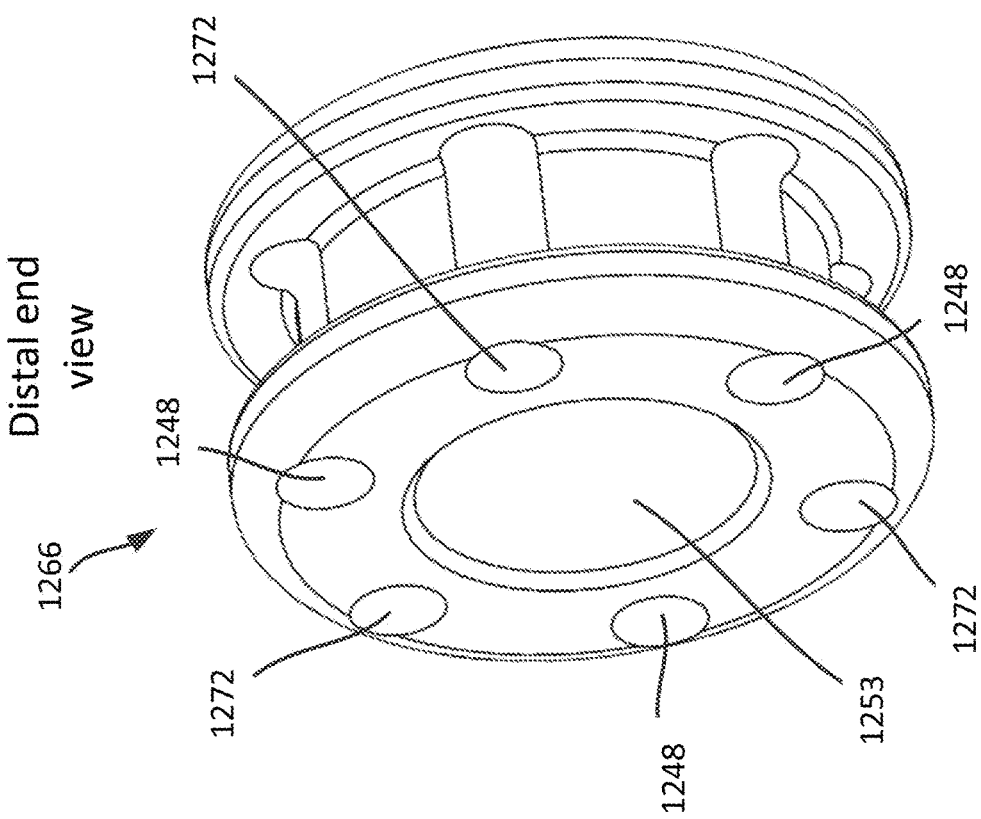

In some embodiments, the pins 898 of the retention device 860 can have different lengths resulting in different lengths for the pin portions 878 and 888 (see, e.g., pins 1298 in FIG. 60). In some embodiments, the pins 898 may have the same length but are disposed such that the pin portions 878 and 888 have different lengths. For example, as shown in FIG. 39, the delivery device 805' is shown with pin portions 878' having different lengths and pin portions 888' having different lengths. In other words, the pins 878' extending on the proximal side of the center retention member 866 each have different lengths, and the pins 888' extending on the distal side of the center retention member 866 each have a different length. In such an embodiment, additional control over the release of the actuation wires can be achieved. For example, as shown in FIG. 39, a slight amount of movement of the distal retention member 866 could release the loop of an actuation wire retained by the shorter pin 888', while the loop pinned by the longer pin 888' would remain pinned. Similarly, a slight movement of the center retention member 866 could release the loop pinned by the shorter pin 878', while the loop pinned by the longer pin 878' would remain pinned.

FIGS. 42-48 illustrate another embodiment of a delivery system 905 (also referred to as a "delivery device") that can be used to deliver and deploy a prosthetic heart valve 900 (see FIGS. 46-48) within a heart in a procedure similar to or the same as the procedures described with respect to other embodiments described herein and embodiments described in the '305 PCT application. Thus, some details regarding the valve and procedures performed therewith are not described herein. It should be understood that for features and functions not specifically discussed, those features and functions can be the same as or similar to the valves described herein (e.g., the valve 200, 500) and/or in the '305 PCT application. The valve 900 can be constructed the same as or similar to, and function the same as or similar to any of the valves described herein (e.g., valves 100, 200, 400, 500) and/or in the '305 PCT application. For example, the valve 900 includes an outer frame assembly 910 that has an outer frame 920, an inner valve assembly 940 that has an inner frame 950, and a tether (not shown) coupled to the inner valve assembly 940.

The delivery system 905 can include the same or similar components as delivery systems 505 or 805 described above. The delivery system 905 includes an outer delivery sheath 926, a valve holder 938 (also referred to as a "pusher"), and an elongate tube member 915 (also referred to as "tube" or "tube member") which can be slidably disposed within a lumen 982 of the delivery sheath 926 and can be coupled to retention components that can be used to secure and release actuation wires 974, 975 and 976 in the same or similar manner as described above for delivery system 805. The valve holder 938 can be coupled to an elongate member 937 (see, e.g., FIG. 47) that can be movably disposed within a lumen (not shown) defined by the elongate tube member 915 and a lumen defined by a retention device 960 described below.

As with other embodiments described herein and embodiments of the '305 PCT application, the delivery system 905 can be used to deliver a valve that can be moved from a biased expanded configuration to an inverted configuration for delivery of the valve to the heart. To deploy the valve within a heart, the outer frame 920 of the valve 900 can be moved to an inverted configuration (as shown in FIG. 46) relative to the inner frame 950 as described above for previous embodiments and placed within a distal end portion of the lumen 982 of the delivery sheath 926.

The inner frame 950 of the valve 900 can be releasably coupled to the valve holder 938 via couplers (not shown) that are received within corresponding recesses (not shown) defined by the valve holder 938 in the same or similar manner as described above for delivery system 405 (see, e.g., FIGS. 26A-26C). In this manner, the valve holder 938 can be used to hold the valve 900 to aid in the control and manipulation of the valve 900 as it is delivered and deployed. In this embodiment, the valve holder 938 includes an inner member (not shown) that is movably disposed within an interior of the valve holder 938. The inner member can be moved to the interior of the valve holder 938 to retain the couplers within the recesses of the valve holder 938. To release the valve 900 from the valve holder 938, the inner member is moved distally to release the couplers from the recesses and in turn, release the valve 900 from the valve holder 938.

As with the previous embodiment, the elongate tube member 915 is coupled to a retention device 960 that includes retention components or members that are coupled together coaxially and can be actuated to secure and release actuation wires coupled to the delivery system 905. The retention device 960 includes a first or proximal retention member 964 fixedly coupled to a distal end portion of the tube member 915, a second or center retention member 966 movably coupled to the proximal retention member 964 and a third or distal retention member 968 movably coupled to the center retention member 966. The center retention member 966 can be coupled to the proximal retention member 964 via an actuation rod 965 (FIGS. 42-43), and the distal retention member 968 can be coupled to the center retention member 966 and to the proximal retention member 964 via a second actuation rod (not shown). The actuation rods can extend to a proximal end of the delivery device 905 and be operably coupled to a handle assembly (not shown). Multiple pins 998 are fixedly attached to the center retention member 966 that include multiple proximal pins 978 (see e.g., FIGS. 42-43) that extend proximally and multiple distal pins 988 (see e.g., FIG. 44) that extend distally. The pins 978 and 988 can be used to releasably hold actuation wires 974, 975 and 976 to the delivery device 905 in the same or similar manner as described above delivery system 905. For example, the pins 978 can be received within apertures/lumens (not shown) defined by the proximal retention member 964 and the pins 988 can be received within apertures/lumens (not shown) defined by the distal retention member 968.

As with previous embodiments, multiple actuation wires can be coupled to the outer frame assembly 910 of the prosthetic valve 900 and used to help revert and manipulate the prosthetic valve 900 into a desired position within the heart, and then can be released from the valve when the desired positioning has been achieved. More specifically, the outer frame 920 of the valve 900 includes loops 962 (see FIG. 48) at a free end portion of the outer frame 920 through which the actuation wires 974-976 can be threaded or received therethrough in the same or similar manner as described herein (e.g., with respect to valve 500) and/or in the '305 PCT application. In this embodiment, the outer frame 920 also includes a second row of loops 958 through which the actuation wires can also be threaded. Having two rows of loops on the outer frame 920 to receive the actuation wires can help assist with the flipping or reverting of the outer frame 920 during delivery. The two rows of loops on the outer frame 920 can also help reduce tension on the cuff or free end portion of the outer frame when the actuation wires are pulled during the reverting.

Figure 69B:
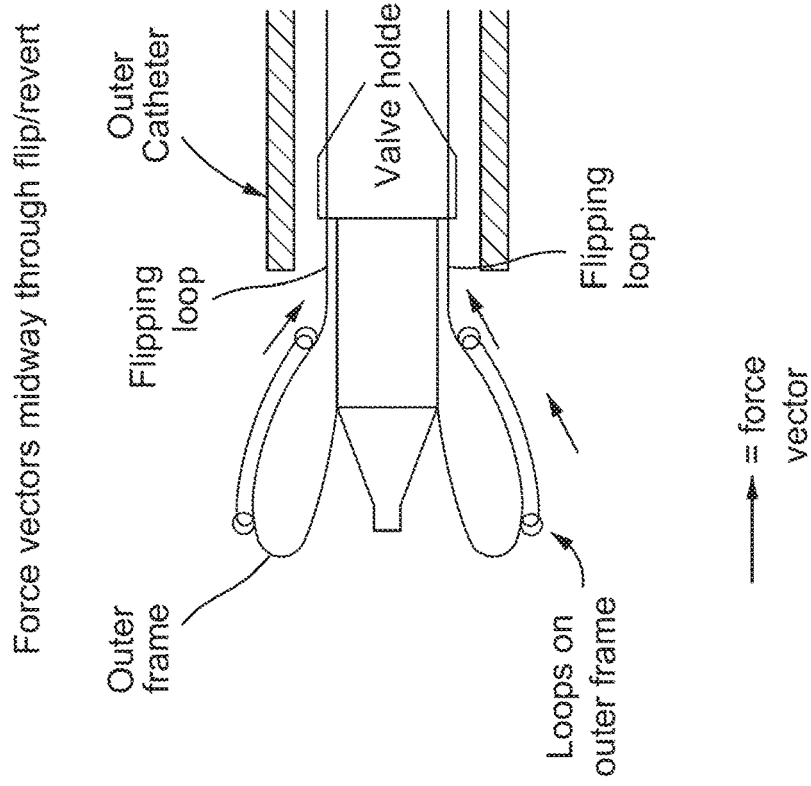
FIGS. 69A and 69B illustrate force vectors associated with reverting a prosthetic valve.
Figure 69A:
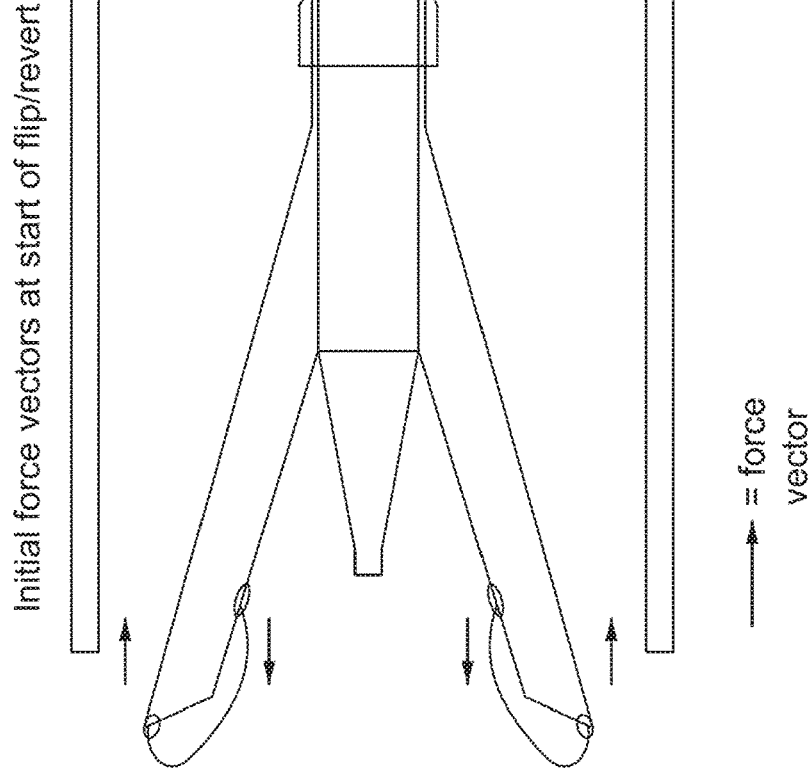

FIGS. 69A and 69B illustrate force vectors associated with forces applied to the outer frame 920 when being pulled by the actuation wires to revert/flip the outer frame 920 during delivery of the prosthetic valve. FIG. 69A illustrates the force vectors associated with the outer frame when the outer frame is initially being reverted/flipped. As shown in FIG. 69A, the force vectors associated with the loops (e.g., 962) at the outer tip or cuff of the outer frame are opposite of the force vectors associated with the loops (e.g., 958) at the middle portion of the outer frame where the actuation wire are coupled to the outer frame. This causes a hinge effect to the cuff of the outer frame when being pulled and helps revert the outer frame from its inverted configuration relative to the inner frame of the valve. As the outer frame is further reverted, the force vectors associated with the loops (e.g., 962) at the outer tips and the force vectors associated with the loops (e.g., 958) at the middle portion of the outer frame are in the same direction as shown in FIG. 69B. At this point of the reversion, the outer frame has been reverted past the loops at the middle portion and as the actuation wires are pulled further proximally, having all forces pulling in the same direction (proximally) can help to fully revert the outer frame.

In addition, when the outer frame is being reverted by pulling the actuation wires proximally, the routing of the actuation wires through two rows of loops on the outer frame helps reduce the profile of the outer frame during the reverting/flipping. When the outer frame has been reverted and the inner frame is released from the valve holder, and when tension is applied to the actuation wires they can function as purse strings at both the cuff tips of the outer frame and the middle portion of the outer frame to pull in or reduce the outer profile of the outer frame and the valve overall. The reduced profile helps during the positioning of the valve within an annulus (e.g., mitral valve annulus) of the heart.

Figure 47:
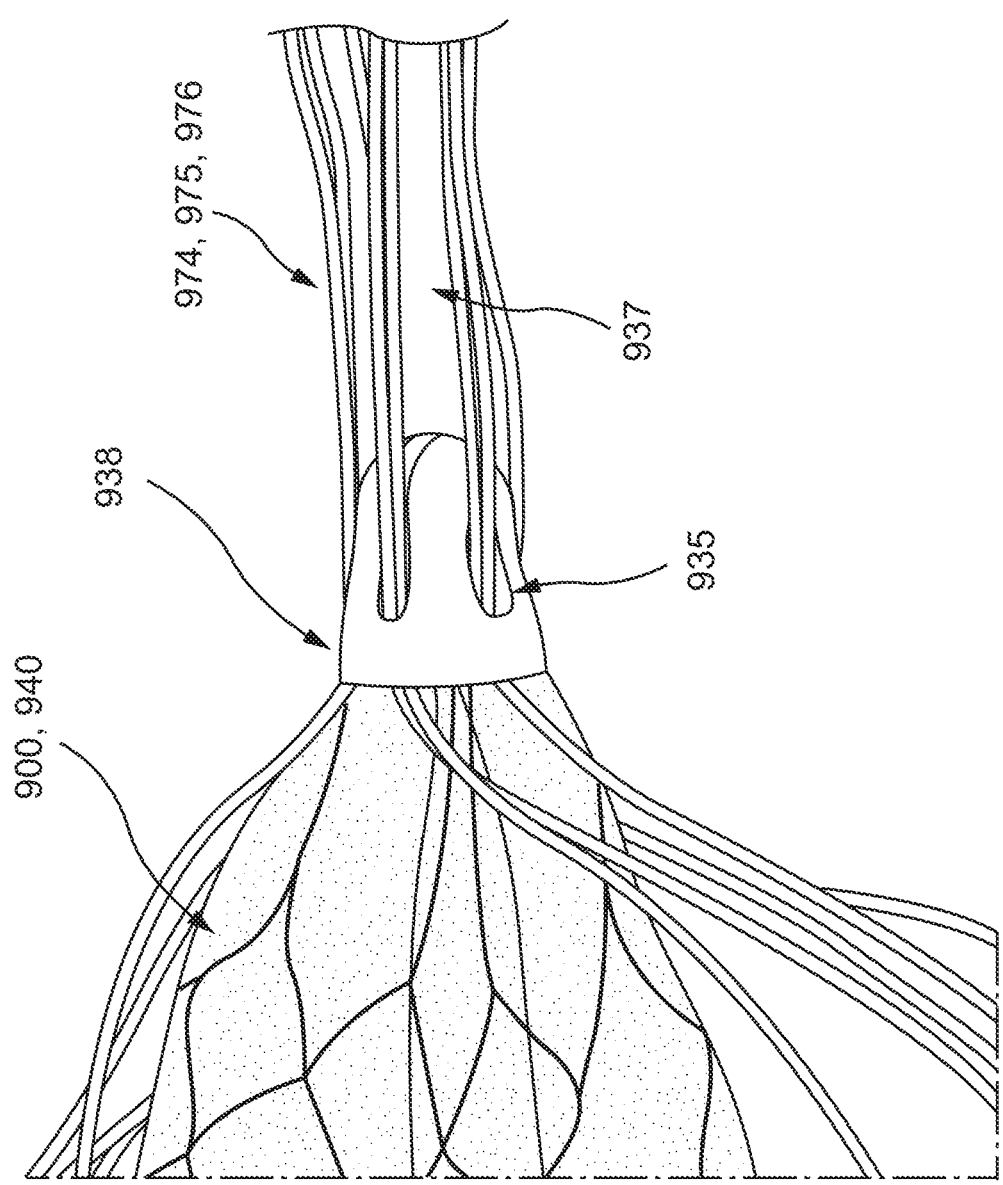
FIG. 47 is an enlarged view of a portion of the delivery system of FIG. 46.

The actuation wires 974, 975, 976 are also routed through apertures 935 (see FIG. 47) defined by the valve holder 938 as shown in FIGS. 46 and 47. This helps maintain the actuation wires 974-976 close to the valve holder 938 and within the lumen of the delivery sheath 926 during delivery.

Figure 50:
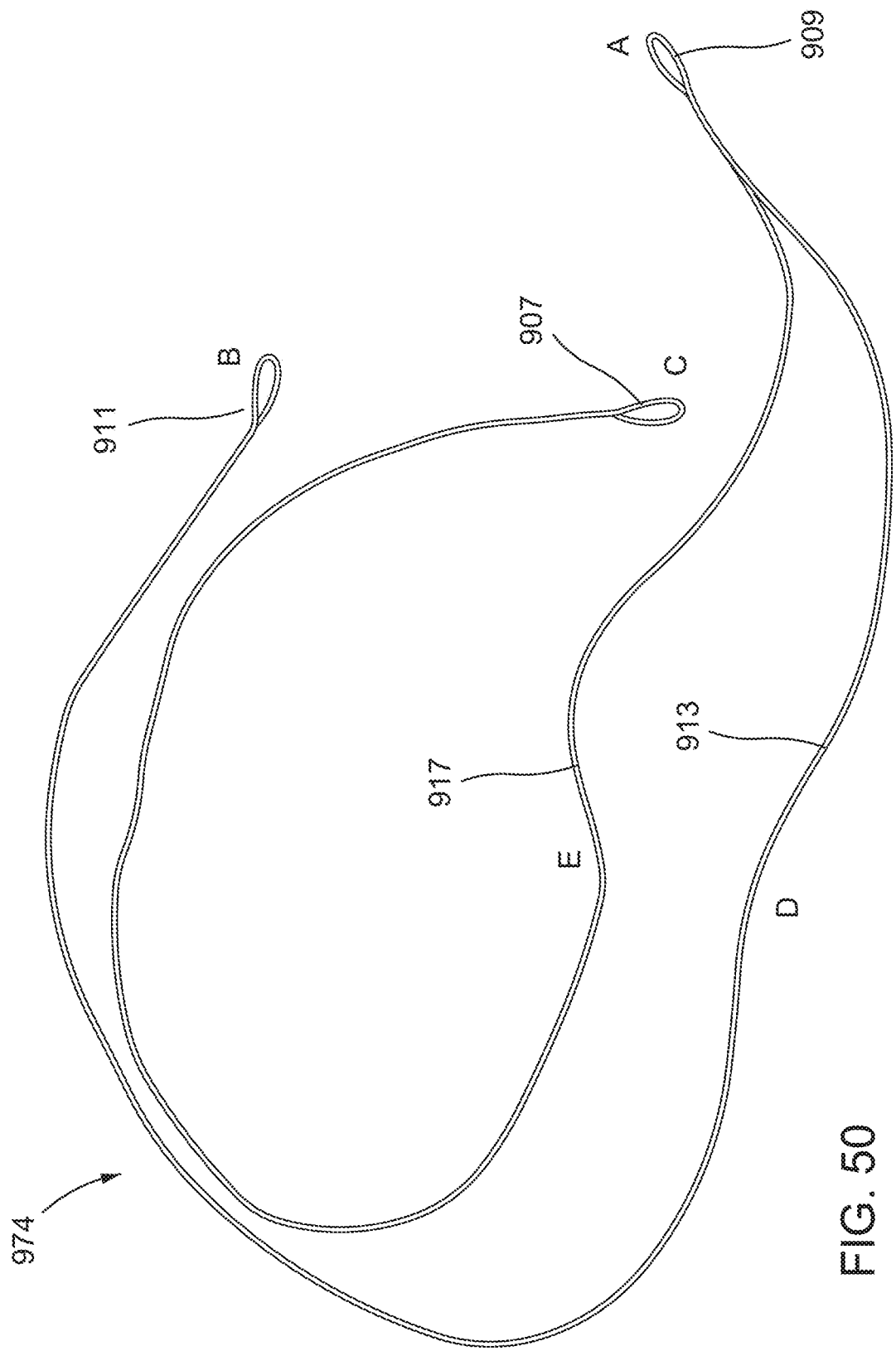
FIG. 50 is a top view of an actuation wire according to another embodiment.
Figure 51:
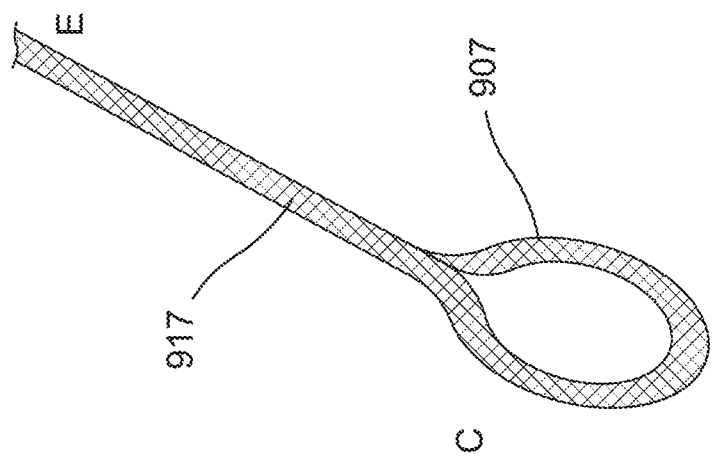
FIG. 51 is a perspective view of a portion of the actuation wire of FIG. 50.
Figure 52:
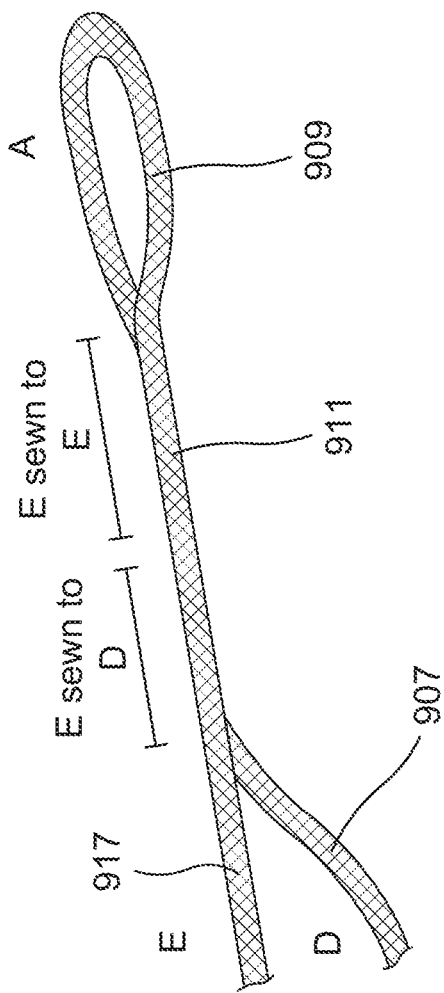
FIG. 52 is a perspective view of a portion of the actuation wire of FIG. 50.

FIGS. 50-52 illustrate an embodiment of an actuation wire 974 that can be used with delivery device 905. Further details regarding the construction of the actuation wires 974 are described below with respect to FIGS. 50-52. Other configurations of an actuation wire can alternatively be used as described above. The actuation wire 974 can be the same as or similar to the actuation wire 874 and includes a center loop 909 and two end loops 907 and 911 and two strands 913 and 917. Actuation wires 975 and 976 can be constructed the same as actuation wire 974 or have a different construction. As shown, for example, in FIGS. 43-45, the actuation wires 974-976 can be pinned to the retention device 960 in the same manner as described above for delivery system 805, and therefore, some details are not described with respect to this embodiment. More specifically, the end loops 907 and 911 can be pinned by pins 988 between the center retention member 966 and the distal retention member 968 and the center loops 909 can be pinned by pins 978 between the center retention member 966 and the proximal retention member 964. As described above, the outer frame 920 has two rows of loops 962 and 958. As shown in FIG. 48, in this embodiment, each actuation wire 974, 975, 976 is routed through four outer loops 962 and four loops 958 of the outer frame 920. For example, the center loop 909 of actuation wire 974 is pinned to the proximal retention member 964 and strands 913 and 917 of actuation wire 974 are each routed through two outer loops 962 and two loops 958 of the outer frame 920. Actuation wires 975 and 976 are similarly routed.

Figure 43:
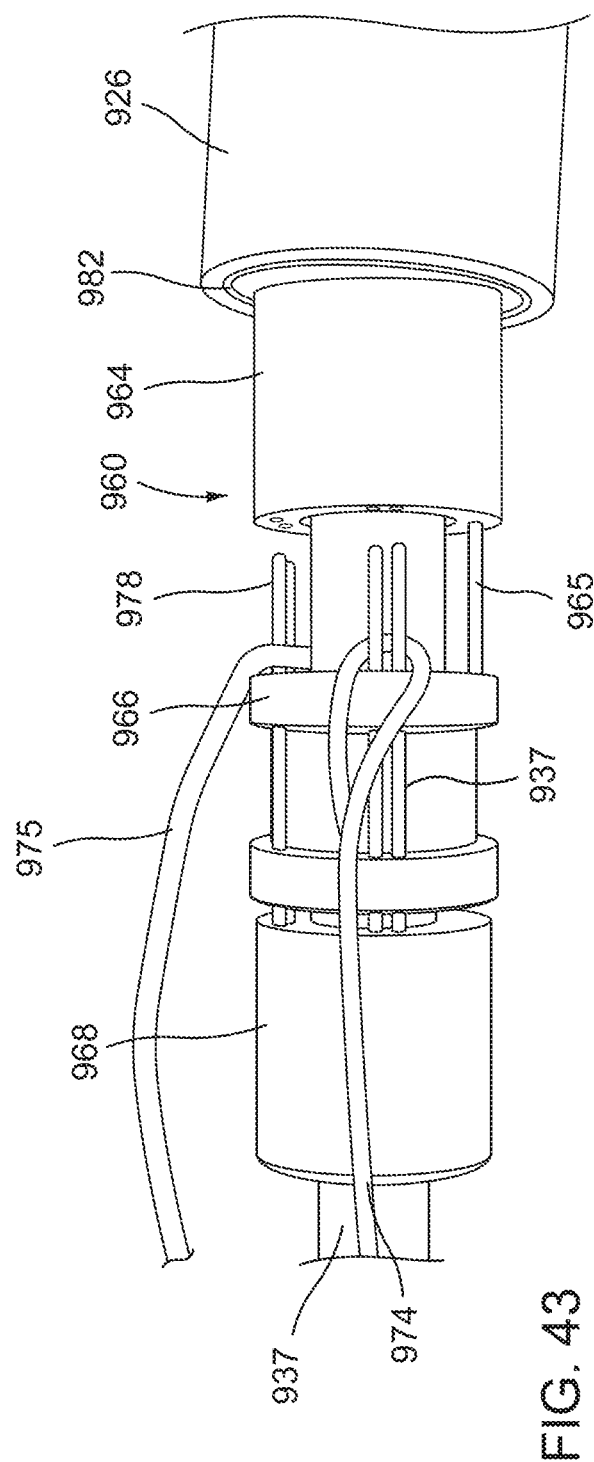
FIG. 43 is a side view of a portion of the delivery system of FIG. 42 shown in the first configuration and with actuation wires coupled thereto.

In operation, the loops 909 of the actuation wires 974-876 are placed over the pins 978 (as shown in FIG. 43) and the retention device 960 is actuated to move the center retention member 966 proximally such that the pins 978 are received in the apertures of the proximal retention member 964, pinning the loops 909 (i.e., middle loop) of actuation wires 974-976 by pins 978 (as shown in FIG. 44). The loops 907, 911 of the actuation wires 974-976 are placed over the pins 988 and the distal retention member 968 is actuated to move the distal retention member 968 proximally toward the center retention member 966 such that the pins 988 are received in the apertures of the center retention member 966, pinning the loops 907, 911 (i.e., end loops) of the actuation wires 974-976 by pins 988 (as shown in FIG. 45). The actuation of the distal retention member 968 can be done either sequentially or simultaneously with the actuation of the center retention member 966. In other embodiments, the movement of the various retention members can be varied. For example, in some embodiments, the distal retention member 968 can be fixedly attached to the tube member 915 and the proximal retention member 964 can be moved relative to the center retention member 966. Further, the order of placing the loops on the pins can be varied and the order of actuating the distal retention member 968 and the center retention member 964 can be varied.

With the actuation wires 974-976 pinned to the tube member 915, during deployment of the prosthetic valve within a heart, a user (e.g., physician) can use the tube member 915 to control and/or manipulate movement of the valve (to which the actuation wires are coupled) as described in more detail below. The procedure to deliver the valve 900 to the heart can be the same as or similar to any of the procedures described herein, in '572 PCT application or in the '305 PCT application incorporated by reference above. For example, the valve 900, disposed within the delivery system 905 in an inverted configuration, can be delivered to the left atrium of the heart in the same or similar manner as described with reference to FIGS. 43-48 in the '305 PCT application.

With the distal end portion of the delivery sheath 926 disposed within the left atrium of the heart, the valve 900 can be deployed outside of the delivery sheath 926 as shown in FIG. 46. FIG. 46 illustrates the valve 900 still in the inverted configuration, but unconstrained by the delivery sheath 926. As described for previous embodiments, the valve holder 938 and tube member 915 can be moved distally relative to the outer sheath 926, moving or pushing the valve 900 outside the lumen 982 of the outer sheath 926. In addition, or alternatively, the outer sheath 926 can be moved or pulled proximally, leaving at least a portion of the valve 900 disposed within the heart. In some cases, a tether coupled to the valve can be used to help pull the valve out of the lumen 982 of the outer sheath 926.

As described above for previous embodiments, as the outer frame 920 of the valve 900 becomes unconstrained by the outer sheath 926, the outer frame 920 can begin to revert to its expanded or uninverted configuration. The actuation wires 974-976 can be used to control the reversion of the outer frame 920. More specifically, the tube member 915 can be pulled proximally such that the actuation wires (pinned to the tube member 915) pull the distally disposed portion of the outer frame 920 proximally in a controlled manner and such that the reversion of the outer frame 920 from its inverted configuration (FIG. 46) relative to the inner frame 950 of the valve 900 can be controlled. FIG. 48 illustrates the valve 900 when the outer frame 920 has reverted from its inverted delivery configuration and has assumed its biased expanded configuration.

In addition, as described above for previous embodiments, in some instances, the actuation wires 974-976 can assist in the articulation and placement of the valve into its destination (e.g., a native annulus of an atrioventricular valve of a heart). For example, the actuation wires 974-976 can also be used to constrain, collapse, or otherwise move the valve (e.g., radially compress the outer frame of the valve) after the valve exits the outer sheath 926 and is in its reverted, expanded or partially expanded configuration. More specifically, in this embodiment, the tube member 915 with the actuation wires 974-976 pinned thereto, can be manipulated by a user to move or urge the outer frame to a more compressed configuration by pulling or moving the tube member 915 proximally. This may be desirable, for example, to reposition the valve within the heart before fully deploying the valve. Such a repositioning procedure is shown and described with respect to FIGS. 49A-49D.

When the outer frame 920 of the valve 900 is disposed in its non-inverted and at least partially expanded configuration, and is in a desired position within the heart, the inner frame 950 can be deployed. As described above, in some embodiments, to decouple the inner frame 950 from the valve holder 938, the inner member (not shown) of the valve holder 938 can be moved distally to release the couplers (e.g., 406, 506) from the recesses (404, 504) of the valve holder 938, releasing or decoupling the inner frame 950 from the valve holder 938. When the inner frame 950 is released from the valve holder 938 and disposed outside the delivery sheath 926, the inner frame can assume its biased expanded configuration.

The actuation wires 974-976 can be released or decoupled from the outer frame 920 before or after the inner frame 950 is released from the valve holder 938. As with the previous embodiment, to decouple the actuation wires 974-976 from the outer frame 920, the end loops 907, 911 of the actuation wires 974-976 can be unpinned or decoupled from the tubular member 915 by actuating the distal retention member 968 to release the loops 907, 911 from the pins 988. The center loops 909 of the actuation wires 974-976 remain pinned by the pins 978 and thus the actuation wires 974-976 remain coupled to the tube member 915. With the center loop 909 of each of the actuation wires 974-976 coupled to the tube member 915 (via pinning members 978 in this example), the tube member 915 can be pulled proximally, which in turn will pull the ends of the actuation wires 974-976 out of the loops 962, 958 of outer frame 920 of the valve 900. Thus with the actuation wires 974-976 detached from the outer frame 920, the outer frame 920 can assume a biased expanded or partially expanded configuration.

As described above for previous embodiments, the actuation wires 974-976 can be decoupled from the outer frame 920 at any suitable sequence or time period within the procedure. For example, in some instances it may be desirable for the actuation wires 974-976 to be released after the valve 900 has at least partially exited the delivery sheath 926 but before the valve 900 is seated within the native annulus of the atrioventricular valve. In other instances, for example, the actuation wires 974-976 can be released after the valve 900 has at least partially exited the outer delivery sheath 926 and after the valve is seated within the native annulus of the atrioventricular valve.

Figure 49B:
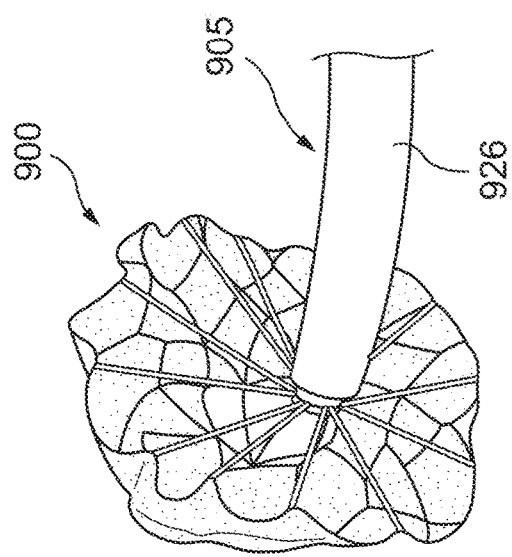
FIGS. 49A-49D illustrates stages in a procedure to reposition a partially deployed prosthetic valve using the delivery device of FIG. 42.
Figure 49D:
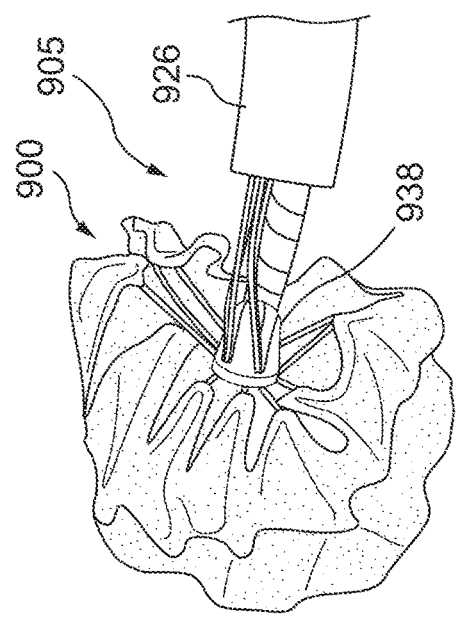
Figure 49A:
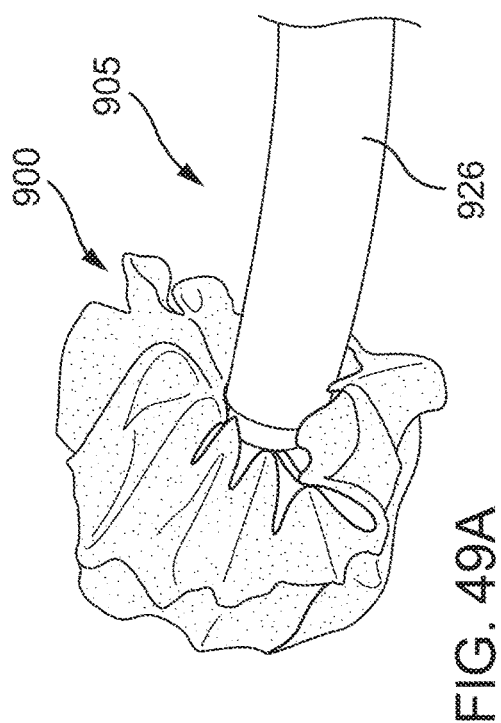
Figure 49C:
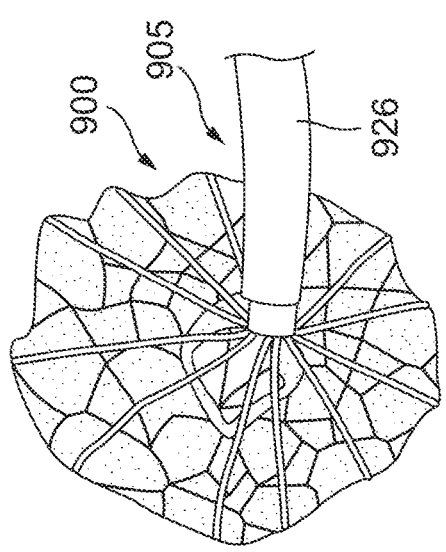

FIGS. 49A-49D illustrate use of the delivery device 905 to position the valve 900 within an annulus of a native mitral valve. The configuration and operation of the retention device 960 and delivery device 905 provides the ability to add tension to the actuation wires 974-976 by moving the retention device 960 proximally within the lumen 982 of the delivery sheath 926 as shown in FIG. 49A. This pulls the cuff tips or outer free end portions of the outer frame assembly 910 toward the valve holder 920 and reduces the overall profile of the valve 900. When the actuation wires are formed of, for example a fiber (e.g., a suture material), the valve 900 is able to hinge freely at the valve holder 938, allowing the valve 900 to turn into the mitral annulus under a minimal turn radius. When within the mitral annulus, the tension on the actuation wires can be released as shown in FIGS. 49B and 49C. If the valve 900 is positioned in an undesirable position within the annulus, either axially or radially, tension on the actuation wires can be reapplied as shown in FIG. 49D. In this position (as shown in FIG. 49D), the valve 900 can be axially or radially repositioned by moving the valve holder 938 forward or backward, or by rotating/turning the valve holder 938. Because the actuation wires are nested or coupled within the valve holder 938, the motion of the valve holder 938 is transferred to the valve 900. When the valve 900 is repositioned in a desired position within the annulus, the actuation wires can be released from the valve 900 as described above by actuating the retention device 960 to release the end loops of the actuation wires (maintaining the center loops coupled to the retention device 960). The valve holder 938 and tube member 915 can then be moved proximally to pull the end loops out of the loops of the outer frame 920. In some embodiments, the valve holder 938 can be maintained in its position, while the tube member 915 is pulled proximally to pull the end loops of the actuation wires out of the outer frame 920. For example, when the valve is positioned in the annulus, after releasing the end loops from the retention device 960, the valve holder 938 can help maintain the valve in a desired position with the annulus. This may be desirable for example, to prevent or limit the cuff of the outer frame assembly 910 from pulling in as the end loops are being pulled through the loops 962 and 958 on the outer frame 920.

The configurations of the actuation wires described herein and used with the delivery devices to deploy a prosthetic valve are constructed such that the loops can be easily released from the delivery system when needed, and can smoothly route through the valve to disengage after deployment of the valve. The loops of the actuation wires can be constructed by various processes including a bifurcation process, a sewing process or both. The actuation wires can be formed with, for example a fiber material or a braided material, such as used with sutures. The delivery devices described herein can also be used with actuation wires formed and constructed by different methods and have various configurations, such as, for example, the actuation wires described above with reference to FIGS. 31A-31D.

FIGS. 50-52 illustrate an actuation wire 974 that can be used with the delivery devices described herein. The actuation wire 974 can be configured the same as actuator wire 874 and includes a center loop 909 (also labeled A) and two end loops 907 (also labeled C) and 911 (also labeled B). The center loop 909 is connected to the end loop 907 by a strand 917 (also labeled E) and the center loop 909 is connected to the end loop 911 by a strand 913 (also labeled D).

FIGS. 51-52 illustrate a braiding and sewing process to form the loops 909, 907, 911. For ease of discussion, reference will be made to reference labels A-E. Actuation wire 974 is formed with two sub-sections: a first section that includes loop B and strand D and a second section that includes loop C and strand E. FIG. 51 is an enlarged view of loop C. Loop C can be formed by braiding half the files (i.e., filers or filaments) of the material that forms strand E and loop C around a mandrel, and then recombining the files and braiding them together to form loop C. For example, if strand E is a 16 file braid, then loop C will be formed of an 8 file braid. Thus, there is no increase in the profile or thickness when transitioning from strand E to loop C. There are also no raised portions or steps between C and E and no sewing to form loop C. Such a construction leads to ease of removal of the actuation wire 974 when being removed/withdrawn from the prosthetic valve. To form loop A (the center loop), the non-looped end of the first section (C and E) is doubled back on itself and sewn to itself to form loop A as shown in FIG. 52. Also as shown in FIG. 52, strand E can also be sewn to strand D of the second section (strand D and loop B). Loop B can be formed in the same manner as loop C.

Figure 53:
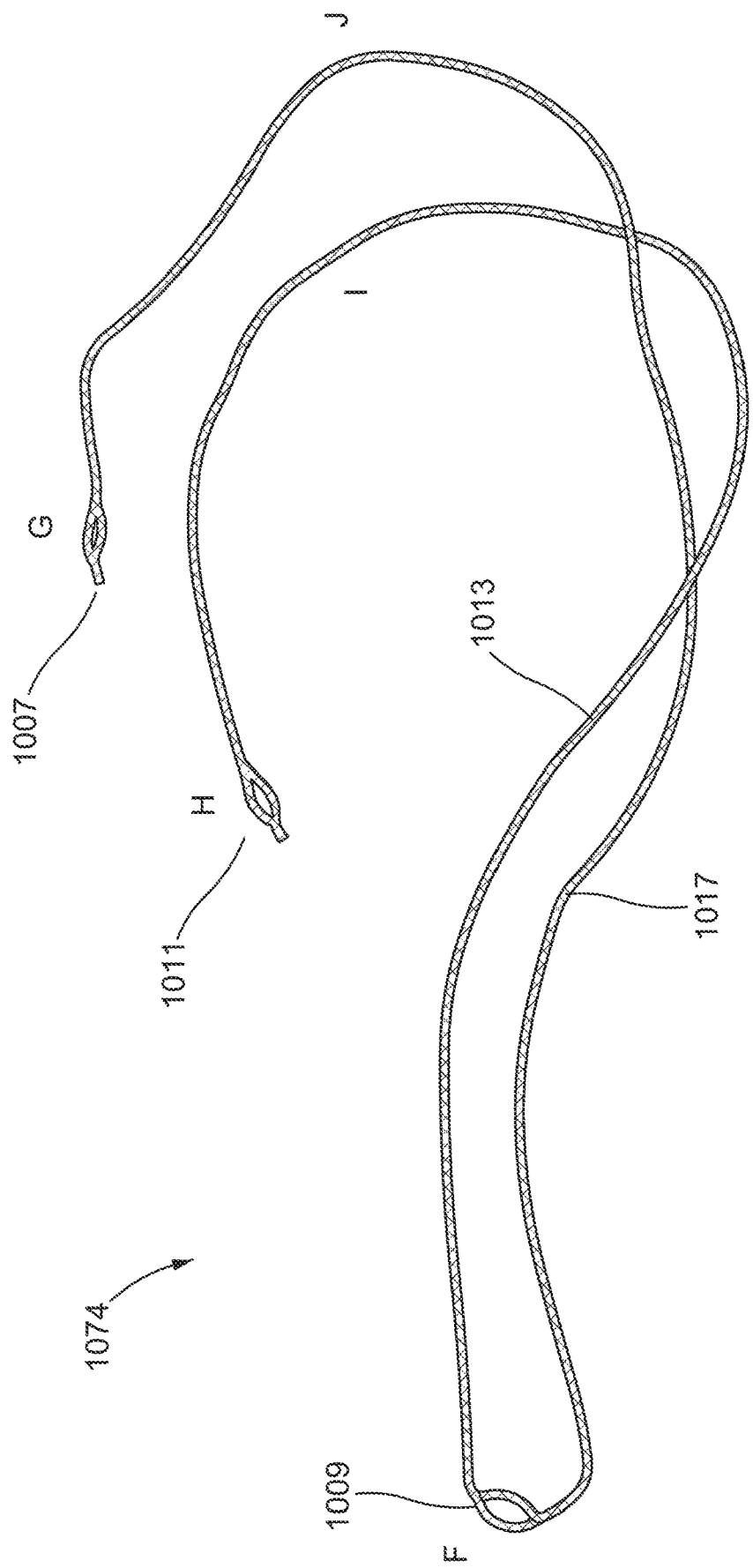
FIG. 53 is a perspective view of an actuation wire according to another embodiment.
Figure 54:
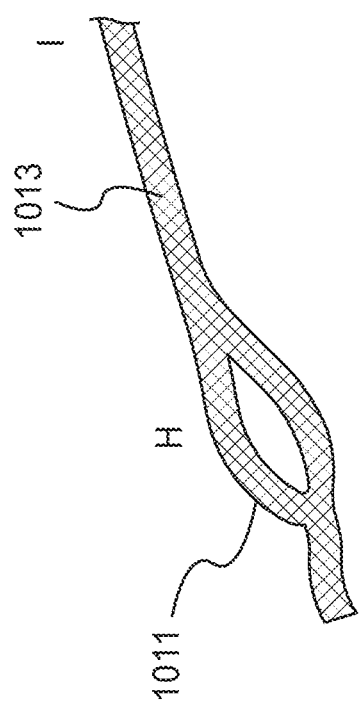
FIG. 54 is a perspective view of a portion of the actuation wire of FIG. 53.
Figure 55:
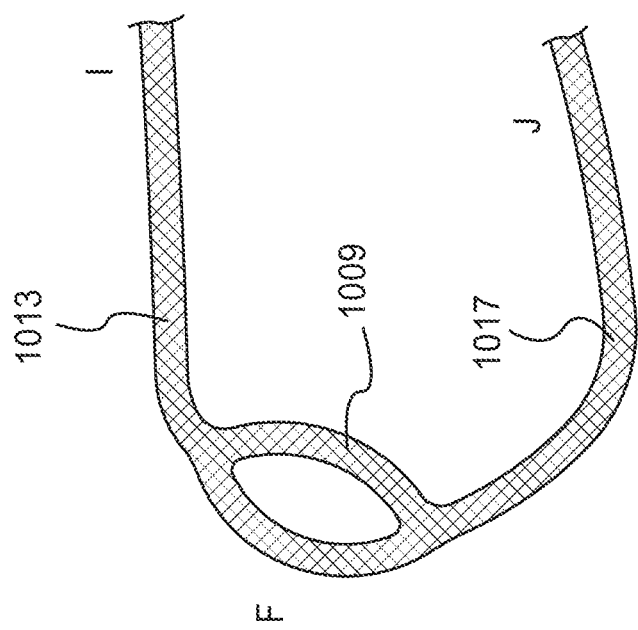
FIG. 55 is a perspective view of a portion of the actuation wire of FIG. 53.

FIGS. 53-55 illustrate an actuation wire 1074 that can be used with the delivery devices described herein. The actuation wire 1074 can be configured the same as actuator wires 874 and 974 in that it includes a center loop 1009 (also labeled F) and two end loops 1007 (also labeled G) and 1011 (also labeled H). The center loop 1009 is connected to the end loop 1007 by a strand 1017 (also labeled J) and the center loop 1009 is connected to the end loop 1011 by a strand 1013 (also labeled I).

FIGS. 53-55 illustrate a bifurcation process to form the loops 1009, 1007, 1011. For ease of discussion, reference will be made to reference labels F-I. Actuation wire 1074 is formed from a single strand (e.g., braided filament) with three bifurcations/unifications to create the loops F, G and H. FIG. 54 is an enlarged view of loop H (loop G is the same) and FIG. 55 is an enlarged view of the loop F. As shown in FIGS. 53-55, the bifurcation process results in a small tail portion on loops G and H. As with actuation wire 974, the formation of actuation wire 1074 can result in no increase in the profile or thickness of the strand where it transitions from strand portions to the loops (e.g., strand I to loop H or strands I and J to loop F). There are also no raised portions or steps between the strands and the loops.

Figure 56:
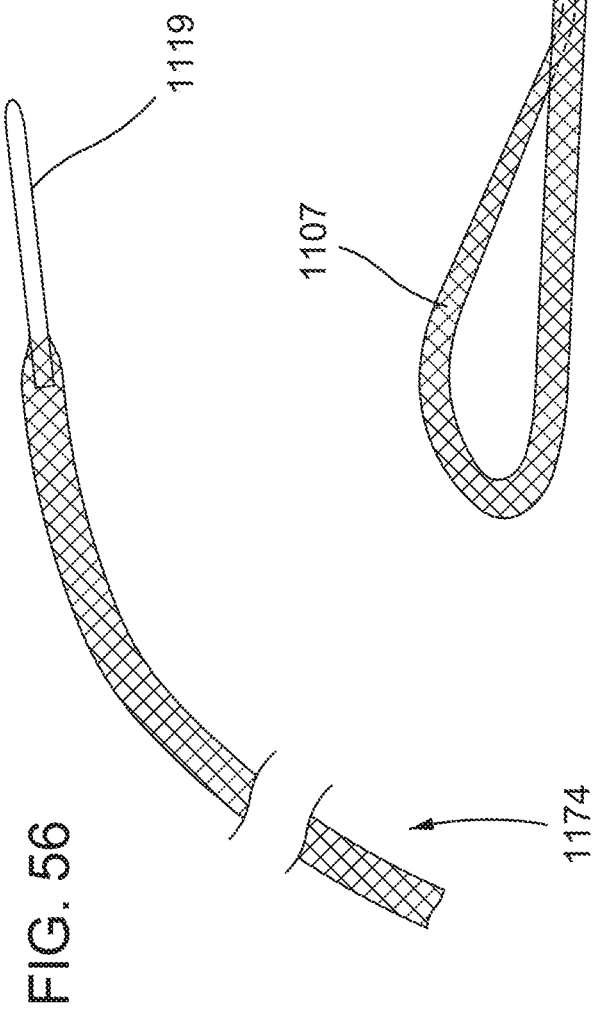
FIGS. 56-58 each illustrate a portion of an actuation wire according to another embodiment.
Figure 57:
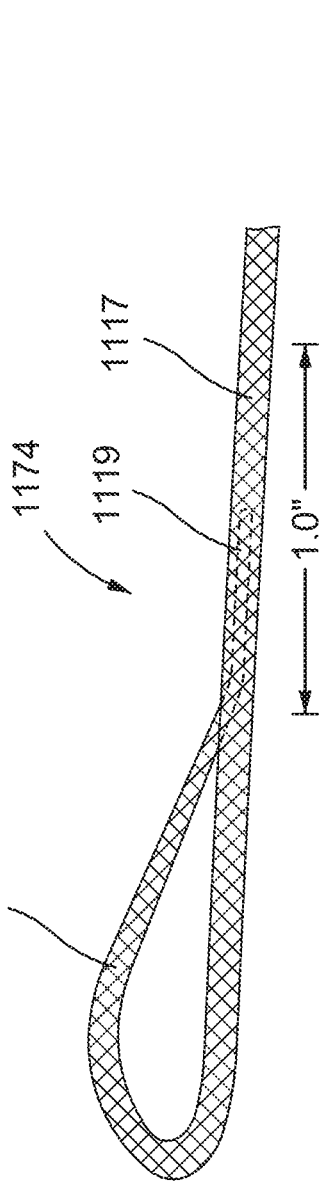
Figure 58:
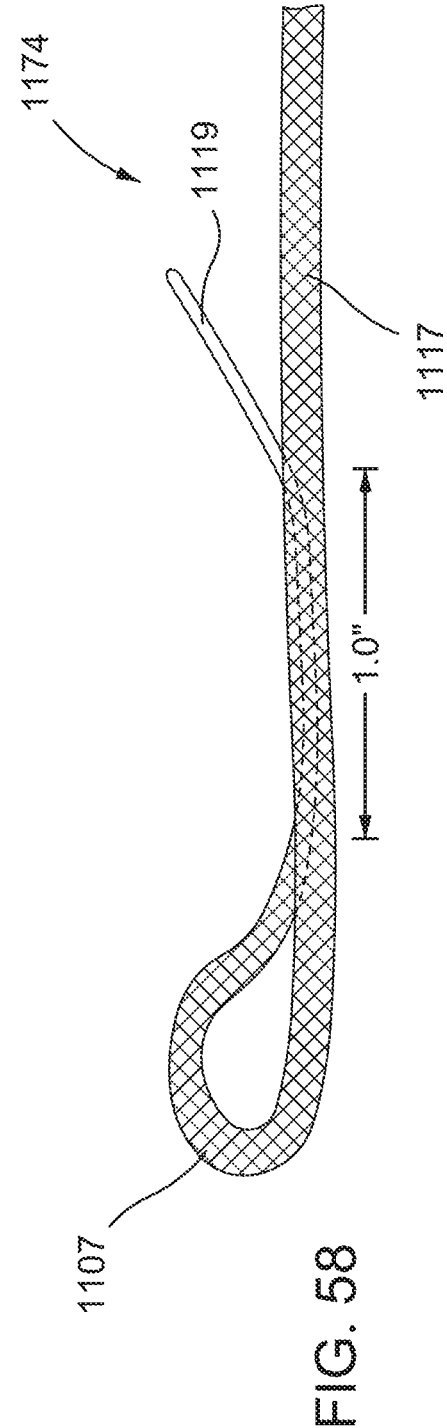
Figures 59A, 59B:
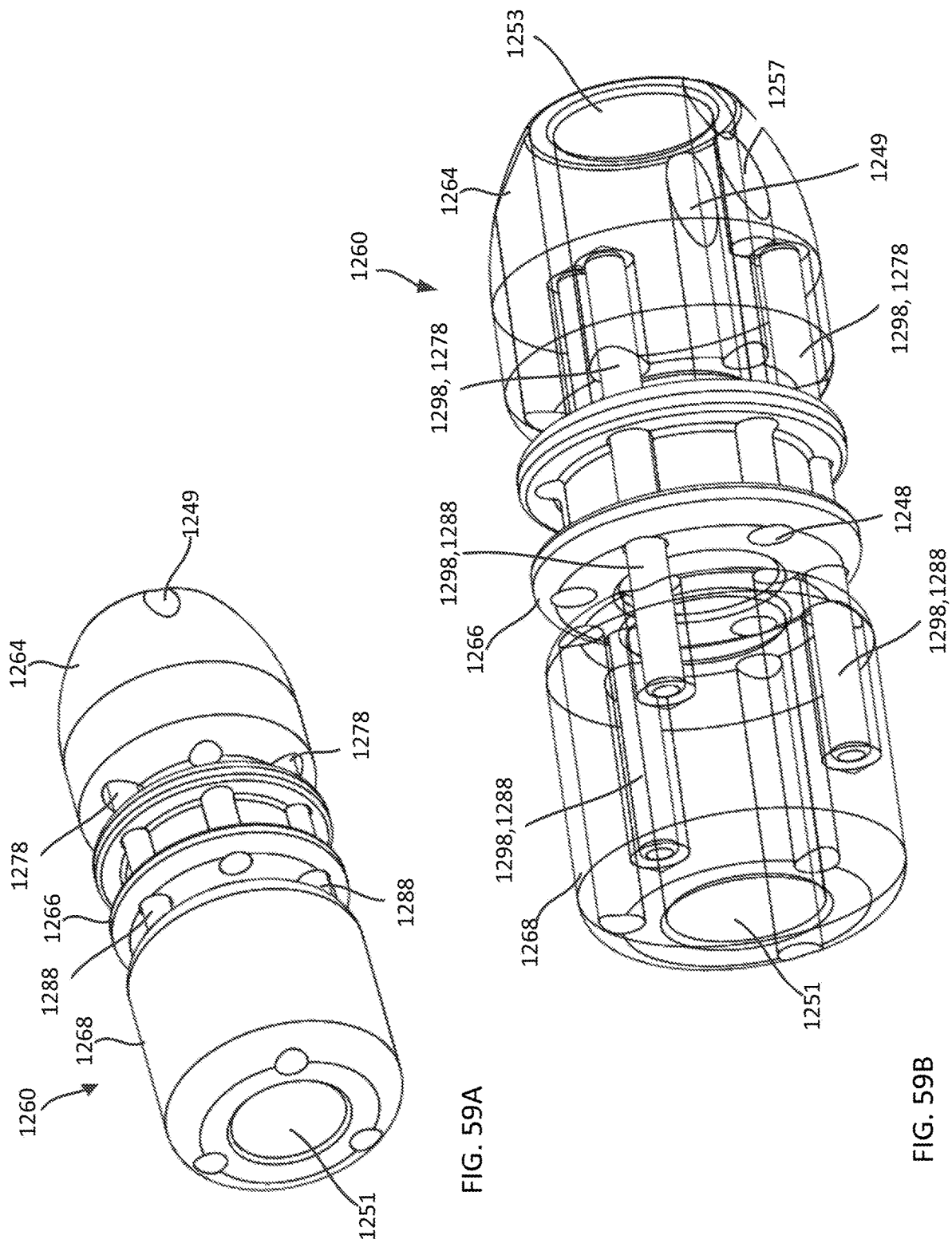
FIG. 59A is a perspective distal end view of a retention device, according to an embodiment.
FIG. 59B is a perspective distal end view of the retention device shown partially transparent for illustration purposes.

FIGS. 56-58 illustrate a portion of another actuation wire 1174 that can be used with the delivery devices described herein. The actuation wire 1174 can be configured the same as actuator wires 874, 974 and 1074 in that it includes a center loop (not shown) and two end loops (only end loop 1107 is shown). The center loop of actuation wire 1174 can be formed in the same manner as described above for either actuation wire 974 or actuation wire 1074. FIGS. 56-58 illustrate another method to form the end loops. Only end loop 1107 is described, but it should be understood that the end loop on the other end of the actuation wire can be constructed the same.

As shown in FIG. 56, a guide rod 1119 is glued or otherwise affixed to the end of the strand 1117. The guide rod 1119 is then inserted back into the material of the strand 1117 to lead the strand 1117 into itself for approximately 2 inches, effectively make a loop 1107 with a "Chinese finger" method of securement, as shown in FIGS. 57 and 58. The guide rod 1119 is pulled back out through a side of the strand 1117 and then removed (e.g., cut) from the strand 1117.

FIGS. 59A-64B illustrate a retention device 1260 that can be included with any of the delivery devices described herein, and used to retain and release actuation wires coupled to a prosthetic valve during delivery of the prosthetic valve to a heart of a patient. The function and operation of the retention device 1260 can be the same as or similar to the previous embodiments, and therefore, some details are not described with respect to this embodiment.

The retention device 1260 includes a first or proximal retention member 1264 that is fixedly coupled to a distal end portion of the tube member (not shown) as described above for previous embodiments, a second or center retention member 1266 that is movably coupled to the proximal retention member 1264 and a third or distal retention member 1268 that is movably coupled to the center retention member 1266 and the proximal retention member 1264. The center retention member 1266 can be coupled to the proximal retention member 1264 via a first actuation rod (not shown), and the distal retention member 1268 can be coupled to the center retention member 1266 and to the proximal retention member 1264 via two second actuation rods (not shown) in the same or similar manner as described above for previous embodiments.

The actuation rods can extend to a proximal end of the delivery device to which the retention member 1260 is attached and be operably coupled to a handle assembly (not shown). For example, the second actuation rods can extend into apertures/lumens 1241 defined by the distal retention member 1268 and be fixedly attached to the distal retention member 1268, slidably extend through apertures/lumens 1248 defined by the center retention member 1266 and through apertures/lumens 1249 defined by the proximal retention member 1264 such that the distal retention member 1268 can be slidably moved relative to the center retention member 1266 and the proximal retention member 1264. The first actuation rod can extend within an aperture 1248 of the center retention member 1266 and be fixedly attached thereto, and slidably extend through an aperture 1249 of the proximal retention member 1264 such that the center retention member 1266 can be slidably moved relative to the proximal retention member 1264. The proximal retention member 1264 can be fixedly attached to the tube member (not shown) with a connecting rod (not shown). For example, the connecting rod can extend into an aperture 1257 defined at the proximal end of the proximal retention member 1264 and be fixedly attached thereto such that the proximal retention member 1264 can move with the tube member.

The retention device 1260 defines a lumen through which a valve holder (as described herein) can be movably disposed. For example, each of the distal retention members 1268 defines a lumen 1251, the center retention member 1266 defines a lumen 1253 and the proximal retention member 1264 defines a lumen 1255. A valve holder and elongate member coupled thereto can be movably disposed within each lumen of the retention device 1260.

In this embodiment, the retention device 1260 includes three pins 1298 that are fixedly attached to the center retention member 1266 and that can be used to releasably hold actuation wires to a delivery device in the same or similar manner as described above for previous embodiments. The pins 1298 can be, for example, welded to the center retention member 1266. In this embodiment, the pins 1298 extend through apertures/lumens 1272 defined by the center retention member 1266 and are fixedly attached thereto. The pins 1298 include a proximal pin portion 1278 that extends between the center retention member 1266 and the proximal retention member 1264, and a distal pin portion that extends between the center retention member 1266 and the distal retention member 1268. As shown in FIG. 60, the pins 1298 each have a different length. As described for previous embodiments, the pin portions 1278 can be received within apertures 1263 defined by the proximal retention member 1264 and the pin portions 1288 can be received within apertures 1261 defined by the distal retention member 1268.

FIGS. 65-68 illustrate an embodiment of a valve holder 1338 that can be used or included with a delivery system as described herein. The valve holder 1338 can be attached to an elongate member (no shown) such as elongate member 837 and 937 described above. The valve holder 1338 and elongate member can be movably disposed within a lumen (not shown) defined by an elongate tube member (e.g., 815, 915) and a lumen(s) defined by a retention device (e.g., 860, 960, 1260) of a delivery system described herein. In this embodiment the valve holder 1338 includes an insert or inner member 1322 that can be movably disposed within an interior region 1328 defined by an outer capsule 1324. For example, the insert 1322 of the valve holder 1338 can be operably coupled to a handle assembly via an actuation rod that extends through a lumen of the elongate member (e.g., 837, 937) that can be actuated to move the insert 1322 proximally and distally relative to the outer capsule 1324. In an alternative embodiment, the capsule 1324 of the valve holder 1338 can be operably coupled to a handle assembly via an actuation rod that extends through a lumen of the elongate member (e.g., 837, 937) that can be actuated to move the capsule 1324 proximally and distally relative to the inner insert 1322.

Figure 65:
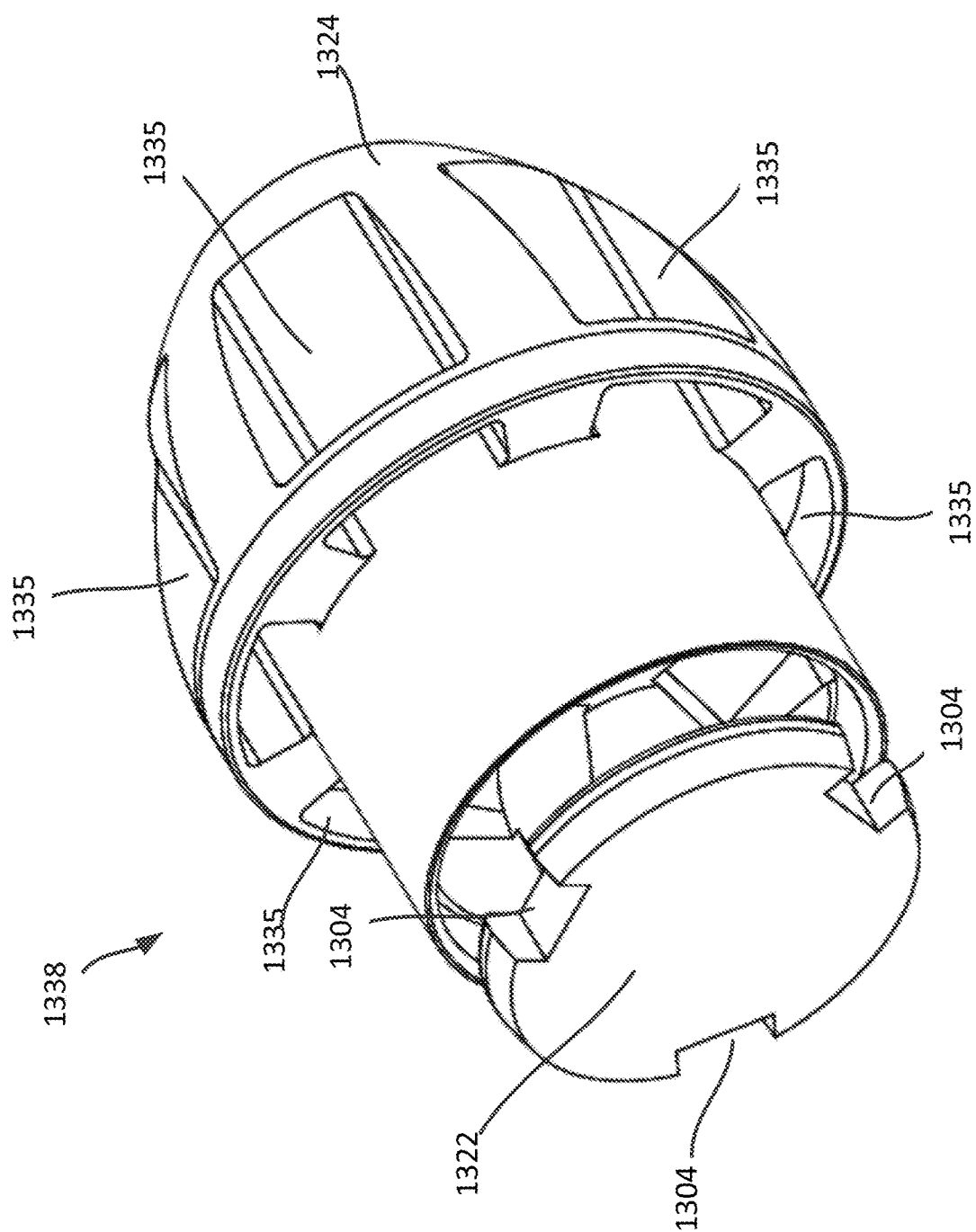
FIG. 65 is a distal end perspective view of a valve holder, according to an embodiment.
Figure 66:
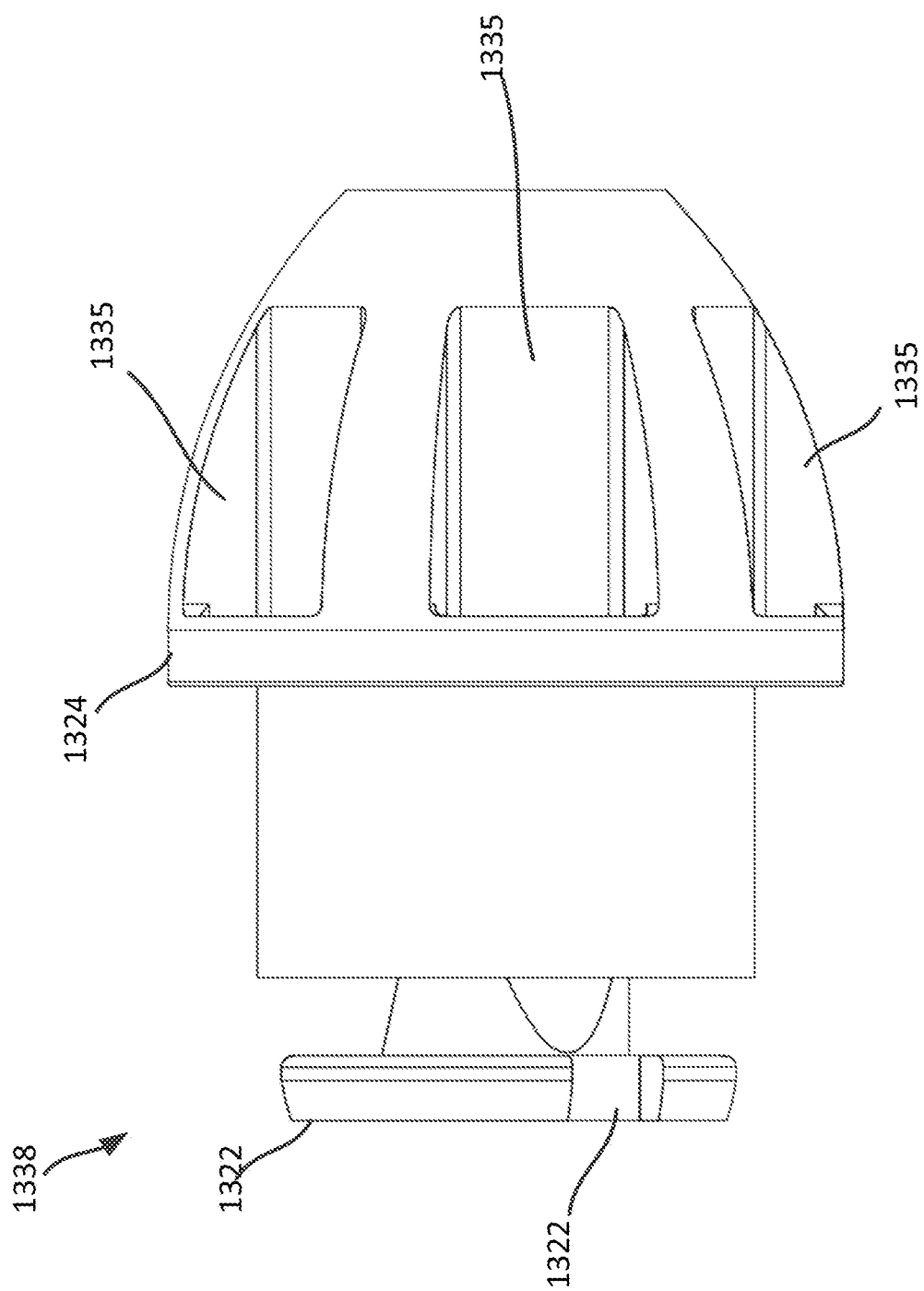
FIG. 66 is a side view of the valve holder of FIG. 65.

The insert 1322 defines recesses 1304 to which corresponding couplers (e.g., couplers 406) of the inner frame (not shown) of a prosthetic valve (not shown) can be releasably coupled in the same or similar manner as described above for delivery system 405 (see, e.g., FIGS. 26A-26C). In this manner, the valve holder 1338 can be used to hold the prosthetic valve to aid in the control and manipulation of the prosthetic valve as it is delivered and deployed. The insert 1322 is movably disposed within the interior region 1328 (see FIG. 68) of the capsule 1324. For example, the insert 1322 can be moved distally relative to the capsule 1324 such that the recesses 1304 are disposed outside the capsule 1324 (as shown in FIGS. 65 and 66) and the couplers on the valve can be inserted/placed within the recesses 1304. The insert 1322 can then be moved proximally relative to the capsule 1324 such that the insert 1322, along with the attached couplers, are moved to a position inside the interior region 1328 of the capsule 1324 and the couplers are unable to be removed from the valve holder 1338. To release the valve couplers from the valve holder 1338, the insert 1322 is moved distally relative to the capsule 1324 such that the recesses 1304 are again disposed distally outside of the interior of the capsule 1324, which in turn, allows the couplers of the valve to be released from the insert 1322 and valve holder 1338.

In an embodiment with the capsule 1324 movable relative to the insert 1322, the capsule 1324 can be moved proximally relative to the insert 1322 such that the recesses 1304 are disposed outside the capsule 1324 (as shown in FIGS. 65 and 66) and the couplers on the valve can be inserted/placed within the recesses 1304. The capsule 1324 can then be moved distally relative to the insert 1322 such that the insert 1322, and the attached couplers, are disposed inside the interior region 1328 of the capsule 1324 and the couplers are unable to be removed from the valve holder 1338. To release the valve couplers from the valve holder 1338, the capsule 1324 is moved proximally relative to the insert 1322 such that the recesses 1304 are again disposed distally outside of the interior 1328 of the capsule 1324, which in turn, allows the couplers of the valve to be released from the insert 1322 and valve holder 1338.

The capsule 1324 defines apertures 1335 through which actuation wires can be routed as described above for previous embodiments. For example, as shown for valve holder 938, each strand (e.g., 913, 917) of an actuation wire (e.g., 974) can be pinned by the retention device (e.g., 960) and routed through an aperture 1335 of the capsule 1324, pass through a loop or loops of the prosthetic valve and then pass back through the aperture 1335 and be pinned by the retention device. Thus, in an embodiment with three actuation wires and six strands, the capsule 1324 can include six apertures 1335.

Figure 70:
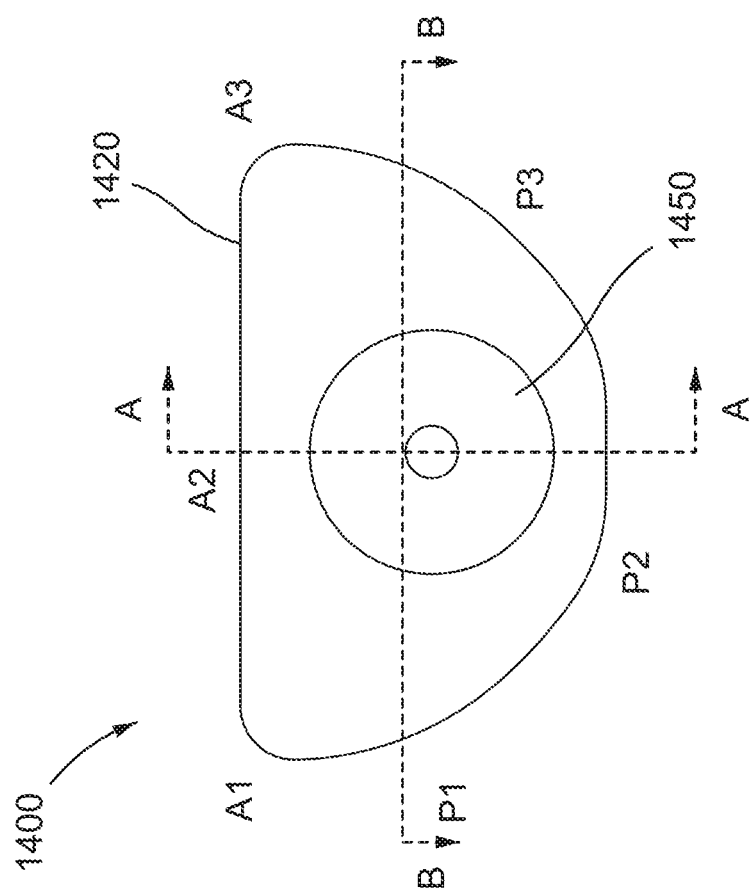
FIG. 70 is a top view of a prosthetic heart valve, according to another embodiment.
Figure 71:
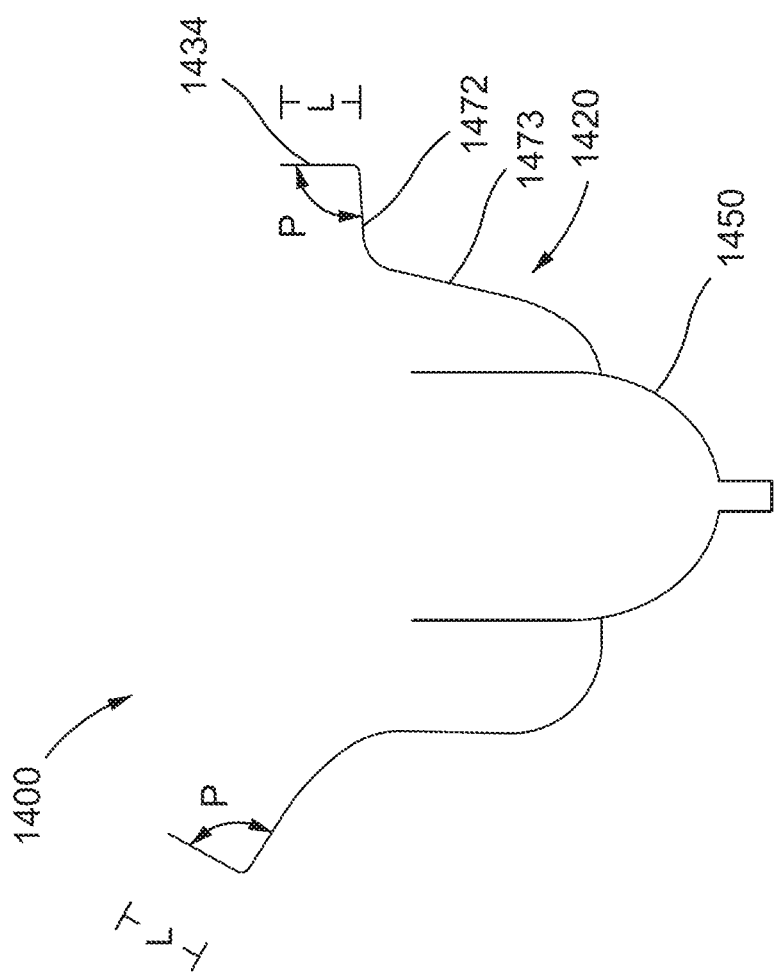
FIG. 71 is a cross-sectional view of the prosthetic heart valve of FIG. 70 the taken along line-A-A in FIG. 70.
Figure 72:
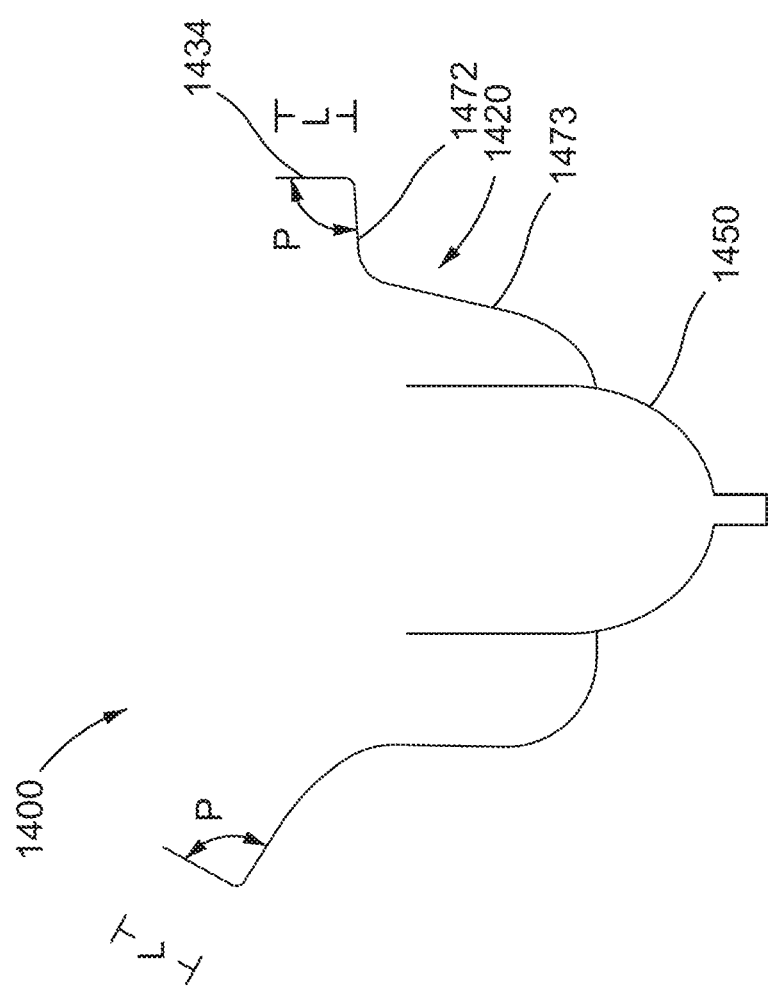
FIG. 72 is a cross-sectional view of the prosthetic heart valve of FIG. 70 the taken along line-B-B in FIG. 70.

FIGS. 70-73 illustrate another embodiment of a prosthetic valve that can be inverted for delivery of the prosthetic valve to a heart of a patient and reverted when being deployed in the heart. As shown in FIGS. 70-72, a prosthetic heart valve 1400 (e.g., a prosthetic mitral valve) includes an outer frame 1420 and an inner frame 1450. The prosthetic heart valve 1400 (also referred to as "valve" or "prosthetic valve") can include the same or similar features as the prosthetic heart valves described herein, and therefore, some features are not described with respect to valve 1400. For example, the prosthetic valve 1400 can include an inner valve assembly that includes the inner frame 1450 and an outer frame assembly that includes the outer frame 1450 and include the same or similar features as described above. The prosthetic valve 1400 is shown in a biased expanded configuration in FIGS. 70-72, and shown in an inverted configuration disposed within a delivery sheath 1426 of a delivery device or system 1405, in which the outer frame 1420 is inverted relative to the inner frame 1450, in FIG. 73.

Figure 73:
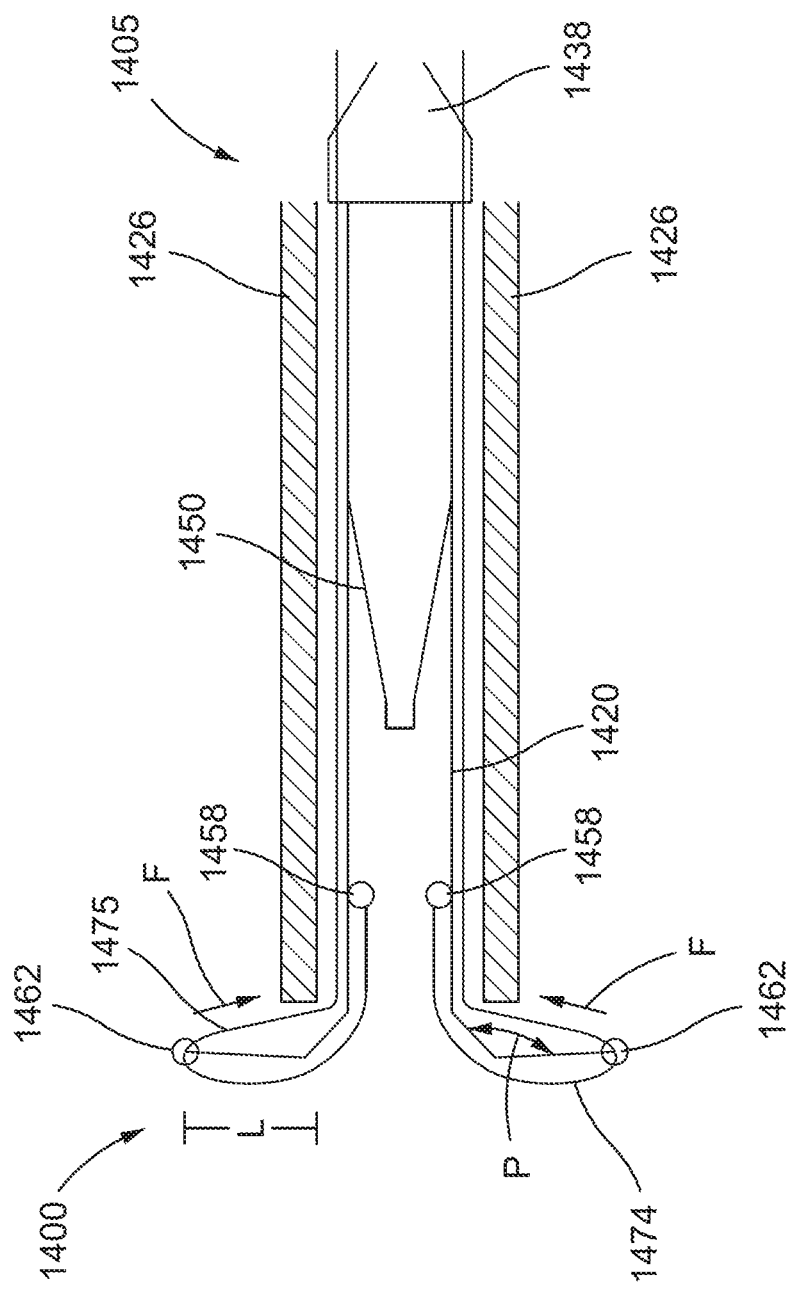
FIG. 73 is a side view of the prosthetic heart valve of FIGS. 70-72 shown inverted and disposed within a delivery device.

In this embodiment, the outer frame 1420 can include two rows of loops 1462 and 1458 (shown in FIG. 73) to which actuation wires 1474 and 1475 can be routed through in the same manner as described above, for example, with respect to valve 900. The actuation wires 1474, 1475 can be coupled to the delivery device 1405 as shown in FIG. 73, in the same manner as described above for previous embodiments. The delivery device 1405 can include the same or similar features and function in the same or similar manner as descried above for previous embodiments (e.g., 805, 905). For example, the delivery device 1405 can include a valve holder 1438 to which the inner frame 1450 can be releasably coupled during delivery of the prosthetic valve 1400 as described above (e.g., 838, 938, 1338). The delivery device 1405 can also include a retention device (not shown) as described above (e.g., 860, 960, 1260).

The outer frame 1420 includes a cuff portion 1472 and a body portion 1473 as described above, for example, with respect to valve 200 and outer frame 220. In this embodiment, the cuff portion 1472 has a shape and length that can assist the reverting process during delivery of the prosthetic valve 1400. More specifically, as shown in FIGS. 71 and 72, in this embodiment, the cuff portion 1472 includes an added segment 1434 that has a length L and is disposed at an angle P relative to the coincident or remaining cuff portion 1472. In other words, the added segment 1434 is disposed at a transverse angle relative to the remaining cuff portion 1472. The added segment 1434 can be, for example, formed integrally with the remaining portion of the cuff portion 1472 and extend therefrom. In some embodiments, the angle P can be, for example, 90 degrees or perpendicular (or substantially perpendicular) to the remaining cuff portion 1472.

With the cuff portion 1472 having an additional segment 1434 disposed perpendicular or near perpendicular to the remaining cuff portion 1472, during reversion or flipping (using the actuation wires) of the outer frame 1420 during delivery of the valve 1400, the cuff portion 1472 of the outer frame 1420 will "roll outward" from delivery sheath 1426, as shown in FIG. 73. The angled cuff portion 1472 (i.e., angle P between the segment 1434 and the remaining portion of the cuff portion 1472) helps pull the cuff tips away from the walls of the atrium as the outer frame 1420 is reverting, which is more atraumatic to the atrium.

FIG. 73 illustrates the valve 1400 disposed within a lumen of the delivery sheath 1426 in an inverted configuration, and the valve 1400 advanced partially outside of a distal end of the delivery sheath 1426, slightly past the segment 1434. Due to the shape of the cuff portion 1472 (with the segment 1434), the segment 1434 has exited the delivery sheath 1426 substantially perpendicular to the coincident remaining cuff portion 1472. Because the coincident cuff portion 1472 is still substantially linear or straight within the delivery sheath 1426, or just beginning to exit the delivery sheath 1426, the segment 1434 exits the delivery sheath 1426 at about a 90 degree angle relative to the delivery sheath 1426. Furthermore, because the outer frame 1420 rolls outward during the flipping/reverting, the segment 1434 has already began that process of reverting.

As shown in FIG. 73, the shape and configuration the outer frame also changes the force vectors F associated with the reverting/flipping of the outer frame 1420. In this embodiment, the force vectors F go from the tip of the cuff portion 1472 (e.g., at loops 1462) and extend at an angle back toward the outside of the delivery sheath 1426, which is in the direction the cuff portion 1472 needs to travel to roll outward and fully revert/flip.

Figure 74:
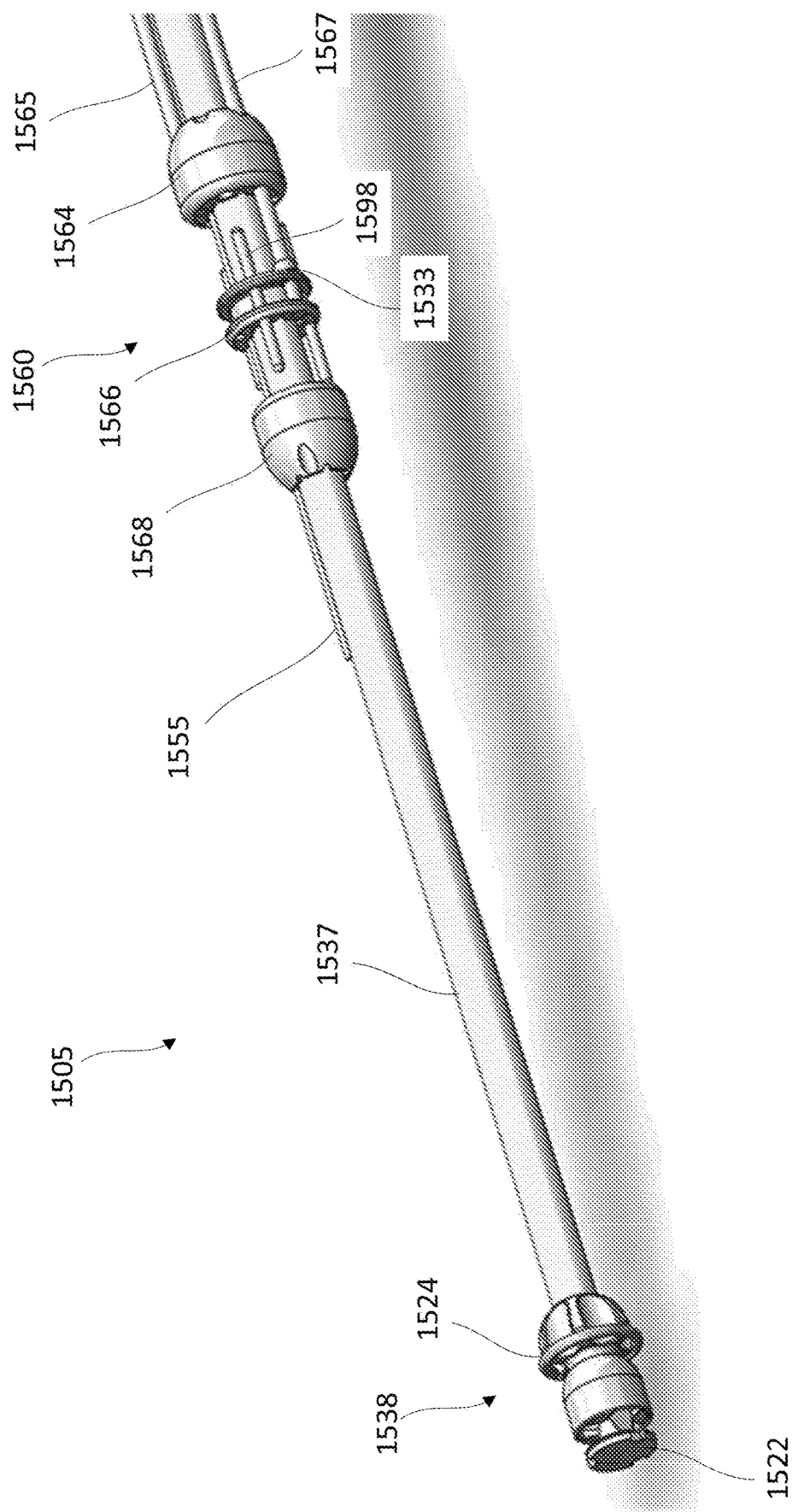
FIG. 74 is a side perspective view of a portion of a prosthetic heart valve delivery device, according to an embodiment.
Figure 75:
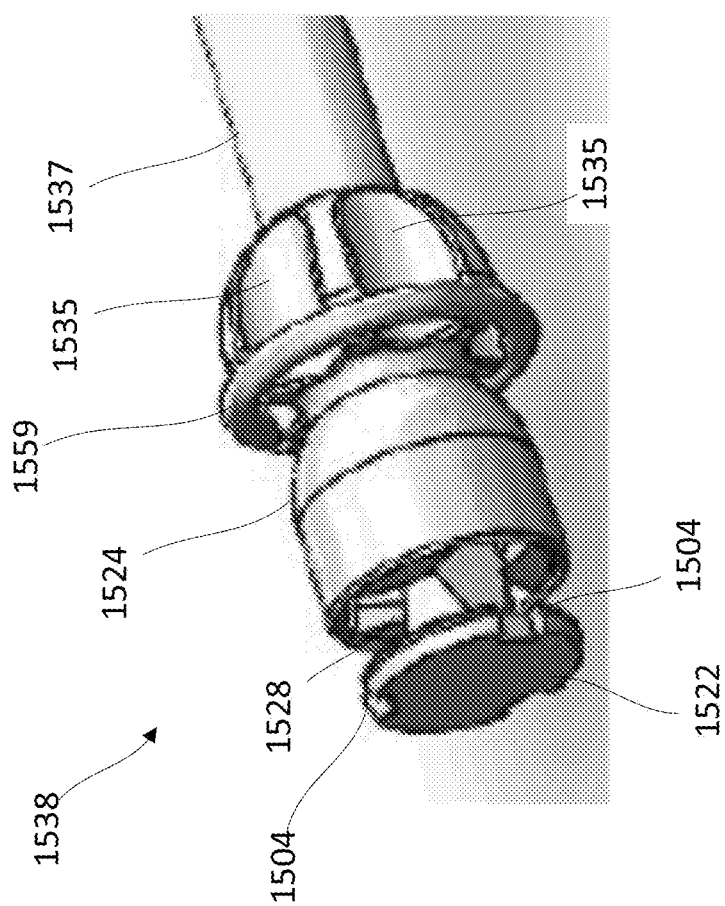
FIG. 75 is an enlarged side perspective view of the valve holder of the prosthetic heart valve delivery device of FIG. 74.
Figure 76:
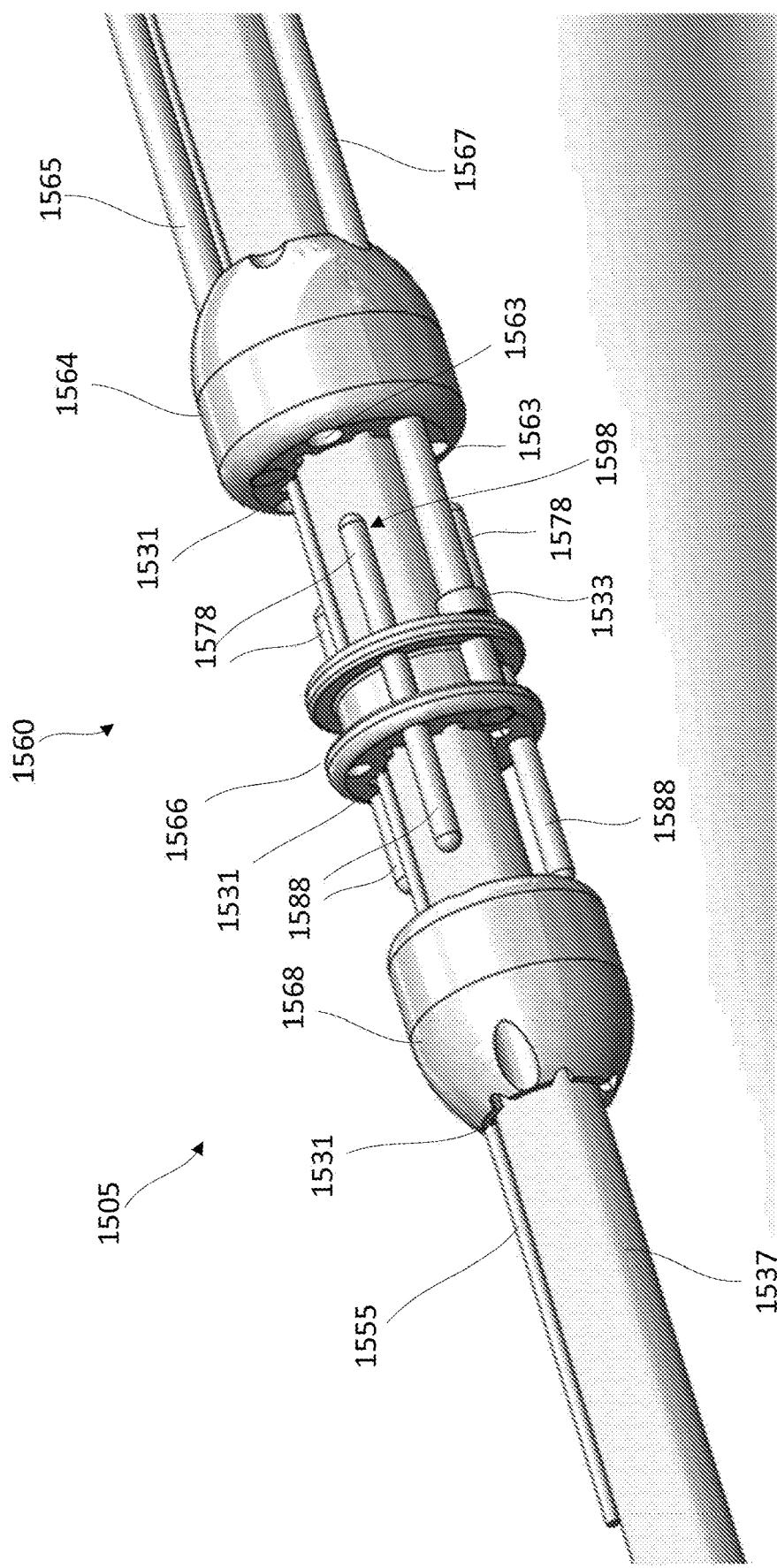
FIG. 76 is enlarged side perspective view of the retention device of the prosthetic heart valve delivery device of FIG. 74.

FIGS. 74-76 illustrate another embodiment of a delivery system 1505 (also referred to as "delivery device") that can be used to deliver and deploy a prosthetic heart valve within a heart in a procedure similar to or the same as the procedures described with respect to other embodiments described herein and embodiments described in the '305 PCT application incorporated herein by reference. Thus, some details regarding the valve and procedures performed therewith are not described with respect to this embodiment. It should be understood that for features and functions not specifically discussed, those features and functions can be the same as or similar to the valves described herein (e.g., the valve 200, 500) and/or in the '305 PCT application.

The delivery system 1505 can include the same or similar components as delivery systems 505 or 805 described above. The delivery system 1505 can include an outer delivery sheath (not shown) and an elongate tubular member, which can be slidably disposed within a lumen of the delivery sheath. In some embodiments, the delivery system 1505 may not include such an elongate member. The delivery system 1505 includes a valve holder 1538 and a retention device 1560 as described in more detail below.

As with other embodiments described herein and embodiments of the '305 PCT application, the delivery system 1505 can be used to deliver a valve that can be moved from a biased expanded configuration to an inverted configuration for delivery of the valve to the heart. To deploy the valve within a heart, the outer frame of the valve can be moved to an inverted configuration relative to the inner frame as described above for previous embodiments and placed within a distal end portion of the lumen of the delivery sheath.

The valve holder 1538 can be coupled to an elongate member 1537 that can be movably disposed within the lumen of the delivery sheath and/or a lumen of an elongate tubular member as described above for previous embodiments. In this embodiment the valve holder 1538 includes an insert or inner member 1522 that can be movably disposed within an interior region 1528 defined by an outer capsule 1524. For example, the insert 1522 of the valve holder 1538 can be operably coupled to a handle assembly (not shown) via an actuation rod that extends through a lumen of the elongate member 1537 that can be actuated to move the insert 1522 proximally and distally relative to the outer capsule 1524. In an alternative embodiment, the capsule 1524 of the valve holder 1538 can be actuated to move proximally and distally relative to the inner insert 1522.

The insert 1522 defines recesses 1504 to which corresponding couplers (e.g., couplers 406 described above) of the inner frame (not shown) of a prosthetic valve (not shown) can be releasably coupled in the same or similar manner as described above for delivery system 405 (see, e.g., FIGS. 26A-26C). In this manner, the valve holder 1538 can be used to hold the prosthetic valve to aid in the control and manipulation of the prosthetic valve as it is delivered and deployed. For example, the insert 1522 can be moved distally relative to the capsule 1524 such that the recesses 1504 are disposed outside the capsule 1524 (as shown in FIGS. 74 and 75) and the couplers on the valve can be inserted/placed within the recesses 1504. The insert 1522 can then be moved proximally relative to the capsule 1524 such that the insert 1522, along with the attached couplers, are moved to a position inside the interior region 1528 of the capsule 1524 and the couplers are unable to be removed from the valve holder 1538. To release the valve couplers from the valve holder 1538, the insert 1522 is moved distally relative to the capsule 1524 such that the recesses 1504 are again disposed distally outside of the interior of the capsule 1524, which in turn, allows the couplers of the valve to be released from the insert 1522 and valve holder 1538.

The capsule 1524 defines apertures 1535 through which actuation wires can be routed as described above for previous embodiments. For example, as shown and described above for valve holder 938, each strand of an actuation wire can be pinned by the retention device 1560 and routed through an aperture 1535 of the capsule 1524, pass through a loop or loops of the prosthetic valve and then pass back through the aperture 1535 and be pinned by the retention device 1560. Thus, in an embodiment with three actuation wires and six strands, the capsule 1524 can include six apertures 1535. In this embodiment, the capsule 1524 also includes a ring 1559 that can provide a radiused, smooth surface/contact point for actuation wires routed through the apertures 1535.

The delivery system 1505 also includes a retention device 1560 that defines a lumen through which the elongate member 1537 can be slidably disposed. As described above for previous embodiments, the retention device 1560 can be used to secure and release actuation wires (not shown) in the same or similar manner as described above for delivery system 805 and 905. The retention device 1560 includes retention components or members that are coupled together coaxially and can be actuated to secure and release actuation wires (not shown) coupled to the delivery system 1505. More specifically, the retention device 1560 includes a first or proximal retention member 1564, a second or center retention member and a third or distal retention member 1568. In this embodiment, the center retention member 1566 is fixedly coupled to a proximal portion of the delivery device 1505 such as a handle assembly (not shown). For example, as shown in FIGS. 74 and 75, a rod 1567 can be fixedly attached to the center retention member 1566 and fixedly attached to the proximal portion of the delivery device 1505. A rod 1565 can be fixedly coupled (e.g., welded) to the proximal retention member 1564 and can be operatively coupled to an actuation device (not shown) at the proximal end portion of the delivery device 1505 such that it can be actuated to move relative to the center retention member 1566. Similarly, the distal retention member 1568 can be coupled to an actuation device at the proximal end portion of the delivery device with a rod (not shown) such that the distal retention member 1568 can be actuated to move relative to the center retention member 1566. The actuation devices can each be, for example a lead screw that can be rotated to move the rod 1565 or 1567 proximally and distally, which in turn moves the proximal and distal retention members 1564 and 1568 proximally and distally. The actuation rod 1565 extends through an opening defined by the proximal retention member 1564 such that the rod 1565 can slidably move relative to the proximal retention member 1564. Similarly, the rod (not shown) coupled to the distal retention member 1568 can extend through openings in the proximal retention member 1564 and openings in the center retention member 1566 such that the rod can slidably move relative to the proximal retention member 1564 and the center retention member 1566.

An axial wire 1555 is attached to the elongate member 1537 and each of the proximal retention member 1564, the center retention member 1566 and the distal retention member 1568 include a cutout 1531 keyed to ride along the axial wire 1555. In other words, the keyed coupling of the retention members 1564, 1566, 1568 allows them to slide along the axial wire 1555, and thus the elongate member 1537, in an axial direction (proximal an distal), but prevents them from rotating relative to the elongate member 1537. This allows the retention device 1560 (e.g., retention members 1564, 1566, 1568) and the elongate member 1537 to be rotated together in unison and prevents actuation wires attached to the retention device 1560 (e.g., 1564, 1566, 1568) from becoming entangled and wrapping around the elongate member 1537 during use to deliver and deploy a prosthetic heart valve. Multiple cutouts 1531 can be included, as shown in FIGS. 74 and 76 such that more than one axial wire can be included and/or the retention device 1560 (retention members 1564, 1566, 1568) can be positioned at different radial positions along the elongate member 1537.

Three pins 1598 are fixedly attached to the center retention member 1566 and extend through openings in the center retention member 1566 such that proximal pins or pin portions 1578 extend proximally from the center retention member 1566, and distal pins or pin portions 1588 extend distally from the center retention member 1566. The pins 1578 and 1588 can be used to releasably hold actuation wires to the delivery device 1505 in the same or similar manner as described above for delivery system 805 or 905. The actuation wires can be any of the actuation wires described herein. The pins 1578 can be received within apertures/lumens defined by the proximal retention member 1564 and the pins 1588 can be received within apertures/lumens defined by the distal retention member 1568. In this embodiment, the pins 1578 each extend proximally at different lengths from the center retention member 1566, and the pins 1588 each extend distally at different lengths from the center retention member 1566. In this embodiment, the center retention member 1566 also includes one or more spacers 1533 on each side (proximal and distal) of the center retention member 1566 (only one spacer 1533 is shown in FIG. 76). The spacers 1533 can prevent the retention members 1564, 1566, 1568 from contacting one another when actuated to secure actuation wires thereto and thus prevent any possible damage to the actuation wires. Spacers can alternatively be included on the proximal side of the distal retention member 1568 and on the distal side of the proximal retention member 1564.

As with previous embodiments, multiple actuation wires can be coupled to the outer frame assembly of the prosthetic valve to be delivered to a heart and used to help revert and manipulate the prosthetic valve into a desired position within the heart, and then can be released from the valve when the desired positioning has been achieved. More specifically, the outer frame of the valve can include loops at a free end portion of the outer frame and/or at a second location on the outer frame as described above for valve 900, through which the actuation wires can be threaded or received therethrough in the same or similar manner as described herein (e.g., with respect to valve 500) and/or in the '305 PCT application.

To prepare the delivery device to deliver a prosthetic valve to a heart of a patient, the actuation wires can be coupled to the valve as described above, and loops of the actuation wires can be secured to the retention device 1560 in a similar manner as described above for delivery devices 805 and 905. In this embodiment, to secure the loops to the retention device 1560, the proximal retention member 1564 is actuated to move distally toward the center retention member such that the pins 1578 are received within apertures 1563 (see, e.g., FIG. 76) of the proximal retention member 1564. The distal retention member 1568 can be actuated such that the pins 1588 are received in apertures (not shown) in the distal retention member 1568.

Figure 77:
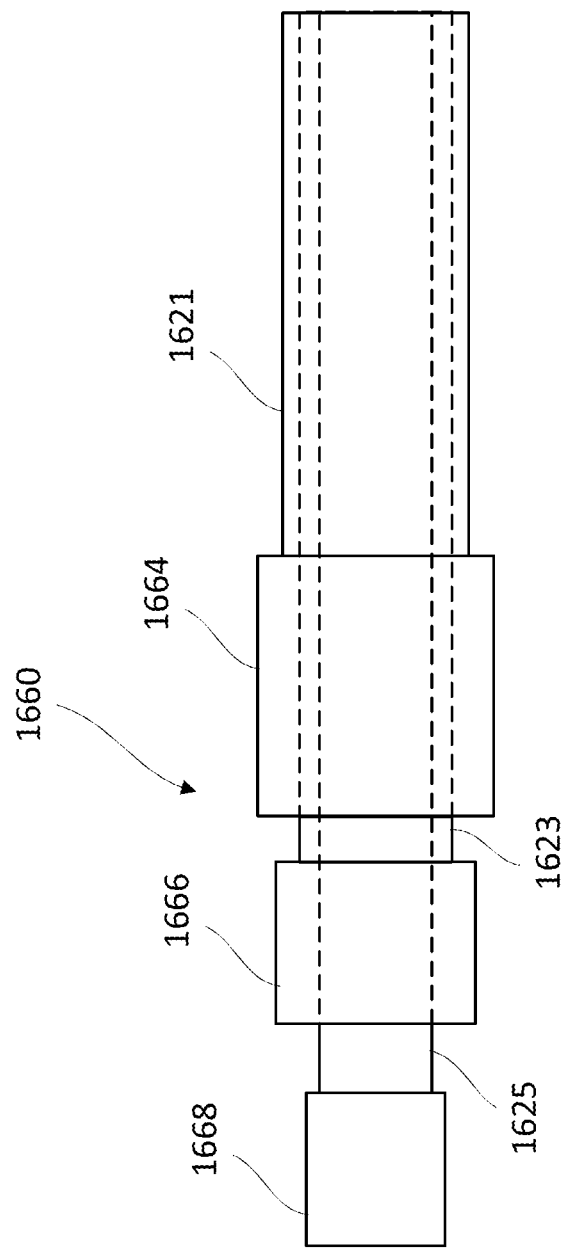
FIG. 77 is a schematic illustration of a retention device, according to another embodiment.

FIG. 77 is a schematic illustration of a retention device 1660, according to another embodiment. The retention device 1660 includes a proximal retention member 1664, a center retention member 1666 and distal retention device 1668. The retention device 1660 can include pins and other features (not shown) as described above for previous embodiments that can be used to secure actuation wires to the retention device 1660. In this embodiment, the retention members 1664, 1666, 1668 are each attached to a tube that extends to a proximal end portion of the delivery device (e.g., to a handle assemble). The tubes can be actuated proximally and distally to move two of the retention members to secure loops of actuation wires (not shown) to the retention device 1660. More specifically, the proximal retention device 1664 is attached to a tube 1621, the retention member 1666 is attached to a tube 1623 and the distal retention member 1668 is attached to a tube 1625. The tubes 1621, 1623, 1625 are disposed concentrically with the tube 1623 movably disposable within a lumen defined by the proximal retention member 1664 and the tube 1621, and the tube 1625 movably disposable within a lumen defined by the retention member 1666 and the tube 1623. The distal retention member 1668 and the tube 1625 each also define a lumen such that an elongate member (e.g., 837, 837, 1537) coupled to a valve holder (e.g., (838, 938, 1538) can be slidably received through the lumens of the retention members and tubes.

Figure 78:
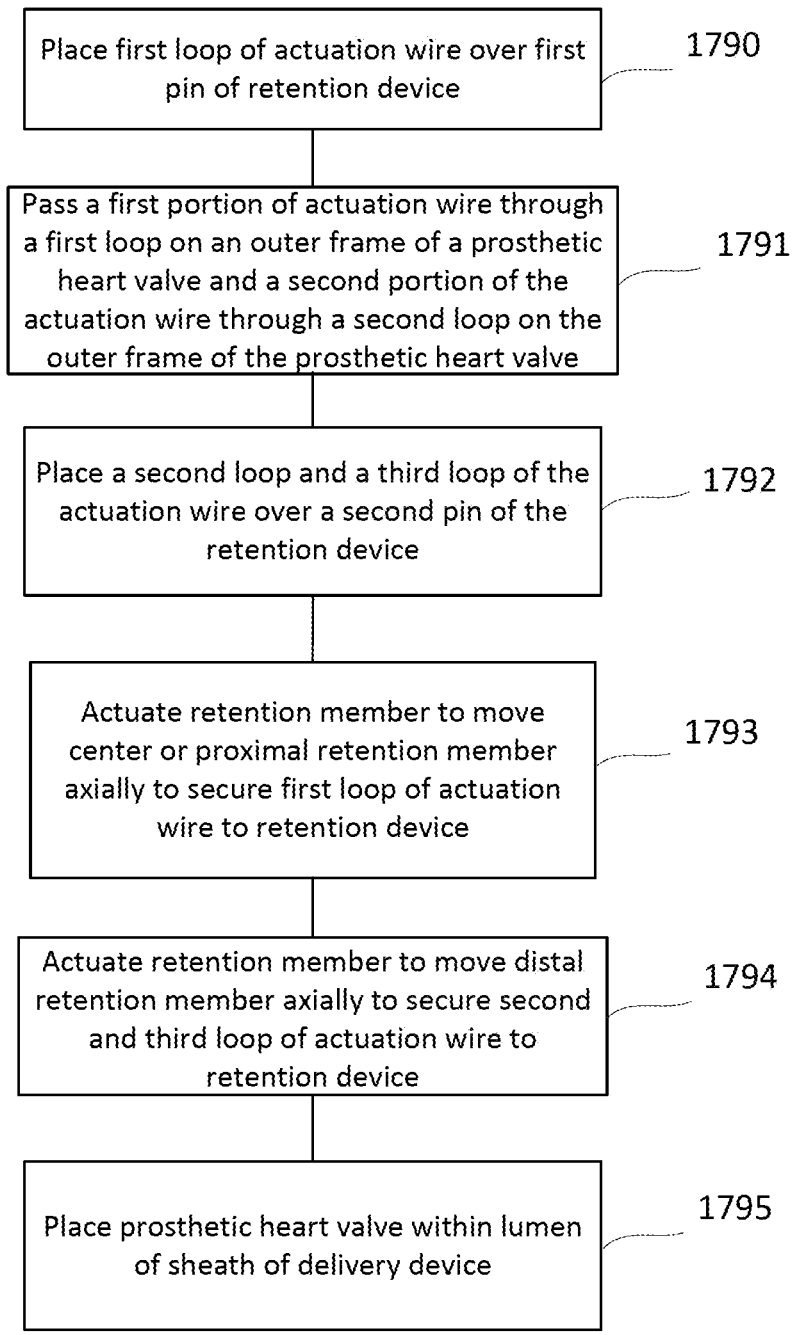
FIG. 78 is a flowchart illustrating a method of preparing a delivery device with a prosthetic valve to be delivered to a heart of a patient.

FIG. 78 is a flowchart of a method of preparing a delivery device with a prosthetic valve to be delivered to a heart of a patient as described herein. At 1790, a first loop of an actuation wire is placed over a first pin of a retention device of a prosthetic heart valve delivery device. The retention device includes a proximal retention member defining a first opening, a center retention member including the first pin and defining a second opening, and a distal retention member including a second pin. At 1791, a first portion of the second portion of the actuation wire is passed through a second loop on the outer frame of the prosthetic heart valve. The first portion of the actuation wire has a second loop disposed on a first end of the actuation wire and the second portion of the actuation wire has a third loop on a second end of the actuation wire. At 1792, the second loop and the third loop of the actuation wire are placed over the second pin of the retention device. At 1793, the retention member is actuated to move one of the center retention member and the proximal retention member axially such that the first pin is disposed in the first opening and the first loop of the actuation wire is secured to the retention device. At 1794, the retention member is actuated to move the distal retention member axially such that the second pin is disposed in the second opening and the second loop and the third loop of the actuation wire are secured to the retention device. At 1795, the prosthetic valve is placed within a lumen of a sheath of the delivery device.

Figure 79:
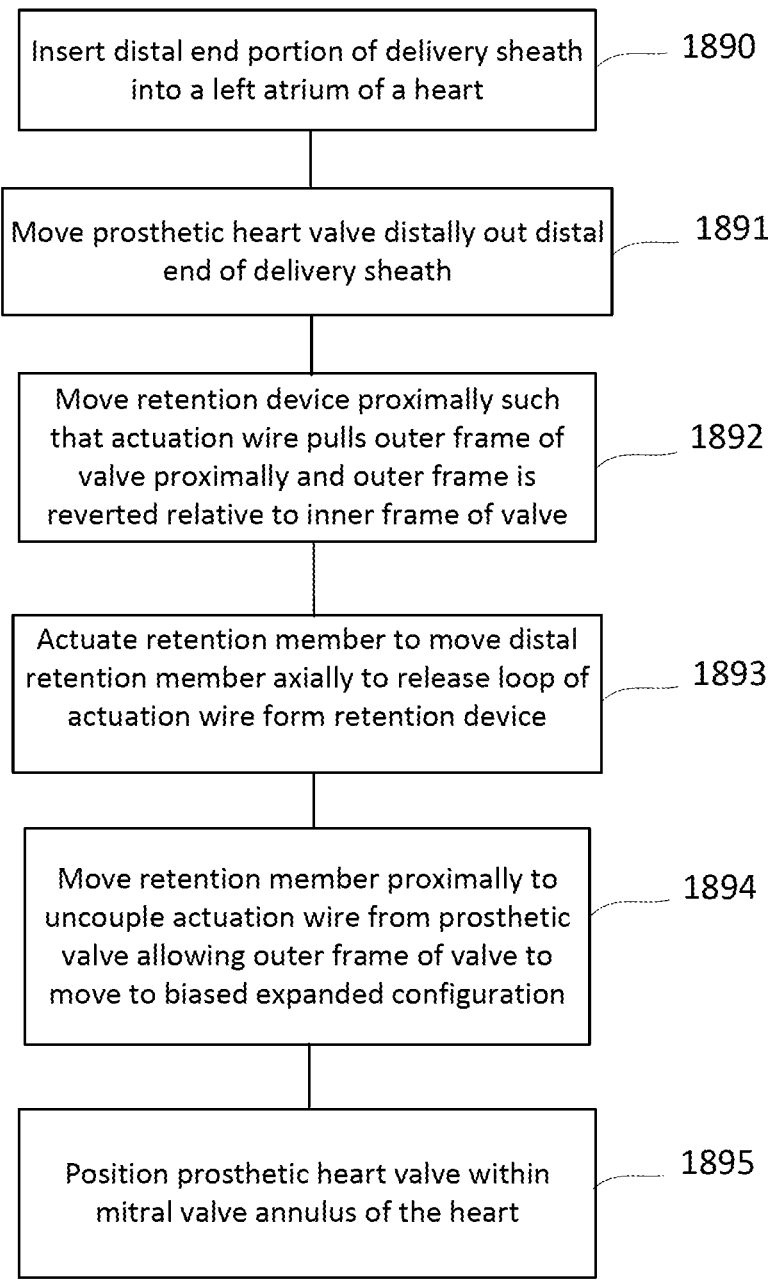
FIG. 79 is a flowchart illustrating a method of delivering a prosthetic heart valve to a heart of a patient.

FIG. 79 is a flowchart of a method of delivering a prosthetic heart valve to a heart of a patient using a delivery device as described herein. At 1890, a distal end portion of a delivery sheath of a valve delivery device is inserted into a left atrium of a heart. The delivery sheath has a prosthetic mitral valve disposed within a lumen of the delivery sheath, and the prosthetic mitral valve has an outer frame coupled to an inner frame, with the outer frame being inverted relative to the inner frame. The prosthetic heart valve being releasably coupled to a retention device that includes a proximal retention member defining a first opening, a center retention member including a first pin and defining a second opening, and a distal retention member including a second pin. An actuation wire is coupled to the prosthetic heart valve and includes a first loop secured to the retention device with the first pin and a second loop secured to the retention device with the second pin. At 1891, the prosthetic mitral valve is moved distally out the distal end portion of the delivery sheath. At 1892, the retention device is moved proximally such that the actuation wire pulls the outer frame of the prosthetic heart valve proximally and the outer frame is reverted relative to the inner frame. At 1893, the retention device is actuated such that the distal retention member moves axially relative to the center retention member and the second pin releases the second loop of the actuation wire. After actuating the retention device, at 1894, the retention device is moved proximally such that the actuation wire is pulled proximally and is uncoupled from the prosthetic heart valve allowing the outer frame of the prosthetic heart valve to move to a biased expanded configuration. At 1895, the prosthetic heart valve is positioned within a mitral valve annulus of the heart.

In some embodiments, a delivery system described herein (e.g., 505, 805, 905) can include a dilator device or member (not shown). The dilator can be, for example, a balloon dilator and can be configured to expand an opening or passage, for example, during delivery of the prosthetic valve. The dilator device can be the same as or similar to and used in the same or similar manner as dilator device 1711 described in the '305 PCT application with respect to FIGS. 43-48 and the method of delivery of FIG. 72. Further, the prosthetic heart valves described herein can be secured to a heart using an epicardial pad device as described with respect to FIGS. 43-48 and 72 of the '305 PCT application.

Further, although not shown, any of the embodiments of a delivery device or system can include a handle or handle assembly to which the various delivery sheaths and components can be operatively coupled and which a user (e.g., physician) can grasp and use to manipulate the delivery device or system. The handle or handle assembly can include actuators to actuate the various components of the delivery system.

In addition, the systems and methods described herein can also be adapted for use with a prosthetic tricuspid valve. For example, in such a case, a procedural catheter can be inserted into the right ventricle of the heart, and the delivery sheath delivered to the right atrium of the heart either directly (transatrial), or via the jugular or femoral vein.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

What is claimed is:
1. An apparatus, comprising:
an outer sheath defining a first lumen, the outer sheath configured to receive a prosthetic heart valve in a compressed configuration;
a tube member movably disposed within the first lumen of the outer sheath and defining a second lumen;
a valve holder, at least a portion of which is movably disposed within the second lumen of the tube member, the valve holder configured to be releasably coupled to a prosthetic heart valve during delivery of the prosthetic heart valve to a heart; and
a retention device coupled to a distal end portion of the tube member, the retention device including a proximal retention member defining a first opening, a center retention member including a first pin and defining a second opening, and a distal retention member including a second pin,
the proximal retention member being fixedly coupled to the tube member, the center retention member being axially movable relative to the proximal retention member between a first position in which the first pin is spaced from the proximal retention member and a second position in which the first pin is disposed within the first opening of the proximal retention member,
the distal retention member being axially movable relative to the center retention member between a first position in which the second pin is disposed at a spaced distance from the center retention member and a second position in which the second pin is disposed within the second opening,
the retention device configured to be actuated to secure an actuation wire releasably coupled to a prosthetic heart valve to the retention device when at least one of the center retention member is moved to its second position and the first pin secures a first loop of the actuation wire to the retention member or the distal retention member is moved to its second position and the second pin secures a second loop of the actuation wire to the retention device.
2. The apparatus of claim 1, further comprising:
a prosthetic heart valve disposed at least partially within the first lumen of the outer sheath, the prosthetic heart valve including an outer frame coupled to an inner frame,
the inner frame being removably coupled to a distal end portion of the valve holder,
the outer frame being movable between a first configuration relative to the inner frame and a second configuration relative to the inner frame in which the outer frame is inverted relative to the inner frame, the prosthetic heart valve being disposed within the first lumen of the outer sheath and the second lumen of the tube member with the outer frame in the second configuration, the actuation wire being releasably coupled to the outer frame.

3. The apparatus of claim 1, wherein the valve holder includes an elongate member, the elongate member extending through a lumen defined in each of the proximal retention member, the center retention member and the distal retention member, each of the proximal retention member, the center retention member and the distal retention member being axially slidable relative to the elongate member but rotationally stationary relative to the elongate member.

4. The apparatus of claim 1, wherein the valve holder includes an insert movably disposable within an interior region defined by an outer capsule, the insert having a portion defining recesses each configured to receive a different coupler disposed on the prosthetic heart valve to releasably couple the prosthetic heart valve to the valve holder when the couplers are received within the recesses and the portion of the insert with the recesses is disposed within the interior region of the outer capsule, and to release the prosthetic heart valve when the portion of the insert with the recesses is disposed outside of the outer capsule.

5. The apparatus of claim 4, wherein the outer capsule defines an aperture through which an actuation wire releasably coupled to the prosthetic heart valve can be received therethrough.

* * * * *